US012714723B2

(12) United States Patent
Strayer et al.

(10) Patent No.: US 12,714,723 B2
(45) Date of Patent: Aug. 25, 2026

(54) COMPOSITIONS AND METHODS FOR CANCER THERAPY

(71) Applicant: AIM ImmunoTech Inc., Ocala, FL (US)

(72) Inventors: David R. Strayer, Ocala, FL (US); Thomas K. Equels, Ocala, FL (US)

(73) Assignee: AIM ImmunoTech Inc., Ocala, FL (US)

( * ) Notice: Subject to any disclaimer, the term of this patent is extended or adjusted under 35 U.S.C. 154(b) by 0 days.

(21) Appl. No.: 17/416,358

(22) PCT Filed: Dec. 20, 2019

(86) PCT No.: PCT/US2019/068044
§ 371 (c)(1),
(2) Date: Jun. 18, 2021

(87) PCT Pub. No.: WO2020/132560
PCT Pub. Date: Jun. 25, 2020

(65) Prior Publication Data

US 2022/0096518 A1 Mar. 31, 2022

Related U.S. Application Data

(60) Provisional application No. 62/885,143, filed on Aug. 9, 2019, provisional application No. 62/869,909, filed on Jul. 2, 2019, provisional application No. 62/792,765, filed on Jan. 15, 2019, provisional application No. 62/792,760, filed on Jan. 15, 2019, provisional application No. 62/783,834, filed on Dec. 21, 2018.

(51) Int. Cl.

| | |
|---|---|
| ***A61K 31/713*** | (2006.01) |
| ***A61K 31/282*** | (2006.01) |
| ***A61K 31/4745*** | (2006.01) |
| ***A61K 31/513*** | (2006.01) |
| ***A61K 31/519*** | (2006.01) |
| ***A61K 31/7068*** | (2006.01) |
| ***A61K 38/21*** | (2006.01) |
| ***A61K 39/395*** | (2006.01) |
| ***A61K 47/64*** | (2017.01) |

(52) U.S. Cl.
CPC .......... *A61K 31/713* (2013.01); *A61K 31/282* (2013.01); *A61K 31/4745* (2013.01); *A61K 31/513* (2013.01); *A61K 31/519* (2013.01); *A61K 31/7068* (2013.01); *A61K 38/212* (2013.01); *A61K 39/3955* (2013.01); *A61K 47/6455* (2017.08)

(58) Field of Classification Search
None
See application file for complete search history.

(56) References Cited

U.S. PATENT DOCUMENTS

| | | | | |
|---|---|---|---|---|
| 5,258,369 A * | 11/1993 | Carter | .................... | C07H 21/00 514/49 |
| 5,595,756 A | 1/1997 | Bally et al. | | |
| 2009/0175820 A1* | 7/2009 | Desai | .................. | C07D 307/20 424/85.4 |
| 2014/0170191 A1* | 6/2014 | Carter | ................. | C12N 15/117 424/278.1 |
| 2017/0232071 A1 | 8/2017 | Parker | | |

FOREIGN PATENT DOCUMENTS

| | | |
|---|---|---|
| WO | 2010/047835 A2 | 4/2010 |
| WO | 2016/019472 A1 | 2/2016 |
| WO | 2016/139362 A1 | 9/2016 |
| WO | 2016/187656 A1 | 12/2016 |
| WO | 2018/039205 A1 | 3/2018 |
| WO | 2018/053106 A1 | 3/2018 |
| WO | 2020/132560 A2 | 6/2020 |

OTHER PUBLICATIONS

AIM ImmunoTech Inc. and Merck Sharp & Dohme (Systemic Immune Checkpoint Blockade and Intraperitoneal Chemo-Immunotherapy in Recurrent Ovarian Cancer. Retrieved from <https://clinicaltrials.gov/ct2/show/record/NCT03734692>. First posted Nov. 8, 2018, ClinicalTrials.gov Identifier: NCT03734692).*

AIM ImmunoTech (Hemispherx Highlights Year-to-Date Progress, Outlines Key Objectives. Retrieved from <https://www.globenewswire.com/newsrelease/2017/12/19/1266163/29489/en/Hemispherx-Highlights-Year-To-Date-Progress-Outlines-Key-Objectives.html>. Published Dec. 19, 2017).*

Makker et al. (Gynecologic Oncology Research and Practice 2017, 4:19).*

International Preliminary Report On Patentability (Chapter I) issued in PCT/US2019/068044; Issued Jun. 16, 2021.

Topalian S. L. et al., "Safety, activity, and immune correlates of anti-PD-1 antibody in cancer", New England Journal of Medicine, Jun. 28, 2012, vol. 366, No. 26, pp. 2444-2454.

Fujii T. et al., "Biomarkers of response to immune checkpoint blockade in cancer treatment", Critical Reviews in Oncology/Hematology, Aug. 3, 2018, vol. 130, pp. 108-120.

(Continued)

*Primary Examiner* — Sharon X Wen
(74) *Attorney, Agent, or Firm* — Studebaker Brackett PLLC

(57) ABSTRACT

One aspect of this disclosure is directed to a method for treating a cancer in a subject in need thereof by administering to the subject at least a first compound and a second compound in any order together or separately. The first compound is an effective amount of a checkpoint inhibitor optionally with at least one pharmaceutically acceptable carrier. The second compound is an effective amount of an Therapeutic Double Stranded RNA (tdsRNA) optionally with at least one pharmaceutically acceptable carrier. The compounds can be administered together or separately. Compositions for the practice of the method are also described.

21 Claims, 8 Drawing Sheets

(56) References Cited

OTHER PUBLICATIONS

Rao S. V. et al., "Predictors of response and resistance to checkpoint inhibitors in solid tumors", (Sci Transl Med, vol. 9, eaah3560), Annals of Translational Medicine, vol. 5, No. 23, Sep. 19, 2017, pp. 1-6.
Jasani B. et al., "Ampligen: A potential toll-like 3 receptor adjuvant for immunotherapy of cancer", Vaccine, vol. 27, Feb. 5, 2009, pp. 3401-3404.
Heppner G. H. et al., "Tumor heterogeneity: biological implications and therapeutic consequences", Cancer and Metastasis Reviews, vol. 2, Mar. 1983, pp. 5-23, Netherlands.
Jain R. K., "Barriers to Drug Delivery in Solid Tumors", Scientific American, Jul. 22, 1994 , pp. 58-65.
Paul W. E., "Fundamental Immunology", Third Edition, Chapter 8, pp. 292-295, 1993, Raven Press, New York.
Maccallum R. M. et al., "Antibody-antigen interactions: contact analysis and binding site topography", Journal of Molecular Biology, vol. 262, Oct. 11, 1996, pp. 732-745.
Vajdos F. F. et al., "Comprehensive Functional Maps of the Antigen-binding Site of an Anti-ErbB2 Antibody Obtained with Shotgun Scanning Mutagenesis", Journal of Molecular Biology, vol. 320, Jul. 5, 2002, pp. 415-428.
Ferrara F. et al., "Recombinant renewable polyclonal antibodies", mAbs, vol. 7, No. 1, Jan. 14, 2015, pp. 32-41 (11 pages total), doi: 10.4161/19420862.2015.989047.
Sporn M. B. et al., "Chemoprevention of cancer", Carcinogenesis, vol. 21, No. 3, Mar. 1, 2000, pp. 525-530.
Auerbach R. et al., "Angiogenesis assays: Problems and pitfalls", Cancer and Metastasis Reviews, vol. 19, Jun. 2000, pp. 167-172, Netherlands.
Gura T., "Systems for identifying new drugs are often faulty", Science, vol. 278, No. 5340, Nov. 7, 1997, pp. 1041-1042.
Hait W. N., "Anticancer drug development: the grand challenges", Nature Reviews/Drug Discovery, Apr. 2010, vol. 9 pp. 253-254.
Gravanis I. et al., "The changing world of cancer drug development: the regulatory bodies' perspective", Chinese Clinical Oncology, vol. 3, No. 2, Jun. 2014, pp. 1-5.
Beans C., "Targeting metastasis to halt cancer's spread", PNAS, vol. 115, No. 50, Dec. 11, 2018, pp. 12539-12543.
Anonymous, "Systemic Immune Checkpoint Blockade and Intraperitoneal Chemo-Immunotherapy in Recurrent Ovarian Cancer," Study NCT03734692 (v2), Dec. 6, 2018, pp. 1-8.
Obermajer N. et al., "Restoration of antitumor effectiveness of PD-1 inhibition in immunotherapy-resistant "cold" tumors by combinatorial treatment enhancing the numbers of tumor-specific CTLs in tumor tissues", Journal of Immunotherapy of Cancer 2016, 4(Suppl 1 ), p. 230, Nov. 16, 2013.
Aagaard L. et al., "RNAi Therapeutics: Principles, Prospects and Challenges", Advanced Drug Delivery Reviews, 59 (2007), pp. 75-86, Mar. 16, 2007.
Warzocha K. et al., "Antisense strategy: biological utility and prospects in the treatment of hematological malignancies", Leukemia and Lymphoma, 24(3-4), pp. 267-281, Jan. 1997.
Guido R. V. C. et al., "Virtual screening and its integration with modern drug design technologies", Current Medicinal Chemistry, 15(1), pp. 37-46, Published 2008.
Clark J. D. et al., "Discovery and Development of Janus Kinase (JAK) Inhibitors for Inflammatory Diseases", J. Med. Chem., 57 (12), pp. 5023-5038, Jan. 13, 2014.
Casey Ager, et al., "31st Annual Meeting and Associated Programs of the Society for Immunotherapy of Cancer (SITC 2016): part two" Journal For Immunotherapy Of Cancer (2016), vol. 4, pp. 107-221.
Press Release: Hemispherx Announces New Data Showing Ampligen's Positive Role in Reprograming Tumor Microenvironment—Study Results Suggests Ampligen Could Materially Enhance the Effectiveness of Checkpoint Blockade Technology (Jun. 5, 2018), pp. 1-3, Retrieved from the Internet: URL:https://www.globenewswire.com/news-release/2018/06/05/1517183/0/en/Hemispherx-Announces-New-Data-Showing-Ampligen-s-Positive-Role-in-Reprograming-Tumor-Microenvironment.html [retrieved on Mar. 10, 2020].
Marie-Nicole Theodoraki, et al., Helicase-Driven Activation of NF kappa B-COX2 Pathway Mediates the Immunosuppressive Component of dsRNA-Driven Inflammation in the Human Tumor Microenvironment, Cancer Research, (2018) vol. 78, No. 15, pp. 4292-4302.
Abdou Y, et al., Chemokine modulation to enhance the effectiveness of pembrolizumab in patients with metastatic triple-negative breast cancer. Cancer Research 79 (2019) (4 Supplement) pages: Abstract OT2-06-02.
Anonymous: Table of Contents : Cancer Immunology Research 11 (2019) pp. 1-5. Retrieved from the Internet: <URL:https://cancerimmunolres.aacrjournals>. org/content/7/2 Supplement [retrieved on Mar. 10, 2020].
Anonymous: Table of Contents—Trials in Progress : Cancer Immunology Research 11 (2019) pp. 1-4, Retrieved from the Internet: <URL:https://cancerimmunolres.aacrjournals>. org/search/volume:7%20issue:2+Supplement%2Ojcode:canimm?facet toe-section-id! O != Trials%20in%20Progress:%20Poster%20Presentations%20-%20Proffered%20Abstracts [retrieved on Mar. 10, 2020].
Anonymous: Systemic Immune Checkpoint Blockade and Intraperitoneal Chemo-Immunotherapy in Recurrent Ovarian Cancer (2018) pp. 1-8. Retrieved from the Internet: <URL:https://clinicaltrials.gov/ct2/history> /NCT03734692?V2=View#StudyPageTop [retrieved on Mar. 10, 2020].
Anonymous: Immuno-Oncology Summit (2016), pp. 1-27. Retrieved from the Internet: <URL:https://www.immuno-oncologysummit.com/> uploadedFiles/Immuno Oncology Summit/Agenda/16/2016-The-Immuno~Oncology~Summit-Brochure.pdf [retrieved on Mar. 11, 2020.
Christopher F. Nicodemus et al., Toll-like receptor-3 as a target to enhance bioactivity of cancer immunotherapy; American Journal of Obstetrics & Gynecology (2010) vol. 202, No. 6, pp. 608.el-608.e8.
Annika De Sousa Linhares et al., Not All Immune Checkpoints Are Created Equal; Frontiers In Immunology (2018) vol. 9, pp. 1-15.
Laura Agresta et al., The Emerging Role of CD244 Signaling in Immune Cells of theTumor Microenvironment; Frontiers In Immunology (2018), vol. 9, pp. 1-9.
Abdou et al., Chemokine modulation to enhance the effectiveness of pembrolizumab in patients with metastatic triple-negative breast cancer [abstract]. In: Proceedings of the Fourth CRI-CIMT-EATI-AACR International Cancer Immunotherapy Conference: Translating Science into Survival; Sep. 30-Oct. 3, 2018; New York, NY. Philadelphia, PA: AACR; Cancer Immunol Res 2019.
International Search Report issued in PCT/US2019/068044; mailed Jun. 23, 2020.
Written Opinion issued in PCT/US2019/068044; mailed Jun. 23, 2020.
Aim Immunotech lnc.: "Hemispherx Announces the First Participant Received Initial Dosing in Breast Cancer Clinical rial Using Hemispherx? Ampligen and Pembrolizumab NYSE: AIM", Apr. 2, 2019, pp. 1-3. Cited in corresponding EP Application No. 19842974.8 on Jul. 3, 2023.
Abdou et al., Chemokine modulation to enhance the effectiveness of pembrolizumab in patients with metastatic triple negative breast cancer [abstract]. In: Proceedings of the 2018 San Antonio Breast Cancer Symposium; Dec. 4-8, 2018; San Antonio, TX. Philadelphia (PA): AACR; Cancer Res 2019;79(4 Suppl):Abstract nr OT2-06-02. Cited in corresponding EP Application No. 19842974.8 on Jul. 3, 2023.
Toshihiro et al., "Combinatorial Immunotherapy of Polyinosinic-Polycytidylic Acid and Blockade of Programmed Death-Ligand 1 Induce Effective CD8 T-cell Responses against Established Tumors", Clinical Cancer Research, vol. 20, No. 5, Mar. 1, 2014, pp. 1223-1234. Cited in corresponding EP Application No. 19842974.8 on Jul. 3, 2023.
Smith et al., "Trial Watch: Toll-like receptor agonists in cancer immunotherapy", Oncoimmunology, vol. 7, No. 12, Oct. 11, 2018 (Oct. 11, 2018), pp. e1526250-1-e1526250-15 Cited in corresponding EP Application No. 19842974.8 on Jul. 3, 2023.
Soliman et al., "Abstract 5018: Combination immunotherapy with PD-L1 blockade and Poly I:C in a murine breast cancer model",

(56) References Cited

OTHER PUBLICATIONS

Proceedings of the 105th Annual Meeting of the American Association for Cancer Research, Published Oct. 1, 2014, pp. 1-4. Cited in corresponding EP Application No. 19842974.8 on Jul. 3, 2023.

Plote et al., "Immune modulation by combination type I interferon and checkpoint blockade therapy in murine urothelial carcinoma", 105th Annual Meeting of the American Association of Immunologists, May 4, 2018-May 8, 2018, Journal of Immunology, vol. 200, May 8, 2018, pp. 1-2. Cited in corresponding EP Application No. 19842974.8 on Jul. 3, 2023.

Meyer, "Tumors Interrupt IRF8-Mediated Dendritic Cell Development to Overcome Immune Surveillance", May 2018, Washington University, St. Louis, Missouri. Cited in corresponding EP Application No. 19842974.8 on Jul. 3, 2023.

History of Changes for NCT03734692, "Systemic Immune Checkpoint Blockade and Intraperitoneal Chemo-Immunotherapy in Recurrent Ovarian Cancer", published Dec. 6, 2018, <https://clinicaltrials.gov/ct2/history/NCT03734692?V_2=View#StudyPageTop>, total 11 pages. Cited in corresponding AU Application No. 2019403445 on Sep. 13, 2024.

* cited by examiner

FIG. 1

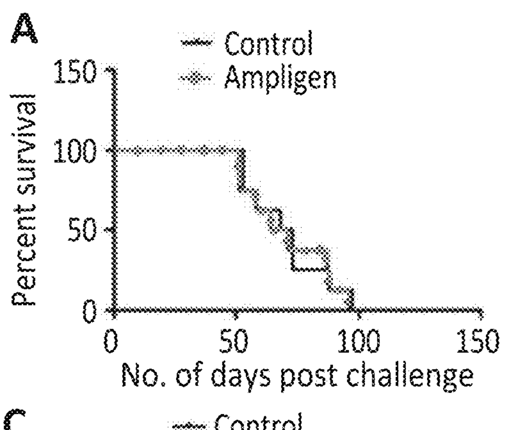
A
Control
Ampligen
Percent survival
150
100
50
0
0
50
100
150
No. of days post challenge

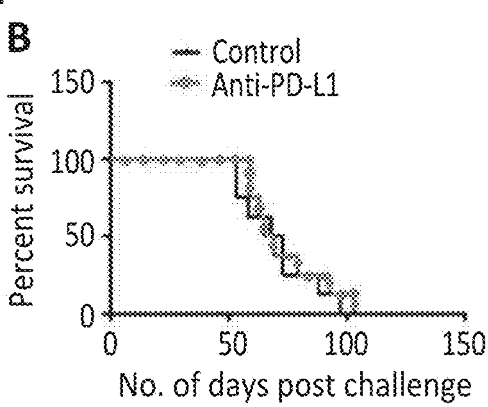
B
Control
Anti-PD-L1
Percent survival
150
100
50
0
0
50
100
150
No. of days post challenge

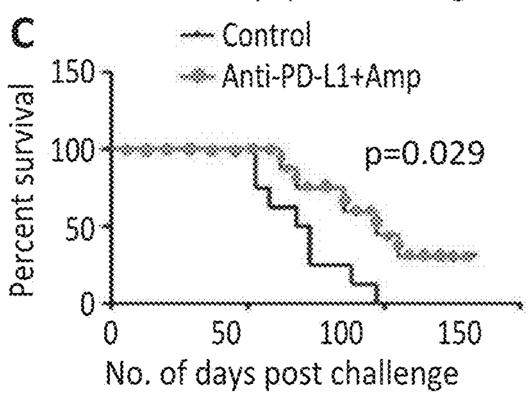
C
Control
Anti-PD-L1+Amp
p=0.029
Percent survival
150
100
50
0
0
50
100
150
No. of days post challenge

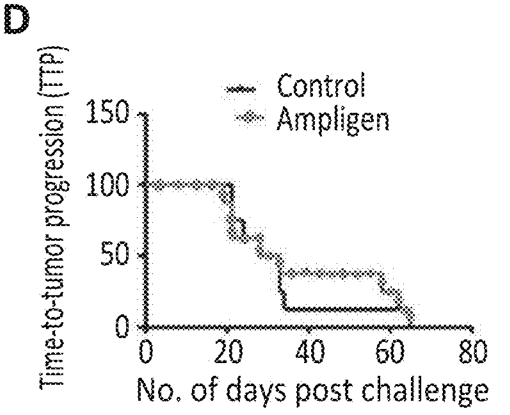
D
Control
Ampligen
Time-to-tumor progression (TTP)
150
100
50
0
0
20
40
60
80
No. of days post challenge

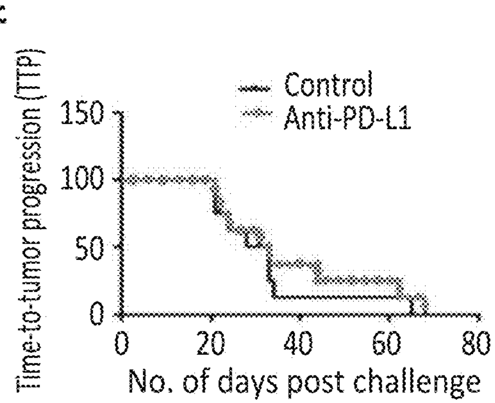
E
Control
Anti-PD-L1
Time-to-tumor progression (TTP)
150
100
50
0
0
20
40
60
80
No. of days post challenge

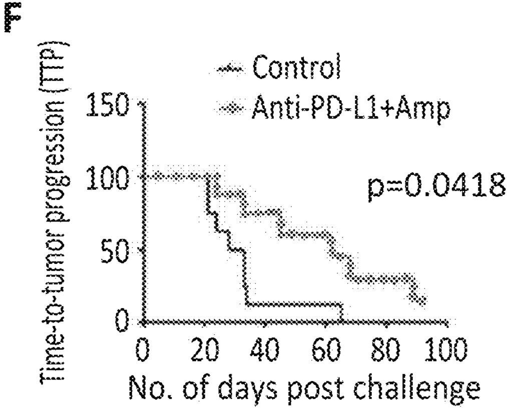
F
Control
Anti-PD-L1+Amp
p=0.0418
Time-to-tumor progression (TTP)
150
100
50
0
0
20
40
60
80
100
No. of days post challenge

| Low SIII | 164 | 65 | 25 | 8 | - | - |
|---|---|---|---|---|---|---|
| Low SIII | 141 | 28 | 6 | - | - | - |

FIG. 8

500 μg Ampligen

Control

% Survival 0 10 20 30 40 50 60 70 80 90 100

Days 0 20 40 60 80 100 120 140 160 180 200

COMPOSITIONS AND METHODS FOR CANCER THERAPY

CROSS-REFERENCE TO RELATED APPLICATIONS

This application is the U.S. National Stage of International Application No. PCT/US2019/068044 filed Dec. 20, 2019, which claims the benefit of priority to U.S. Provisional Application Ser. No. 62/885,143, filed Aug. 9, 2019, entitled "Compositions For Cancer Therapy And Methods"; U.S. Provisional Application Ser. No. 62/869,909, filed Jul. 2, 2019, entitled "Synergistic Cancer Compositions and Methods Involving Same"; U.S. Provisional Application Ser. No. 62/792,760, filed 15 Jan. 2019, entitled "Cancer Treatment Compositions and Methods"; U.S. Provisional Application Ser. No. 62/792,765, filed 15 Jan. 2019, entitled "Cancer Treatment Compositions and Methods"; and U.S. Provisional Application Ser. No. 62/783,834, filed 21 Dec. 2018, entitled "Cancer Treatment". All publications, patent applications, and patents mentioned in this disclosure are hereby incorporated by reference in their entirety as if each individual publication or patent was specifically and individually indicated to be incorporated by reference. In case of conflict, the present application, including any definitions herein, will control.

BACKGROUND

Immunotherapy is a rapidly growing field for the treatment of cancers, which, unfortunately, has experienced limited success. A growing arsenal of new drugs that unleash the body's immune system against tumors has captured the cancer treatment spotlight. Immunotherapy has had success in survival or symptom-free windows of time in a minority of patients. Unfortunately, immunotherapies help only a minority of patients with a given cancer type, and, in some types of cancers, they have had little or no success.

There is a need to develop methods and combination therapies to initiate or enhance the effectiveness of the checkpoint inhibitors in both the nonresponding subject population and the responding subject population. There is a long-felt need to discover why immunotherapies fail for some types of cancer and how they can be improved to work on more types of cancers.

BRIEF SUMMARY

In this disclosure, the term "in any aspect of the disclosure" is understood to comprise at least the meaning of "in any of the methods and compositions of this disclosure.

One aspect is directed to a method for treating a cancer in a subject in need thereof, the method comprising the steps of administering to the subject at least a first compound and a second compound in any order together or separately. In the method, the first compound comprises an effective amount of a checkpoint inhibitor optionally with at least one pharmaceutically acceptable carrier, and the second compound is an effective amount of a Therapeutic Double Stranded RNA (tdsRNA) optionally with at least one pharmaceutically acceptable carrier. The disclosure further provides a checkpoint inhibitor and a Therapeutic Double Stranded (tdsRNA) for use or in a method of the treatment of cancer or for use in the preparation of a medicament for the treatment of cancer. The checkpoint inhibitor and the tdsRNA may be administered at the same time or separately.

Treating cancer may comprise at least one selected from the group consisting of inhibiting a proliferation of a tumor in a subject; initiating an effect of a checkpoint inhibitor in a subject; enhancing the effects of a checkpoint inhibitor in a subject; prolonging the effects of a checkpoint inhibitor in a subject; and activating a response to a checkpoint inhibitor in the subject.

Any cancer may be treated by the method and compositions of this disclosure. In one aspect, the cancers at least one selected from the group consisting of: pancreatic cancer; skin cancer; colorectal cancer; ovarian cancer; melanoma; breast cancer; triple negative breast cancer; head and neck tumor; bladder cancer; renal cell carcinoma; and lung cancer. Preferably, the cancer is pancreatic cancer, colorectal cancer, melanoma, bladder cancer, or renal cell carcinoma.

In any aspect of this disclosure, the tdsRNA may be $rI_n$•$ribo(C_{4-29}U)_n$ or $rI_n$•$ribo(C_{11-14}U)_n$; preferably $rI_n$•$ribo(C_{11}U)_n$; $rI_n$•$ribo(C_{13}U)_n$; or $rI_n$•$ribo(C_{14}U)_n$; and most preferably $rI_n$•$ribo(C_{12}U)_n$.

In any aspect of this disclosure, the tdsRNA may be Rugged dsRNA. Rugged dsRNA is resistant to denaturation under conditions that are able to separate hybridized poly (riboinosinic acid) and poly(ribocytosinic acid) strands (rIn•rCn) of the same or similar length (e.g. of the same or similar value of n).

In any aspect of this disclosure, the Rugged dsRNA as a weight percent of total RNA in the methods or compositions may be greater than a value selected from the group consisting of: 1 weight percent; 5 weight percent; 10 weight percent; 20 weight percent; 30 weight percent; 40 weight percent; 50 weight percent; 60 weight percent; 70 weight percent; 80 weight percent; and 90 weight percent.

In any aspect of this disclosure, the tdsRNA may have a lower length of 40; 50; 60; 70; 80; or 380 and the same tdsRNA may have an upper length of 50,000; 10,000; 9000; 8000; 7000; or 450. Any lower length may be combined with any upper length described above. For example, the tdsRNA in any aspect of this disclosure may have a length or the value of "n" of between 40 to 50,000 base or basepairs depending on whether one strand or both strands are measured. In a preferred embodiment in any aspect of this disclosure, the length or value of "n" may be 50 to 10,000; 60 to 9000; 70 to 8000; 80 to 7000; or 380 to 450. Preferably, n is from 40 to 50,000; 50 to 10,000; 60 to 9000; 70 to 8000; 80 to 7000; or 380 to 450.

In any aspect of this disclosure, the tdsRNA may have between 4 to about 5000 helical turns of duplexed RNA strands, preferably 30-38 helical turns of duplexed RNA.

In any aspect of this disclosure, the tdsRNA may have a molecular weight from about 2 kilodalton to about 30,000 kilodalton, preferably 250 kilodaltons to 320 kilodaltons.

In any aspect of this disclosure, the tdsRNA may have a linear structure without a branching RNA structure.

In any aspect of this disclosure, the second compound comprises tdsRNA and at least 30 weight percent of total dsRNA is a linear structure; at least 40 weight percent of total dsRNA is a linear structure; at least 50 weight percent of total dsRNA is a linear structure; at least 60 weight percent of total dsRNA is a linear structure; at least 70 weight percent of total dsRNA is a linear structure; at least 80 weight percent of total dsRNA is a linear structure; or at least 90 weight percent of total dsRNA is a linear structure. In any aspect of this disclosure, the tdsRNA is complexed with a stabilizing polymer. For example, the stabilizing polymer may be selected from the group consisting of polylysine; polylysine plus carboxymethylcellulose; polyarginine; polyarginine plus carboxymethylcellulose; and a combination thereof.

In any aspect of this disclosure, the tdsRNA may be selected from the group consisting of $rI_n$•ribo$(C_{11-14}U)_n$; $rI_n$•ribo$(C_4U)_n$; $rI_n$•ribo$(C_5U)_n$; $rI_n$•ribo$(C_6U)_n$; $rI_n$•ribo$(C_7U)_n$; $rI_n$•ribo$(C_8U)_n$; $rI_n$•ribo$(C_9U)_n$; $rI_n$•ribo$(C_{10}U)_n$; $rI_n$•ribo$(C_{11}U)_n$; $rI_n$•ribo$(C_{13}U)_n$; $rI_n$•ribo$(C_{14}U)_n$; $rI_n$•ribo$(C_{15}U)_n$; $rI_n$•ribo$(C_{16}U)_n$; $rI_n$•ribo$(C_{17}U)_n$; $rI_n$•ribo$(C_{18}U)_n$; $rI_n$•ribo$(C_{19}U)_n$; $rI_n$•ribo$(C_{20}U)_n$; $rI_n$•ribo$(C_{21}U)_n$; $rI_n$•ribo$(C_{22}U)_n$; $rI_n$•ribo$(C_{23}U)_n$; $rI_n$•ribo$(C_{24}U)_n$; $rI_n$•ribo$(C_{25}U)_n$; $rI_n$•ribo$(C_{26}U)_n$; $rI_n$•ribo$(C_{27}U)_n$; $rI_n$•ribo$(C_{28}U)_n$; $rI_n$•ribo$(C_{29}U)_n$; $rI_n$•ribo$(C_{30}U)_n$; $rI_n$•ribo$(C_{31}U)_n$; $rI_n$•ribo$(C_{32}U)_n$; $rI_n$•ribo$(C_{33}U)_n$; $rI_n$•ribo$(C_{34}U)_n$; $rI_n$•ribo$(C_{35}U)_n$; $rI_n$•ribo$(C_{4-30}U)_n$; $rI_n$•ribo$(C_{14-30}U)_n$; $rI_n$•ribo$(C_{11-14}G)_n$; $rI_n$•ribo$(C_{4-29}G)_n$; $rI_n$•ribo$(C_{30-35}U)_n$; r(Poly I•Poly C)$_n$; and r(Poly A•Poly U)$_n$. As disclosed above, n may have a number of upper and lower values and may be, for example, 40 to 50,000; 50 to 10,000; 60 to 9000; 70 to 8000; 80 to 7000; and 380 to 450.

In any aspect of this disclosure, the effective amount of tdsRNA is a synergistic, therapeutically effective amount.

In any aspect of this disclosure, a combination of the tdsRNA and the checkpoint inhibitor administered provides a synergistic effect in the treatment of the cancer or in the inhibition of the proliferation of tumor cells. This synergistic effect may be selected from the group consisting of: increasing survival of the subject; increasing time of progression of the subject; inhibiting tumor growth; inducing tumor cell death; increasing tumor regression; preventing tumor recurrence; preventing tumor growth; preventing tumor spread; delaying tumor recurrence; delaying tumor growth; delaying tumor spread; and promoting tumor elimination. In any aspect of this disclosure, the effective amount of checkpoint inhibitor is a synergistic, therapeutically effective amount. In other words, the checkpoint inhibitor administered provides an additive or synergistic effect in the treatment of a cancer or an additive or synergistic effect in an inhibition of the proliferation of a tumor.

In any aspect of this disclosure, one additional step which can be performed in any order with the previously disclosed step or steps, further comprises administering to the subject a third compound. The compositions of this disclosure may comprise this third compound also. The third compound may be one or more selected from the group consisting of: a chemotherapeutic drug (an anti-cancer drug); a targeted anti-cancer drug; and a targeted anti-cancer drug comprising an antibody. A targeted anti-cancer drug is any drug designed to attached to a cancer cell. For example, the drug may comprise an antibody, a ligand, or a receptor, a hormone, a nutrient, a biochemical, or a mimic thereof, or a binding part thereof. In a preferred embodiment, the effective amount of third compound is synergistic with the tdsRNA and the checkpoint inhibitor, is a therapeutically effective amount, or both. In another preferred embodiment, the third compound is at a dosage that is sub-therapeutic and has no effect on cancer except in combination with the first compound (i.e., checkpoint inhibitor) and the second compound (tdsRNA).

In any aspect of this disclosure, the method may comprise a further step of administering to the subject a compound selected from the group consisting of: an interferon; interferon mixture; Alferon; and alpha-interferon species. The interferon may be interferon species purified as a mixture of at least seven species of alpha-interferon produced by human white blood cells. The seven species may be, for example, interferon alpha 2; interferon alpha 4; interferon alpha 7; interferon alpha 8; interferon alpha 10; interferon alpha 16; and interferon alpha 17.

In one aspect, the first compound, the second compound, the optional third compound and the optional fourth compound are each different or chemically distinct, from each other compound. That is, for example, one compound cannot be both a first compound and a second compound.

While any method of administration is suitable, in any aspect of this disclosure, administering may be administering intravenously; administering intradermally; administering subcutaneously; administering intramuscularly; administering intranasally; administering intraperitoneally; administering intracranially; administering intravesically; administering orally; or administering topically.

In any aspect of this disclosure, the tdsRNA and the checkpoint inhibitor can be administered at the same time or separately. For example, the tdsRNA and the checkpoint inhibitor may be administered separately at different time intervals, and the tdsRNA (e.g., in the second compound) is administered at a frequency selected from the group consisting of: once a month, once every 3 weeks, once every two weeks, once weekly, twice weekly, 3 times weekly, 4 times weekly, 5 times weekly, 6 times weekly, and daily. As another example, the tdsRNA and the checkpoint inhibitor may be are administered separately but within a time period selected from the group consisting of: 2 months; 1 month; 3 weeks; 2 weeks; 1 week; 3 days; 1 day; 12 hours, 6 hours, 3 hours, 2 hours, 1 hour, and 30 minutes. In any aspect of this disclosure, the second compound comprising tdsRNA may be administered to the subject intravenously one to five times a week at a dosage which will provide on average of about 25-700 milligram per day of tdsRNA for up to one month or longer than one month. For example, the second compound comprising tdsRNA may be administered to the subject one to five times a week at a dosage which will provide on average of about 25-700 milligram per day of tdsRNA continuously for at least one month.

In any aspect of this disclosure, the tdsRNA and the checkpoint inhibitor together can provide a synergistic effect in the treatment of cancer or in an inhibition of the proliferation of tumor cells over the use of tdsRNA alone, checkpoint inhibitor alone, or a sum of tdsRNA alone and checkpoint inhibitor alone.

In any aspect of this disclosure, the checkpoint inhibitor may have at least one characteristic selected from the group consisting of: an antibody; a monoclonal antibody; a humanized antibody; a human antibody; a fusion protein; a PEGylated antibody; a multimeric antibody; an antibody fragment comprising an epitope binding region; and a combination thereof.

In any aspect of this disclosure, the checkpoint inhibitor may inhibit, interact with or bind to a checkpoint protein, a ligand of a checkpoint protein, or a receptor of a checkpoint protein selected from the group consisting of: 2B4; A2aR; B7 family ligand; B7 H3; B7 H4; B and T lymphocyte attenuator (BTLA); BMA; CD112; CD137; CD160; CD2; CD20; CD226; CD27; CD276; CD28; CD30; CD33; CD40; CD47; CD52; CD70; CD80; CD86; CGEN 15049; CHK 1; CHK2; cytotoxic T-lymphocyte antigen-4 (CTLA-4); DR3; galectin 9 (GAL9); GITR; herpesvirus entry mediator (HVEM); ICOS; IDO1; IDO2; Killer-Cell Immunoglobulin-Like Receptor (KIR); LAG3; LAIR; LAIR1; LAIR2; LIGHT; lymphocyte activation gene 3 (LAG-3); MARCO; OX-40; PD-1; PD-L1; PD-L2; PS; SIRP alpha; SLAM; T cell immunoreceptor with Ig and ITIM domains (TIGIT); T cell membrane protein 3 (TIM3); V-domain immunoglobulin (Ig)-containing suppressor of T-cell activation (VISTA); VTCN1; and a combination thereof.

In any aspect of this disclosure, the checkpoint inhibitor may inhibit, interact with or binds to a checkpoint protein a ligand of a checkpoint protein, or a receptor of a checkpoint protein. For example, the checkpoint protein, a ligand of a checkpoint protein, or a receptor of a checkpoint protein, may selected from the group consisting of: PD-1; PD-L1; cytotoxic T-lymphocyte antigen-4 (CTLA-4); CD80; CD86; and a combination thereof. In preferred embodiments, the checkpoint inhibitor inhibits PD-1 or PD-L1. Additional members of this group of checkpoint inhibitor/receptors are listed further in other parts of this disclosure. In one embodiment, the checkpoint inhibitor may comprise an antibody. For example, the checkpoint inhibitor may comprise an antibody that binds to one or more checkpoint protein, a ligand of a checkpoint protein, or a receptor of a checkpoint protein.

In any aspect of this disclosure, the checkpoint inhibitor may be selected from the group consisting of: alemtuzumab (CAMPATH-1H®); AMP-224 (GlaxoSmithKline/Amplimmune); AMP-514 (Amplimmune/AZ); arelumab (Merck Serono); atezolizumab (TECENTRIQ®; Roche/Genentech) [targets PD-L1]; AUNP 12 (Aurigene and Pierre Fabre); avelumab (BAVENCIO®) [targets PD-L1]; BMS-936559 BMS-986016 (Bristol-Meyers Squibb); BMS-986016 (Bristol-Meyers Squibb); cemiplimab (LIBTAYO®) [targets PD-1]; CP-870,893 (Genentech); CT-011; durvalumab (IMFINIZI®); Durvalumab (IMFINZI®) [targets PD-L1]; Galiximab (Biogen Idec); IMP321 (Immutep S.A.); INCB024360 (Incyte); Indoximod (NewLink Genetics); IPH2101 (Innate Pharma/Bristol-Myers Squibb); ipilimumab (YERVOY®, (Bristol-Myers Squibb); Libtayo (cemiplimab-rwlc); lambrolizumab; lirilumab (Bristol-Myers Squibb); MDX-1105 (Medarex, Inc./Bristol Myer Squibb); MEDI-4736 (Medimmune/AstraZeneca); MEDI-6469 (MedImmune/AZ); MGA271 (Macrogenics); MIHI; Mogamulizumab (Kyowa Hakko Kirin); MPDL3280A (Roche); nivolumab (OPDIVO®, Bristol-Myers Squibb) [targets PD-1]; NLG-919 (NewLink Genetics); ofatumumab (ARZERRA®); pembrolizumab (KEYTRUDA®; Merck) [targets PD-1]; PF-05082566 (Pfizer); pidilizumab (Curetech); rituximab (RITUXAN®); tremelimumab; urelumab (Bristol-Meyers Squibb); Varlilumab (CellDex Therapeutics); and a combination thereof.

In any aspect of this disclosure, the subject to be treated may be a mammal. The mammal may be, for example a human.

In any aspect of this disclosure, the cancer may be one that is nonresponsive to treatment by a checkpoint inhibitor alone and/or that is nonresponsive to a chemotherapeutic drug alone and/or that is nonresponsive to a combination of a checkpoint inhibitor and a chemotherapeutic drug.

In another aspect, this disclosure is directed to a method for treating a cancer in a subject in need thereof, the method comprising: exposing or contacting the cancer to a first compound and a second compound in any order together or separately, wherein the first compound comprises an effective amount of a checkpoint inhibitor optionally with at least one pharmaceutically-acceptable carrier, and wherein the second compound is an effective amount of a Therapeutic Double Stranded RNA (tdsRNA) optionally with at least one pharmaceutically-acceptable carrier.

In another aspect, this disclosure is directed to a composition for treating cancer comprising: a checkpoint inhibitor and tdsRNA. The composition may be a pharmaceutical composition further comprising at least one pharmaceutically acceptable carrier. The composition may improve progression free survival or overall survival of a subject administered the composition. In one aspect, the checkpoint inhibitor may be selected from the group consisting of: a monoclonal antibody, a humanized antibody, a fully human antibody, a fusion protein, and a combination thereof. In one aspect, the checkpoint inhibitor may inhibit, binds to or interact with a checkpoint protein, a ligand of a checkpoint protein, or a receptor of a checkpoint protein selected from the group consisting of: 2B4; A2aR; B7 family ligand; B7 H3; B7 H4; B and T lymphocyte attenuator (BTLA); BMA; CD112; CD137; CD160; CD2; CD20; CD226; CD27; CD276; CD28; CD30; CD33; CD40; CD47; CD52; CD70; CD80; CD86; CGEN 15049; CHK 1; CHK2; cytotoxic T-lymphocyte antigen-4 (CTLA-4); DR3; galectin 9 (GAL9); GITR; herpesvirus entry mediator (HVEM); ICOS; IDO1; IDO2; Killer-Cell Immunoglobulin-Like Receptor (KIR); LAG3; LAIR; LAIR1; LAIR2; LIGHT; lymphocyte activation gene 3 (LAG-3); MARCO; OX-40; PD-1; PD-L1; PD-L2; PS; SIRP alpha; SLAM; T cell immunoreceptor with Ig and ITIM domains (TIGIT); T cell membrane protein 3 (TIM3); V-domain immunoglobulin (Ig)-containing suppressor of T-cell activation (VISTA); VTCN1; a ligand thereof; a receptor thereof; and a combination thereof. Preferably, the checkpoint inhibitor may inhibit, bind to, or interact with a checkpoint protein, a ligand of a checkpoint protein, or a receptor of a checkpoint protein selected from the group consisting of: PD-1; PD-L1; cytotoxic T-lymphocyte antigen-4 (CTLA-4); CD80; CD86; a ligand thereof; a receptor thereof; and a combination thereof. For example, the checkpoint inhibitor is selected from the group consisting of: ipilimumab (YERVOY®, (Bristol-Myers Squibb); nivolumab (OPDIVO®, Bristol-Myers Squibb); pembrolizumab (KEYTRUDA®; Merck); and a combination thereof. As another example, the checkpoint inhibitor may be selected from the group consisting of: alemtuzumab (CAMPATH-1H®); AMP-224 (GlaxoSmithKline/Amplimmune); AMP-514 (Amplimmune/AZ); arelumab (Merck Serono); atezolizumab (TECENTRIQ®; Roche/Genentech) [targets PD-L1]; AUNP 12 (Aurigene and Pierre Fabre); avelumab (BAVENCIO®) [targets PD-L1]; BMS-936559 BMS-986016 (Bristol-Meyers Squibb); BMS-986016 (Bristol-Meyers Squibb); cemiplimab (LIBTAYO®) [targets PD-1]; CP-870,893 (Genentech); CT-011; durvalumab (IMFINIZI®); Durvalumab (IMFINZI®) [targets PD-L1]; Galiximab (Biogen Idec); IMP321 (Immutep S.A.); INCB024360 (Incyte); Indoximod (NewLink Genetics); IPH2101 (Innate Pharma/Bristol-Myers Squibb); ipilimumab (YERVOY®, (Bristol-Myers Squibb); Libtayo (cemiplimab-rwlc); lambrolizumab; lirilumab (Bristol-Myers Squibb); MDX-1105 (Medarex, Inc./Bristol Myer Squibb); MEDI-4736 (Medimmune/AstraZeneca); MEDI-6469 (MedImmune/AZ); MGA271 (Macrogenics); MIHI; Mogamulizumab (Kyowa Hakko Kirin); MPDL3280A (Roche); nivolumab (OPDIVO®, Bristol-Myers Squibb) [targets PD-1]; NLG-919 (NewLink Genetics); ofatumumab (ARZERRA®); pembrolizumab (KEYTRUDA®; Merck) [targets PD-1]; PF-05082566 (Pfizer); pidilizumab (Curetech); rituximab (RITUXAN®); tremelimumab; urelumab (Bristol-Meyers Squibb); Varlilumab (CellDex Therapeutics); and a combination thereof.

In any aspect of this disclosure, the anti-cancer drug or chemotherapeutic drug may be at least one selected from the group consisting of: ABVD; AC; ACE; Abiraterone (Zytiga); Abraxane; Abstral; Actinomycin D; Actiq; Adriamycin; Afatinib (Giotrif); Afinitor; Aflibercept (Zaltrap); Aldara; Aldesleukin (IL-2, Proleukin or interleukin 2);

Alemtuzumab (MabCampath); Alkeran; Amsacrine (Amsidine, m-AMSA); Amsidine; Anastrozole (Arimidex); Ara C; Aredia; Arimidex; Aromasin; Arsenic trioxide (Trisenox, ATO); Asparaginase (Crisantaspase, Erwinase); Axitinib (Inlyta); Azacitidine (Vidaza); BEACOPP; BEAM; Bendamustine (Levact); Bevacizumab (Avastin); Bexarotene (Targretin); Bicalutamide (Casodex); Bleomycin; Bleomycin, etoposide and platinum (BEP); Bortezomib (Velcade); Bosulif; Bosutinib (Bosulif); Brentuximab (Adcetris); Brufen; Buserelin (Suprefact); Busilvex; Busulfan (Myleran, Busilvex); CAPE-OX; CAPDX; CAV; CAVE; CCNU; CHOP; CMF; CMV; CVP; Cabazitaxel (Jevtana); Cabozantinib (Cometriq); Caelyx; Calpol; Campto; Capecitabine (Xeloda); Caprelsa; Carbo MV; CarboTaxol; Carboplatin; Carboplatin and etoposide; Carboplatin and paclitaxel; Carmustine (BCNU, Gliadel); Casodex; Ceritinib (Zykadia); Cerubidin; Cetuximab (Erbitux); ChlVPP; Chlorambucil (Leukeran); Cisplatin; Cisplatin and Teysuno; Cisplatin and capecitabine (CX); Cisplatin, etoposide and ifosfamide (PEI); Cisplatin, fluorouracil (5-FU) and trastuzumab; Cladribine (Leustat, LITAK); Clasteon; Clofarabine (Evoltra); Co-codamol (Kapake, Solpadol, Tylex); Cometriq; Cosmegen; Crisantaspase; Crizotinib (Xalkori); Cyclophosphamide; Cyclophosphamide, thalidomide and dexamethasone (CTD); Cyprostat; Cyproterone acetate (Cyprostat); Cytarabine (Ara C, cytosine arabinoside); Cytarabine into spinal fluid; Cytosine arabinoside; DHAP; DTIC; Dabrafenib (Tafinlar); Dacarbazine (DTIC); Dacogen; Dactinomycin (actinomycin D, Cosmegen); Dasatinib (Sprycel); Daunorubicin; De Gramont; Decapeptyl SR; Decitabine (Dacogen); Degarelix (Firmagon); Denosumab (Prolia, Xgeva); Depocyte; Dexamethasone; Diamorphine; Disodium pamidronate; Disprol; Docetaxel (Taxotere); Docetaxel, cisplatin and fluorouracil (TPF); Doxifos; Doxil; Doxorubicin (Adriamycin); Doxorubicin and ifosfamide (Doxifos); Drogenil; Durogesic; EC; ECF; EOF; EOX; EP (Etoposide and cisplatin); ESHAP; Effentora; Efudix; Eldisine; Eloxatin; Enzalutamide; Epirubicin (Pharmorubicin); Epirubicin cisplatin and capecitabine (ECX); Epirubicin, carboplatin and capecitabine (ECarboX); Eposin; Erbitux; Eribulin (Halaven); Erlotinib (Tarceva); Erwinase; Estracyt; Etopophos; Etoposide (Eposin, Etopophos, Vepesid); Everolimus (Afinitor); Evoltra; Exemestane (Aromasin); FAD; FEC; FEC-T chemotherapy; FMD; FOLFIRINOX; FOLFOX; Faslodex; Femara; Fentanyl; Firmagon; Fludara; Fludarabine (Fludara); Fludarabine, cyclophosphamide and rituximab (FCR); Fluorouracil (5FU); Flutamide; Folinic acid, fluorouracil and irinotecan (FOLFIRI); Fulvestrant (faslodex); G-CSF; Gefitinib (Iressa); GemCarbo (gemcitabine and carboplatin); GemTaxol; Gemcitabine (Gemzar); Gemcitabine and capecitabine (GemCap); Gemcitabine and cisplatin (GC); Gemcitabine and paclitaxel (GemTaxol); Gemzar; Giotrif; Gliadel; Glivec; Gonapeptyl Depot; Goserelin (Zoladex); Goserelin (Zoladex, Novgos); Granulocyte colony stimulating factor (G-CSF); Halaven; Herceptin; Hycamtin; Hydrea; Hydroxycarbamide (Hydrea); Hydroxyurea; I-DEX; ICE; IL-2; IPE; Ibandronic acid; Ibritumomab (Zevalin); Ibrutinib (Imbruvica); Ibuprofen (Brufen, Nurofen); Iclusig; Idarubicin (Zavedos); Idarubicin and dexamethasone; Idelalisib (Zydelig); Ifosfamide (Mitoxana); Imatinib (Glivec); Imiquimod cream (Aldara); Imnovid; Instanyl; Interferon (Intron A); Interleukin; Intron A; Ipilimumab (Yervoy); Iressa; Irinotecan (Campto); Irinotecan and capecitabine (Xeliri); Irinotecan de Gramont; Irinotecan modified de Gramont; Javlor; Jevtana; Kadcyla; Kapake; Keytruda; Lanreotide (Somatuline); Lanvis; Lapatinib (Tyverb); Lenalidomide (Revlimid); Letrozole (Femara); Leukeran; Leuprorelin (Prostap, Lutrate); Leustat; Levact; Liposomal doxorubicin; Litak; Lomustine (CCNU); Lynparza; Lysodren; MIC; MMM; MPT; MST Continus; MVAC; MVP; MabCampath; Mabthera; Maxtrex; Medroxyprogesterone acetate (Provera); Megace; Megestrol acetate (Megace); Melphalan (Alkeran); Mepact; Mercaptopurine (Xaluprine); Methotrexate; Methyl prednisolone; Mifamurtide (Mepact); Mitomycin C; Mitotane; Mitoxana; Mitoxantrone (Mitozantrone); Morphgesic SR; Morphine; Myleran; Myocet; Nab-paclitaxel; Nab-paclitaxel (Abraxane); Navelbine; Nelarabine (Atriance); Nexavar; Nilotinib (Tasigna); Nintedanib (Vargatef); Nipent; Nivolumab (Opdivo); Novgos; Nurofen; Obinutuzumab (Gazyvaro); Octreotide; Ofatumumab (Arzerra); Olaparib (Lynparza); Oncovin; Onkotrone; Opdivo; Oramorph; Oxaliplatin (Eloxatin); Oxaliplatin and capecitabine (Xelox); PAD; PC (paclitaxel and carboplatin, CarboTaxol); PE; PMitCEBO; POMB/ACE; Paclitaxel (Taxol); Paclitaxel and carboplatin; Pamidronate; Panadol; Panitumumab (Vectibix); Paracetamol; Pazopanib (Votrient); Pembrolizumab (Keytruda); Pemetrexed (Alimta); Pemetrexed and carboplatin; Pemetrexed and cisplatin; Pentostatin (Nipent); Perjeta; Pertuzumab (Perjeta); Pixantrone (Pixuvri); Pixuvri; Pomalidomide (Imnovid); Ponatinib; Potactasol; Prednisolone; Procarbazine; Procarbazine, lomustine and vincristine (PCV); Proleukin; Prolia; Prostap; Provera; Purinethol; R-CHOP; R-CVP; R-DHAP; R-ESHAP; R-GCVP; RICE; Raloxifene; Raltitrexed (Tomudex); Regorafenib (Stivarga); Revlimid; Rituximab (Mabthera); Sevredol; Sodium clodronate (Bonefos, Clasteon, Loron); Solpadol; Sorafenib (Nexavar); Steroids (dexamethasone, prednisolone, methylprednisolone); Streptozocin (Zanosar); Sunitinib (Sutent); Sutent; TAC; TIP; Tafinlar; Tamoxifen; Tarceva; Targretin; Tasigna; Taxol; Taxotere; Taxotere and cyclophosphamide (TC); Temodal; Temozolomide (Temodal); Temsirolimus; Tepadina; Teysuno; Thalidomide; Thiotepa (Tepadina); Tioguanine (thioguanine, 6-TG, 6-tioguanine); Tomudex; Topotecan (Hycamtin, Potactasol); Torisel; Trabectedin (Yondelis); Trastuzumab (Herceptin); Trastuzumab emtansine (Kadcyla); Treosulfan; Tretinoin (Vesanoid, ATRA); Triptorelin; Trisenox; Tylex; Tyverb; VIDE; Vandetanib (Caprelsa); Vargatef; VeIP; Vectibix; Velbe; Velcade; Vemurafenib (Zelboraf); Vepesid; Vesanoid; Vidaza; Vinblastine (Velbe); Vincristine; Vincristine, actinomycin D (dactinomycin) and cyclophosphamide (VAC); Vincristine, actinomycin and ifosfamide (VAI); Vincristine, doxorubicin and dexamethasone (VAD); Vindesine (Eldisine); Vinflunine (Javlor); Vinorelbine (Navelbine); Vismodegib (Erivedge); Votrient; XELOX; Xalkori; Xeloda; Xgeva; Xtandi; Yervoy; Yondelis; Z-DEX; Zaltrap; Zanosar; Zavedos; Zelboraf; Zevalin; Zoladex (breast cancer); Zoladex (prostate cancer); Zoledronic acid (Zometa); Zometa; Zomorph; Zydelig; Zytiga; and a combination thereof.

The following are preferred, though non-limiting, embodiments of the present disclosure.

1. A checkpoint inhibitor and a Therapeutic Double Stranded (tdsRNA) for use in the treatment of cancer.

2. The checkpoint inhibitor and a tdsRNA for use according to embodiment 1, wherein the tdsRNA and the checkpoint inhibitor are administered at the same time or separately.

3. The checkpoint inhibitor and a tdsRNA for use according to embodiment 1 or 2, further comprising administering to the subject a third compound wherein the third compound is one or more selected from the group consisting of:

a chemotherapeutic drug;
a targeted anti-cancer drug; and
a targeted anti-cancer drug comprising an antibody.

4. The checkpoint inhibitor and a tdsRNA for use according to any one of the preceding embodiments, further comprising administering to the subject one or more selected from the group consisting of: an interferon; interferon mixture; Alferon; and alpha-interferon species.

5. A composition for treating cancer comprising a checkpoint inhibitor and Therapeutic Double Stranded (tdsRNA).

6. The checkpoint inhibitor and a tdsRNA for use or the composition according to any one of the preceding embodiments, wherein the checkpoint inhibitor is selected from:
an antibody; a monoclonal antibody; a humanized antibody; a human antibody; a fusion protein; a PEGylated antibody; a multimeric antibody; an antibody fragment comprising an epitope binding region; and a combination thereof.

7. The checkpoint inhibitor and a tdsRNA for use or the composition according to any one of the preceding embodiments, wherein the checkpoint inhibitor inhibits, interacts with or binds to a checkpoint protein, a ligand of a checkpoint protein, or a receptor of a checkpoint protein selected from the group consisting of: 2B4; A2aR; B7 family ligand; B7 H3; B7 H4; B and T lymphocyte attenuator (BTLA); BMA; CD112; CD137; CD160; CD2; CD20; CD226; CD27; CD276; CD28; CD30; CD33; CD40; CD47; CD52; CD70; CD80; CD86; CGEN 15049; CHK 1; CHK2; cytotoxic T-lymphocyte antigen-4 (CTLA-4); DR3; galectin 9 (GAL9); GITR; herpesvirus entry mediator (HVEM); ICOS; IDO1; IDO2; Killer-Cell Immunoglobulin-Like Receptor (KIR); LAG3; LAIR; LAIR1; LAIR2; LIGHT; lymphocyte activation gene 3 (LAG-3); MARCO; OX-40; PD-1; PD-L1; PD-L2; PS; SIRP alpha; SLAM; T cell immunoreceptor with Ig and ITIM domains (TIGIT); T cell membrane protein 3 (TIM3); V-domain immunoglobulin (Ig)-containing suppressor of T-cell activation (VISTA); VTCN1; and a combination thereof.

8. The checkpoint inhibitor and a tdsRNA for use or the composition according to any one of the preceding embodiments, wherein the checkpoint inhibitor inhibits, interacts with or binds to checkpoint protein, a ligand of a checkpoint protein, or a receptor of a checkpoint protein selected from the group consisting of:
PD-1; PD-L1; cytotoxic T-lymphocyte antigen-4 (CTLA-4); CD80;
CD86; and a combination thereof.

9. The checkpoint inhibitor and a tdsRNA for use or the composition according to any one of the preceding embodiments, wherein the checkpoint inhibitor inhibits PD-1 or PD-L1.

10. The checkpoint inhibitor and a tdsRNA for use or the composition according to any one of the preceding embodiments, wherein the cancer is: pancreatic cancer; skin cancer; colorectal cancer; ovarian cancer; melanoma; breast cancer; triple negative breast cancer; head and neck tumor; bladder cancer; renal cell carcinoma; and lung cancer.

11. The checkpoint inhibitor and a tdsRNA for use or the composition according to any one of the preceding embodiments, wherein the cancer is pancreatic cancer, colorectal cancer, melanoma, bladder cancer, or renal cell carcinoma.

12. The checkpoint inhibitor and a tdsRNA for use or the composition of any one of the preceding embodiments, wherein the tdsRNA is selected from:
$rI_n$•ribo$(C_{11-14}U)_n$; $rI_n$•ribo$(C_4U)_n$; $rI_n$•ribo$(C_5U)_n$; $rI_n$•ribo$(C_6U)_n$;
$rI_n$•ribo$(C_7U)_n$; $rI_n$•ribo$(C_8U)_n$; $rI_n$•ribo$(C_9U)_n$; $rI_n$•ribo$(C_{10}U)_n$;
$rI_n$•ribo$(C_{11}U)_n$; $rI_n$•ribo$(C_{13}U)_n$; $rI_n$•ribo$(C_{14}U)_n$; $rI_n$•ribo$(C_{15}U)_n$;
$rI_n$•ribo$(C_{16}U)_n$; $rI_n$•ribo$(C_{17}U)_n$; $rI_n$•ribo$(C_{18}U)_n$; $rI_n$•ribo$(C_{19}U)_n$;
$rI_n$•ribo$(C_{20}U)_n$; $rI_n$•ribo$(C_{21}U)_n$; $rI_n$•ribo$(C_{22}U)_n$; $rI_n$•ribo$(C_{23}U)_n$;
$rI_n$•ribo$(C_{24}U)_n$; $rI_n$•ribo$(C_{25}U)_n$; $rI_n$•ribo$(C_{26}U)_n$; $rI_n$•ribo$(C_{27}U)_n$;
$rI_n$•ribo$(C_{28}U)_n$; $rI_n$•ribo$(C_{29}U)_n$; $rI_n$•ribo$(C_{30}U)_n$; $rI_n$•ribo$(C_{31}U)_n$;
$rI_n$•ribo$(C_{32}U)_n$; $rI_n$•ribo$(C_{33}U)_n$; $rI_n$•ribo$(C_{34}U)_n$; $rI_n$•ribo$(C_{35}U)_n$; $rI_n$•ribo$(C_{4-30}U)_n$; $rI_n$•ribo$(C_{14-30}U)_n$; $rI_n$•ribo$(C_{11-14}G)_n$; $rI_n$•ribo$(C_{4-29}G)_n$;
$rI_n$•ribo$(C_{30-35}U)_n$; r(Poly I•Poly C)$_n$; r(Poly A•Poly U)$_n$; and Rugged dsRNA.

13. The checkpoint inhibitor and a tdsRNA for use or the composition according to any one of the preceding embodiments, wherein the tdsRNA is $rI_n$•ribo$(C_{4-29}U)_n$ or $rI_n$•ribo $(C_{30-35}U)_n$, preferably $rI_n$•ribo$(C_{4-29}U)_n$.

14. The checkpoint inhibitor and a tdsRNA for use or the composition according to any one of the preceding embodiments, wherein the tdsRNA is $rI_n$•ribo$(C_{11-14}U)_n$.

15. The checkpoint inhibitor and a tdsRNA for use according to embodiment 12, wherein the tdsRNA is $r(I_n)$•ribo$(C_{12}U)_n$ or $r(I_n)$•ribo$(C_{30}U)_n$.

16. The checkpoint inhibitor and a tdsRNA for use a or the composition according to any one of the preceding embodiments, wherein the tdsRNA is $r(I_n)$•ribo$(C_{12}U)_n$.

17. The checkpoint inhibitor and a tdsRNA for use or the composition according to any one of the preceding embodiments, wherein the tdsRNA is Rugged dsRNA, wherein the Rugged dsRNA is resistant to denaturation under conditions that are able to separate hybridized poly(riboinosinic acid) and poly(ribocytosinic acid) strands ($rI_n$•$rC_n$).

18. The checkpoint inhibitor and a tdsRNA for use or the composition according to any one of the preceding embodiments, wherein n is an integer selected from 40 to 50,000; 50 to 10,000; 60 to 9000; 70 to 8000; 80 to 7000; or 380 to 450.

19. The checkpoint inhibitor and a tdsRNA for use or the composition according to any one of the preceding embodiments, wherein the tdsRNA and the checkpoint inhibitor together provide a synergistic effect in the treatment of cancer or in an inhibition of the proliferation of tumor cells over the use of tdsRNA alone, checkpoint inhibitor alone, or a sum of tdsRNA alone and checkpoint inhibitor alone.

BRIEF DESCRIPTION OF THE DRAWINGS

FIG. 1 Depicts the synergism between tdsRNA and checkpoint blockade in an animal model of pancreatic cancer showing synergistic increase in time to progression and synergistic increase in overall survival.

FIG. 8 Survival of Renal Cell Carcinoma (786-0) in Nude Mice Treated with AMPLIGEN. Depicts 100% survival of nude mice bearing renal cell carcinoma (786-0) xenografts treated with tdsRNA (very top line) compared to 100% death rate for untreated controls.

DETAILED DESCRIPTION

Figure 2:
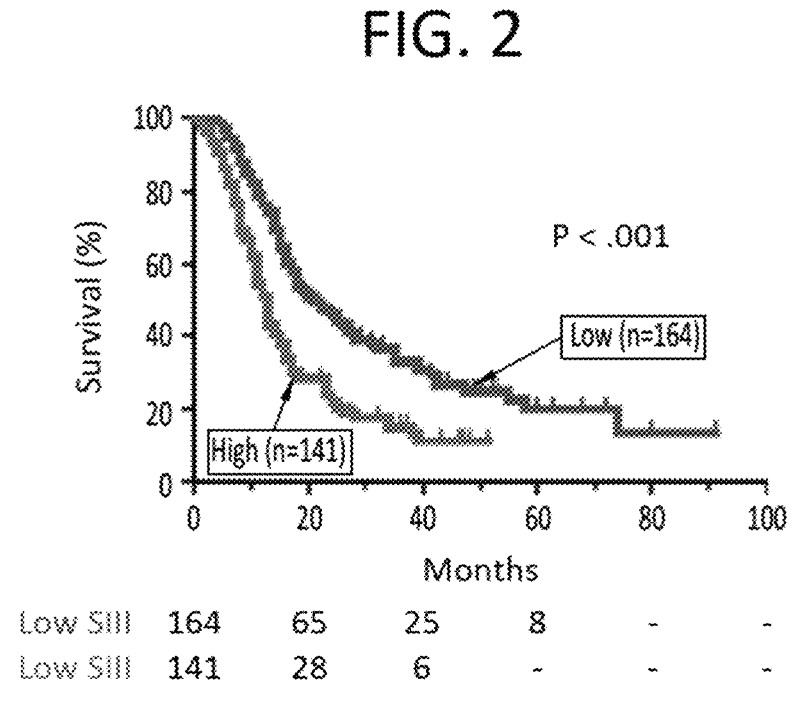
FIG. 2 Depicts the survival of patients with pancreatic cancer with low SIII or high SIII.

Immunotherapy comprising a variety of specific indications are being rapidly approved currently by the FDA for checkpoint inhibitors (monoclonal antibodies which block either T-cell or tumor cell inhibitors of immune elimination).

Nonlimiting Examples of Specific Cancer Types in Need of Improved Immunotherapy As used herein, "tumors" and "cancers" are used interchangeably. Tumors may be benign or malignant.

Pancreatic Cancer

Pancreatic cancer is the fourth most common cause of cancer-related deaths in the United States and the eighth most common worldwide. It has one of the highest fatality rates of all cancers and is the fourth highest cancer killer among men and women. For all stages combined, the 1- and 5-year relative survival rates are shockingly low: 25% and 6%, respectively. For local disease, the 5-year survival rate is approximately 20%. The median survival rates for locally advanced and metastatic diseases, which collectively represent over 80% of individuals, are about 10 and 6 months, respectively.

Treatment of pancreatic cancer depends on the stage of cancer. Although only localized cancer is considered suitable for surgery with curative intent at present, only about 20% of cases present with localized disease at diagnosis. Surgery can also be performed for palliation if the malignancy is invading or compressing the duodenum or colon. In such cases, bypass surgery might overcome the obstruction and improve quality of life but is not intended as a cure. For a disease that is deemed not suitable for resection, palliative chemotherapy may be used to improve the quality of life and gain a modest survival benefit for the patient.

There is a need for improved methods for treating pancreatic cancer, in particular, locally advanced and metastatic pancreatic cancer. Metastasis is the leading cause of mortality in cancer patients. However, there are no effective therapies to target the development and progression of metastases in pancreatic cancer. In one of the preferred embodiments of the disclosure, the cancer is pancreatic cancer.

Melanoma

Globally, melanoma is diagnosed with an incidence rate of 3.0 in 100,000, representing 1.7% of all cancer cases. In 2012, 232,000 women were diagnosed with melanoma. The mortality rate of 0.7 in 100,000 women is substantially lower than the incidence rate (Ferlay et al., 2013). The lifetime risk of getting melanoma is about 2.4% (1 in 40) for Caucasians, 0.1% (1 in 1,000) for African-Americans, and 0.5% (1 in 200) for Hispanics. Although the average age at melanoma diagnosis is 62, it is one of the most common cancers in young adults (especially young women) (American Cancer Society, 2015).

For patients with localized melanoma, the prognosis is good with adequate surgical excision, which is reflected in a relatively low mortality rate (World Cancer Report, 2014). The 5-year survival rate is more than 90% and 80% for stage I and II lesions, respectively (Kaufman et al., 2013).

Metastatic melanoma is, however, largely resistant to current therapies (World Cancer Report, 2014). The 5-year survival rate is 78-40% for stage IIIA-C and 15-20% for stage IV (American Cancer Society, 2015).

Besides sun-exposure, the risk to develop melanoma is influenced by other environmental factors such as age and sex as well as anatomical location and individual susceptibility. Ultraviolet-emitting tanning devices also increase the risk of malignant melanoma. In 20-40% of people with melanoma in their family history, CDKN2A mutations have been found (World Cancer Report, 2014).

Melanomas occur primarily in the skin—more than 95% of cases—but are also found in the mucous membranes of the mouth, nose, anus, and vagina and, to a lesser extent, the intestine. Furthermore, melanocytes are present in the conjunctiva, the retina, and the meninges. Melanoma can be subtyped histologically into superficial spreading melanoma, nodular melanoma, acral lentiginous melanoma, and lentigo maligna melanoma. Melanomas are classified according to the TNM classification. As recommended in the American Joint Committee on Cancer staging manual, melanoma patients are categorized into three groups: a localized disease with no evidence of metastases (stage I-II), a regional disease (stage III), and distant metastatic disease (stage IV) (World Cancer Report, 2014).

The standard therapy in melanoma is complete surgical resection with surrounding healthy tissue. If resection is not complete or not possible at all, patients receive primary radiation therapy, which can be combined with interferon-alpha administration in advanced stages (stages IIB/C and IIIA-C). Therapeutic options include mono-chemotherapy, poly-chemotherapy, and targeted therapies with specific inhibitors. Dacarbazine, temozolamide, and fotemustin are currently used in mono-chemotherapy trials. Different combinations of chemotherapeutics are investigated in poly-chemotherapy studies: the CarboTax regimen (carboplatin plus paclitaxel), the GemTreo regimen (gemcitabine plus treosulfan), the DVP regimen (dacarbazine plus vindesin plus cisplatin), the BHD regimen (carmustine plus hyroxyurea plus dacarbazine), and the BOLD regimen (bleomycin plus vincristine plus lomustine plus darcarbazine). Furthermore, chemotherapy in combination with ipilimumab and the administration of specific BRAF, c-KIT, and N-RAS inhibitors to patients with mutations within the respective genes are being evaluated in clinical trials (S3-Leitlinie Melanom, 2013). In one of the preferred embodiments of the disclosure, the cancer is melanoma.

Colorectal Cancer (CRC)

Colorectal cancer (CRC) is one of the most common cancers in the world. Early detection and surgery with excision of the tumor are currently of critical importance for successful treatment. For localized tumors, i.e., tumors that have not evolved into a metastasizing disease, surgical intervention with radical resection of the tumor and surrounding bowel and tissues is performed. Colorectal tumors are categorized into several stages according to Dukes' stages A-D or more recently, according to the TNM classification. Early-stage tumors (Dukes' stages A and B) are generally associated with a relatively favorable outcome, while later-stage tumors, presenting with metastasis (Dukes' stage C and D) have poor survival rates. Unfortunately, metastasis often goes undetected until the tumor has grown to a considerable size. The tumor typically metastasizes to regional lymph nodes, but distant metastasis to the liver and lung are also common.

Patients with early-stage CRC (Stage I and II or Dukes' A and B) undergo surgical resection only and are not treated chemotherapeutically. Almost one-fourth of early-stage patients with non-metastatic disease, however, relapse with metastasis later, Patients diagnosed with metastatic forms of CRC, namely Dukes' C with lymph node metastasis and Dukes' D with hematological dissemination, have five-year survival rates of 37% and 11%, respectively. Patients diagnosed at an early stage (Dukes' A and B) with no evidence of metastatic disease at the time of surgery have a significantly better prognosis having five-year survival rates of 85% and 67%, respectively (Cancer Research UK, 2004). However, a significant proportion of these patients (10%-45%) relapse with metastatic disease.

Chemotherapy has proven effective for Dukes' stage C tumors. Newer studies also indicate the value of chemotherapy for some patients with early colorectal cancer at risk of metastatic relapse. However, although chemotherapeutic intervention has been implemented for some patients with early colon cancer, its implementation as a routine treatment is not cost-effective and can be counterproductive. The side effects associated with the treatment make it desirable to avoid the use of chemotherapy except in cases of high relapse risk. In one of the preferred embodiments of the disclosure, the cancer is colorectal cancer.

Ovarian/Endometrial Cancer

Ovarian cancer is among the most lethal gynecologic malignancies in developed countries. In the United States, approximately 23,000 women are diagnosed with the disease and almost 14,000 women die from it each year. There are three main types of ovarian cancer: epithelial cancer, germ cell cancer, and sex cord stromal cancer. About 90% of ovarian cancers start in the epithelial tissue (the lining of the outside of the ovary). This type of ovarian cancer is divided into serous, mucinous, endometrioid, clear cell, transitional, and undifferentiated types. The risk of epithelial ovarian cancer increases with age, especially after the age of 50. Germ cell tumors account for about 5% of ovarian cancers. They begin in the egg-producing cells. This type of ovarian cancer can occur in women of any age, but about 80% are found in women under the age of 30. The main subtypes are teratoma, dysgerminoma, endodermal sinus tumor, and choriocarcinoma. Sex cord stromal tumors, about 5% of ovarian cancers, grow in the connective tissue of the ovary. Most are found in older women. Despite progress in cancer therapy, ovarian cancer mortality has remained virtually unchanged over the past two decades. Given the steep survival gradient relative to the stage at which the disease is diagnosed, early detection remains the most important factor in improving the long-term survival of ovarian cancer patients.

Endometrial cancer is the most common gynecologic malignancy and accounts for about 13% of all malignancies occurring in women. There are about 34,000 cases of endometrial cancer diagnosed in the United States each year. All endometrial carcinomas arise from the glands of the lining of the uterus. Adenocarcinoma accounts for 75% of all endometrial carcinoma. Endometrial adenocarcinomas that contain benign or malignant squamous cells are known as adenocanthomas and adenosquamous carcinomas respectively and account for 30% of endometrial cancers. The remaining types of endometrial carcinoma have a poorer prognosis. About 3% have a clear cell carcinoma morphology, and about 1% have a papillary carcinoma morphology.

Ovarian cancer refers to at least a cancer or cancers which is one or more selected from the group consisting of serous ovarian cancer, mucinous ovarian cancer, endometrioid ovarian cancer, clear cell ovarian cancer, transitional ovarian cancer and/or undifferentiated ovarian cancer, teratoma, dysgerminoma, endodermal sinus tumor, and choriocarcinoma, endometrial cancer includes, endometrial carcinomas, adenocarcinoma, endometrial adenocarcinomas, adenocanthomas, adenosquamous carcinomas, clear cell carcinoma, and papillary carcinomas. In one of the preferred embodiments of the disclosure, the cancer is ovarian cancer.

Breast Cancer

Breast cancer is a heterogeneous malignant disease exhibiting diverse biological characteristics and clinical responses. Gene expression profiling has defined genetic signatures corresponding to at least five distinct molecular subtypes of breast cancer, including an aggressive form known as triple-negative (TN) breast cancer.

There are three endogenous molecules that have been identified which promote many breast cancers: estrogen receptor (ER), progesterone receptor (PR), and human epidermal growth factor receptor 2 (HER2). By definition, Triple Negative (TN) breast cancer fails to express these three molecules. Although TN breast cancer represents a relatively small percentage of all breast cancers (about 10%), it is a typically high grade (poorly differentiated) and rapidly progressive, with a higher risk of relapse and lower survival than other subtypes of breast cancer. Therefore, TN breast cancer is associated with a disproportionate number of deaths. Additionally, for unknown reasons, TN breast cancer is often diagnosed in younger women and women of African-American descent. Women carrying mutant BRCA1 or BRCA 2 germline genes are at high risk for the development of both breast and ovarian cancer.

Current clinical approaches for breast cancer typically include agents that target the three molecules identified to promote many breast cancers, such as endocrine therapies and the monoclonal antibody trastuzumab targeting HER2. Because TN breast cancer is defined as the absence of these targets, conventional cytotoxic chemotherapy is currently the mainstay systemic treatment for patients with TN breast cancer. However, conventional systemic treatments are limited by the poor therapeutic response, high toxicity, and the development of resistance. Although new approaches in the treatment of TN breast cancer such as targeting DNA repair with PARP inhibitors have emerged, there have been relatively fewer therapeutic advances in TN breast cancer when compared to other subtypes of the disease. Thus, there is a pressing need for targeted approaches toward the treatment of TN breast cancer. In one of the preferred embodiments of the disclosure, the cancer is breast cancer.

Bladder Cancer

Bladder cancer, also known as urothelial carcinoma (transitional cell carcinoma), is a type of cancer that is found in the lining of the urinary tract including the pelvis, ureters, bladder, and parts of the urethra. The most common form of bladder cancer is urothelial carcinoma. Bladder cancer occurs in people of all races and can affect people of any age. Bladder cancer is the fourth most common type of cancer in men and the ninth most common cancer in women. Bladder cancer is responsible for approximately 170,000 deaths per year in the United States.

While scientists do not know the exact cause(s) of bladder cancer, tobacco is believed to be the main known contributor. Occupational exposure in the workplace to carcinogens, such as benzidine (i.e., aromatic amines), can also result in bladder tumors. Occupations at risk for exposure to benzidine are bus drivers, rubber workers, motor mechanics, leather workers, blacksmiths, machine setters, mechanics, and hairdressers—because of the frequent exposure to permanent hair dyes. One other modifiable factor that is less strongly associated with bladder cancer is obesity.

Bladder cancer or urothelial carcinoma is often described based on how far they have invaded the wall of the bladder. Papillary carcinomas, or non-invasive bladder cancer, grow in slender, finger-like projections from the inner surface of the bladder toward the hollow center. Papillary tumors often grow toward the center of the bladder without growing into the deeper bladder layers. Low-grade (slow-growing), non-invasive papillary cancer tends to have a good outcome. Flat carcinomas are another example of non-invasive bladder cancer. Flat carcinomas do not grow toward the hollow part of the bladder. If either a papillary or flat tumor grows into deeper layers of the bladder, it is called an invasive urothelial carcinoma. Invasive bladder cancers are more likely to spread and are much harder to treat.

Other cancers of the bladder are squamous cell carcinoma, adenocarcinoma, small cell carcinoma, and sarcoma.

Current treatment of bladder cancer involves invasive surgery, radical cystectomy, intravesical therapy, chemotherapy, radiation therapy and/or immunotherapy. However, these treatments are replete with drawbacks such as flu-like symptoms, extreme fatigue, hair-loss, DNA damage, development of secondary cancer, cell migration into the bloodstream, and complications from surgery. In one of the preferred embodiments of the disclosure, the cancer is bladder cancer.

Kidney Cancer

Kidney cancer (also referred to as renal cancer or renal cell carcinoma) mostly affects adults between 50 and 70 years of age. If detected early, kidney cancer is curable. However, symptoms may not appear until the tumor has grown to a large size or metastasized to other organs, at which point treatment is palliative.

In this disclosure, renal cancer and kidney cancer refer to renal cell carcinoma.

The 5-year survival rate for individuals diagnosed with kidney cancer is about 90% for those individuals whose tumor is confined to the kidney, about 60% if it has limited spread to nearby tissues, and about 9% if it has spread to distant sites (American Cancer Society, Detailed Guide: Kidney Cancer. “What Are the Key Statistics for Kidney Cancer (Renal Cell Carcinoma)?”).

The majority of kidney cancers are renal cell carcinomas (which account for over 90% of malignant kidney tumors), also known as renal adenocarcinomas or clear cell carcinomas. There are five main types of renal cell carcinoma that are identified based on microscopic examination of cell type: clear cell, papillary, chromophobe, collecting duct, and “unclassified.” Kidney cancers are also usually graded on a scale of 1 through 4 to indicate how similar the nuclei of the cancer cells are to the nuclei of normal kidney cells (grade 1 renal cell cancers have cell nuclei that differ very little from normal kidney cell nuclei and generally have a good prognosis, whereas grade 4 renal cell cancer nuclei appear as undifferentiated as distinguished from differentiated normal kidney cell nuclei and have a worse prognosis). In addition to grade, kidney cancers are also characterized by stage, which describes the size of cancer and degree of metastasis. The most commonly used staging system is that of the American Joint Committee on Cancer (AJCC) (also referred to as the TNM system), although the Robson classification is an older system that may be occasionally used.

Risk factors for kidney cancer include the following: age older than 50 years; male (men are twice as likely to get kidney cancer compared to women); cigarette smoking; exposure to asbestos, cadmium, or organic solvents; obesity; a high-fat diet; and von Hippel-Lindau disease (a genetic condition that has a high incidence of kidney cancer).

Symptoms of kidney cancer include hematuria (blood in the urine), abdominal or low back pain, weight loss, fatigue, anemia, fever, high blood pressure, and leg or ankle swelling.

In addition to a detailed medical history, physical examination, and laboratory blood testing, diagnosis of kidney cancer may typically include a computed tomography (CT) scan, ultrasound, magnetic resonance imaging (MRI), intravenous pyelography (a kidney test that utilizes dye and x-rays), or arteriography (a test in which dye is applied to the blood vessels feeding the kidney). To detect metastatic disease, chest X-ray and bone scan are commonly implemented.

Treatment of kidney cancer in individuals whose tumor is confined to the kidney may involve surgical removal of the kidney (nephrectomy) and surrounding tissue. Radiation therapy may be applied to treat pain and advanced or metastatic kidney cancers or to help shrink a tumor that is causing obstruction. Immunotherapy, such as interferon and interleukin-2, may be used to boost the immune system in patients with advanced kidney cancer (Journal of the American Medical Association, JAMA Patient Page: Kidney Cancer). In one of the preferred embodiments of the disclosure, the cancer is kidney cancer.

Lung Cancer

Lung cancer is the leading cause of cancer death in the United States. Lung cancer is categorized as either non-small cell lung carcinoma (NSCLC) or small cell lung carcinoma, with NSCLC representing more than 80% of cases. For the most common type of lung cancer, non-small cell lung cancer (NSCLC), the five-year survival rate is 70-80% for stage I disease without nodal or distant metastasis, but only 5-15% for advanced Stage IV (distant) disease.

Current treatments for lung cancer include surgery, radiation, classical chemotherapeutic agents (platinum compounds, taxanes), and targeted therapies (inhibitors of VEGFR, EGFR, IGFR, HDACS, and the proteasome). However, despite advances in treatment, five-year survival rates are about 16%. Numerous clinical trials evaluating classical chemotherapy drugs for lung cancer indicate that a therapeutic plateau with current drugs may have been reached. Therefore, there is a need for new drugs for the treatment of lung cancers that have different mechanisms of action. In one of the preferred embodiments of the disclosure, the cancer is lung cancer.

Checkpoint Inhibitors

One area of study on expanding the effects of immunotherapy drugs is the category of checkpoint inhibitors. The term “immune checkpoint inhibitor”, as used herein, refers to a substance that blocks the activity of molecules involved in attenuating the immune response. Examples of immune checkpoint inhibitors are described in this disclosure. Checkpoint inhibitors, in one aspect, are antibody-based agents that mobilize the immune T-cell response. Checkpoint inhibitors block cancer cells' use of molecular switches known as checkpoints that normally prevent T cells from attacking healthy tissues. When these checkpoints, such as PD-1 (programmed death 1) and CTLA4 (cytotoxic T-lymphocyte-associated protein 4), are hijacked by cancer cells, the immune system's T-cell response is switched off, allowing the cells to multiply and the tumors to grow. Checkpoint inhibitors (e.g., anti-PD-1, anti-CTL4, anti-PDL-1 (programmed death ligand 1 expressed on the surface of tumor cells), and anti-PDL-2) flip the switch back on, freeing the immune response so that T cells are activated and destroy the cancer cells.

Checkpoint inhibitors work best against so-called hot tumors. Hot tumors are cancers that have been invaded by T cells and macrophages, creating an inflamed tumor. This response by the immune army hasn't killed the tumor, but because T cells are present within the tumor, they are more easily mobilized against cancer. Checkpoint inhibitors release the inhibitions the tumor has clamped on the T cells. Once the T cells are free of inhibition, they can freely kill the cancer cells.

Tumors can be classified as "hot" or "cold" depending on the functional capacity of cells within the tumor microenvironment to mount a cytotoxic immune response against the tumor. Hot tumors are populated by cytotoxic T-cells and often have a high mutational load. That is, they have many changes in their DNA code that cause the cancer cells to produce distinctive new proteins called "neoantigens" expressed on their cell surface. These neoantigens make the tumor more prone to recognition by the immune system, and thus more likely to provoke a strong immune response.

"Cold" tumors, by contrast, are cancers that, for various reasons, haven't been recognized or haven't provoked a strong tumor cytotoxic response by the immune system. Immune T cells may have been unable to penetrate the tumor microenvironment. The microenvironment in and around tumor cells comprises blood vessels, structural elements, and specialized immune cells; the latter include myeloid-derived suppressor cells and regulatory T cells (abbreviated as Tregs). These Tregs turn down the intensity of the normal immune response by secreting immunosuppressive chemical messengers like cytokines that impede the movement of cytotoxic T cells (T effector abbreviated as $T_{eff}$) into the tumor resulting in the "immune desert" comprising a cold tumor.

This inability to suppress cold tumors is one of the limitations of current immunotherapy. There is a long-felt need to effectively apply immunotherapy to cancers that are immunologically cold. In other words, how to make immunologically cold cancers immunoresponsive.

Current checkpoint inhibitor therapies, however, are effective at treating cancer in a relatively small population of cancer subject population, which is in part due to pre-existing immune activation and presence of the inhibitory receptors. Accordingly, there is a need to develop methods and combination therapies to initiate or enhance the effectiveness of the checkpoint inhibitors in both the nonresponding subject population and the responding subject population.

Therapeutic Double Stranded RNA (tdsRNA; Previously Called Anti-Tumor Immune Enhancer or ATIE)

This disclosure is directed in part to tdsRNA which was previously named Anti-Tumor Immune Enhancer (ATIE). Specific embodiments of tdsRNA includes AMPLIGEN® (also called rintatolimod), rugged dsRNA, a mismatched dsRNA or dsRNA. The names Therapeutic Double Stranded RNA or tdsRNA is the new name and replaces the old names Anti-Tumor Immune Enhancer or ATIE. ATIE and tdsRNA have the same exact meaning in this disclosure and can be used interchangeably. tdsRNA (formerly known as ATIE) is described below in more detail.

For this disclosure, tdsRNA or ATIE may refer to any dsRNA discussed in this disclosure and especially for any dsRNA disclosed in this section.

One preferred embodiment of tdsRNA is AMPLIGEN® and is as follows: AMPLIGEN® (Poly I:Poly $C_{12}U$) is a synthetic double-stranded ribonucleic acid in which uridylic acid (U) substitution in the cytidylic chain creates a region of non-hydrogen bonding in the molecular configuration. The chemical name is polyriboinosinic:polyribocytidylic (12:1)uridylic acid or Poly I:Poly $C_{12}U$. The USAN (United States Adopted Names) name for AMPLIGEN® is rintatolimod. It follows that AMPLIGEN® and rintatolimod have the same meaning in this disclosure.

Poly I:Poly $C_{12}U$ is a structural analog of the polyribonucleotide complex consisting of polyriboinosinic acid hydrogen-bonded with polyribocytidylic acid, Poly I:Poly C. In the Poly C strand, uridylic acid substitutions occur on an average of every 12 to 13 bases, producing a duplex Poly I:Poly $C_{12}U$, containing specifically configured regions interspersed with uninterrupted regions. The single-stranded RNA (ssRNA) raw materials, Poly I and Poly $C_{12}U$, are annealed under controlled conditions to form the double-stranded RNA (dsRNA), rintatolimod (Poly I:Poly $C_{12}U$), molecules.

In one embodiment the tdsRNA comprises mismatched dsRNA such as:

- an RNA strand comprising riboinosinic acid and an RNA strand comprising ribocytidylic acid and ribouracilic acid, or
- an RNA strand comprising riboinosinic acid and an RNA strand comprising ribocytosinic acid and guanine, or matched dsRNA such as:

- an RNA strand comprising adenine and an RNA strand comprising ribouracilic acid.

Another embodiment(s) of tdsRNA is a specific type of mismatched dsRNA. In one aspect, the mismatched dsRNA may be of the general formula $rI_n \cdot r(C_{4\text{-}35}U)_n$ or $rI_n \cdot r(C_{11\text{-}14}U)_n$, which is preferably $rI_n \cdot r(C_{11}U)_n$; $rI_n \cdot r(C_{13}U)_n$; $rI_n \cdot r(C_{14}U)_n$ and most preferably $rI_n \cdot r(C_{12}U)_n$. The formula $rI_n \cdot r(C_{11\text{-}14}U)_n$ represents a double-stranded RNA with one strand being represented by $rI_n$ and the other strand represented by $(C_{11\text{-}14}U)_n$, wherein the dot symbol "•" represents that the two strands are hybridized to form a double-stranded RNA structure. It should be noted that while we referred to the two strands being hybridized, not 100% of the bases form base pairing as there are mismatches.

$rI_n$ represents polyriboinosine of n bases. "r" represents the RNA-like form of inosine which is riboinosine. This is as opposed to 2'-deoxyinosine. n represents the total length of this single-stranded inosine molecule—a single-stranded RNA.

For example, $r(C_{11\text{-}14}U)_n$ represents a single-stranded RNA which comprises C bases and U bases with the ratio of C bases to U bases being for every eleven to fourteen C there is a single U. "n" represents the total length, in bases, of this single-stranded RNA.

$rI_n \cdot r(C_{11}\text{-}14U)_n$, therefore, represents a double-stranded RNA with $rI_n$ hybridized to $r(C_{11\text{-}14}U)_n$. Since n represents the length for both strands, both strands of ssRNA are the same length which gives rise to a dsRNA with no significant single-stranded regions in the middle or at the end of the double-stranded structure.

In this disclosure, absent indications otherwise, all the polynucleotides administered to a patient are dsRNA or chemical analogs thereof such as riboinosine (i.e., RNA and not DNA unless otherwise indicated). "n" is the length of the dsRNA (in bases) and n is an integer having a value of from 40 to 50,000; 10 to 40,000; 10 to 500; 10 to 50 or 40-500 (rugged dsRNA). In this and the other formulas that follow r=ribo and rI=riboinosine.

Rugged dsRNA is a tdsRNA that is resistant to denaturation under conditions that are able to separate hybridized poly(riboinosinic acid) and poly(ribocytosinic acid) strands ($rI_n$•rCn). See, U.S. Pat. Nos. 8,722,874 and 9,315,538 for a further description of Rugged dsRNA and exemplary methods of preparing such molecules. In the preferred embodiments of Rugged dsRNA, the Rugged dsRNA has a formula selected from the group consisting of:

- $rI_n$•ribo$(C_{4-29}U)_n$;
- $rI_n$•ribo$(C_{11-14}U)_n$;
- $rI_n$•ribo$(C_{12}U)_n$; and
- $rI_n$•ribo$(C_{30-35}U)_n$. Preferably, Rugged dsRNA has the structure $rI_n$•ribo$(C_{30-35}U)_n$.

In preferred embodiments, Rugged dsRNA has one or more of the following characteristics:

- between 30 to 38 helical turns of duplexed RNA;
- a molecular weight of 250 kilodaltons to 320 kilodaltons;
- each strand of the Rugged dsRNA is about 380 to 450 bases in length—or about 380 to 450 of double stranded basepairs in length.

Under analytical or preparative high performance liquid chromatography, Rugged dsRNA can be isolated from a preparation to produce poly(I):poly$(C_{12}U)_n$ (e.g., poly(I): poly$(C_{11-14}U)_n$) as a substantially purified and pharmaceutically-active molecule with an HPLC peak of about 4.5 to 6.5 minutes, preferably between 4.5 and 6 minutes and most preferably 5 minutes. In some embodiments, the molecular weight is from about 30 kilodaltons to 300 kilodaltons and is about 50 to 500 base pairs in length with about 4.7 to 46.7 complete turns of the RNA helix. Rugged dsRNA represents a molecular species uniquely resistant to denaturation and unfolding. It can be characterize as a dsRNA that is more resistant to denaturation than a r(Poly I•Poly C)$_n$ of the same length; or as a poly(I):poly$(C_xU)_n$ with a HPLC peak of about 5 minutes.

Other mismatched dsRNAs for use in the present invention are based on co-polynucleotides such as poly $(C_m,U)$ or poly $(C_m,G)$ in which m is an integer having a value of from 4 to 29 and are mismatched analogs of complexes of polyriboinosinic and polyribocytidylic acids, formed by modifying $rI_n$•$rC_n$ to incorporate unpaired bases (uracil (U) or guanine (G)) within the polyribocytidylate ($rC_m$) strand. Alternatively, the dsRNA may be derived from r(I)•r(C) dsRNA by modifying the ribosyl backbone of polyriboinosinic acid ($rI_n$), e.g., by including 2'-O-methyl ribosyl residues. The mismatched dsRNA may be complexed with an RNA-stabilizing polymer such as lysine carboxy methyl cellulose, or poly ICLC as described in the next paragraph. Of these mismatched analogs of $rI_n$•rCn, the preferred ones are of the general formula $rI_n$•r$(C_{11-14}, U)_n$ and are described by Ts'o & Carter in U.S. Pat. Nos. 4,024,222 and 4,130,641; the disclosures of which are hereby incorporated by reference. The dsRNAs described therein are generally suitable for use according to the present invention.

Another aspect relates to specifically configured dsRNA derived from ribo(I).ribo(C) dsRNA by modifying the ribosyl backbone of poly(riboinosinic acid) ribo(In), e.g., by including 2'-O-methylribosyl residues. Specifically configured dsRNA may also be modified at the molecule's ends to add a hinge(s) to prevent slippage of the base pairs, thereby conferring a specific bioactivity in solvents or aqueous environments that exist in human biological fluids. The specifically configured dsRNA described in U.S. Pat. Nos. 4,024,222; 4,130,641; and 5,258,369 (incorporated by reference) are generally suitable as starting materials after selection for rugged dsRNA. While this disclosure describes Rugged dsRNA, the other dsRNAs described in this disclosure (including tdsRNA) which are not Rugged dsRNA are still suitable starting material for the production of Rugged dsRNA. In any embodiment, tdsRNA, including Rugged dsRNA, may be complexed with a stabilizing polymer such as polylysine, polylysine plus carboxymethylcellulose, polyarginine, polyarginine plus carboxymethylcellulose, or any combination thereof.

Other examples of mismatched dsRNAs for use as tdsRNA include:

- $rI_n$•ribo$(C_4U)_n$, ratio of C to U in one strand is 4:1;
- $rI_n$•ribo$(C_5U)_n$, ratio of C to U in one strand is 5:1;
- $rI_n$•ribo$(C_6U)_n$, ratio of C to U in one strand is 6:1;
- $rI_n$•ribo$(C_7U)_n$, ratio of C to U in one strand is 7:1;
- $rI_n$•ribo$(C_8U)_n$, ratio of C to U in one strand is 8:1;
- $rI_n$•ribo$(C_9U)_n$, ratio of C to U in one strand is 9:1;
- $rI_n$•ribo$(C_{10}U)_n$, ratio of C to U in one strand is 10:1;
- $rI_n$•ribo$(C_{11}U)_n$, ratio of C to U in one strand is 11:1;
- $rI_n$•ribo$(C_{12}U)_n$, ratio of C to U in one strand is 12:1;
- $rI_n$•ribo$(C_{13}U)_n$, ratio of C to U in one strand is 13:1;
- $rI_n$•ribo$(C_{14}U)_n$, ratio of C to U in one strand is 14:1;
- $rI_n$•ribo$(C_{15}U)_n$, ratio of C to U in one strand is 15:1;
- $rI_n$•ribo$(C_{16}U)_n$, ratio of C to U in one strand is 16:1;
- $rI_n$•ribo$(C_{17}U)_n$, ratio of C to U in one strand is 17:1;
- $rI_n$•ribo$(C_{18}U)_n$, ratio of C to U in one strand is 18:1;
- $rI_n$•ribo$(C_{19}U)_n$, ratio of C to U in one strand is 19:1;
- $rI_n$•ribo$(C_{20}U)_n$, ratio of C to U in one strand is 20:1;
- $rI_n$•ribo$(C_{21}U)_n$, ratio of C to U in one strand is 21:1;
- $rI_n$•ribo$(C_{22}U)_n$, ratio of C to U in one strand is 22:1;
- $rI_n$•ribo$(C_{23}U)_n$, ratio of C to U in one strand is 23:1;
- $rI_n$•ribo$(C_{24}U)_n$, ratio of C to U in one strand is 24:1;
- $rI_n$•ribo$(C_{25}U)_n$, ratio of C to U in one strand is 25:1;
- $rI_n$•ribo$(C_{26}U)_n$, ratio of C to U in one strand is 26:1;
- $rI_n$•ribo$(C_{27}U)_n$, ratio of C to U in one strand is 27:1;
- $rI_n$•ribo$(C_{28}U)_n$, ratio of C to U in one strand is 28:1;
- $rI_n$•ribo$(C_{29}U)_n$, ratio of C to U in one strand is 29:1;
- $rI_n$•ribo$(C_{4-29}U)_n$ ratio of C to U in one strand is 4-29:1;
- $rI_n$•ribo$(C_{4-29}G)_n$ ratio of C to G in one strand is 4-29:1;
- $rI_n$•r$(C_{11-14}U)_n$ ratio of C to U in one strand is 11-14:1;
- $rI_n$•ribo$(C_{12}U)_n$ ratio of C to U in one strand is 12:1;
- $rI_n$•ribo$(C_{30}U)_n$ ratio of C to U in one strand is 30:1;
- $rI_n$•ribo$(C_{30-35}U)_n$ ratio of C to U in one strand is 30-35:1; and
- r(Poly A•Poly U)$_n$.

Briefly, tdsRNA is a type of dsRNA as described below. It is understood that if one strand is n in length the other strand will also be n in length even if it is not stated. Also, each intermediate value of the ratio is also claimed where a range is claimed.

For example, $rI_n$•ribo$(C_{4-29}U)_n$ may encompass individually: $rI_n$•ribo$(C_4U)_n$, $rI_n$•ribo$(C_5U)_n$, $rI_n$•ribo$(C_6U)_n$, $rI_n$•ribo$(C_7U)_n$, $rI_n$•ribo$(C_8U)_n$, $rI_n$•ribo$(C_9U)_n$, $rI_n$•ribo$(C_{10}U)_n$, $rI_n$•ribo$(C_{11}U)_n$, $rI_n$•ribo$(C_{12}U)_n$, $rI_n$•ribo$(C_{13}U)_n$, $rI_n$•ribo$(C_{14}U)_n$, $rI_n$•ribo$(C_{15}U)_n$, $rI_n$•ribo$(C_{16}U)_n$, $rI_n$•ribo$(C_{17}U)_n$, $rI_n$•ribo$(C_{18}U)_n$, $rI_n$•ribo$(C_{19}U)_n$, $rI_n$•ribo$(C_{20}U)_n$, $rI_n$•ribo$(C_{21}U)_n$, $rI_n$•ribo$(C_{22}U)_n$, $rI_n$•ribo$(C_{23}U)_n$, $rI_n$•ribo$(C_{24}U)_n$, $rI_n$•ribo$(C_{25}U)_n$, $rI_n$•ribo$(C_{26}U)_n$, $rI_n$•ribo$(C_{27}U)_n$, $rI_n$•ribo$(C_{28}U)_n$, and $rI_n$•ribo$(C_{29}U)_n$. As another example, $rI_n$•ribo$(C_{30-35}U)_n$ will encompass individually: $rI_n$•ribo$(C_{30}U)_n$, $rI_n$•ribo$(C_{31}U)_n$, $rI_n$•ribo$(C_{32}U)_n$, $rI_n$•ribo$(C_{33}U)_n$, $rI_n$•ribo $(C_{34}U)_n$, and $rI_n$•ribo$(C_{35}U)_n$.

That is, each of the above molecules is also individually claimed as part of the invention and individually viewed as an embodiment.

Specifically-configured tdsRNA may be of the general formula ribo$(I_n)$•ribo$(C_{4-29}U)_n$, ribo$(I_n)$•ribo$(C_{11-14}U)_n$, or ribo$(I_n)$•ribo$(C_{12}U)_n$, wherein the strands are comprised of ribonucleotides (ribo) and n is an integer from about 40 to about 40,000. For example, a strand comprised of poly (ribocytosinic$_{4-29}$ribouracilic acid), poly(ribocytosinic$_{11-14}$ribouracilic acid), or poly(ribocytosinic$_{4-29}$ribouracilic acid) may be partially hybridized to an opposite strand comprised of poly(riboinosinic acid) such that the two strands form an RNA double helix (dsRNA) that is not paired at the uracil base (i.e., mismatch).

For a subject (e.g., 150 lb or 70 Kg human) the dose of dsRNA may range from 0.1 to 1,000,000 µg, preferably from 0.4 to 400,000 µg.

Alternatively, the tdsRNA may be matched (i.e., not in mismatched form). Thus, polyadenylic acid complexed with polyuridylic acid (poly A•poly U) (i.e., r(Poly A•Poly U)$_n$) may be used. The matched dsRNA may be administered in the same method as any of the mismatched tdsRNAs.

tdsRNAs may be administered by any known administration method (see, e.g., detailed description of "Administering Methods" for a more detailed listing).

Formulations for administration include aqueous solutions, syrups, elixirs, powders, granules, tablets and capsules which typically contain conventional excipients such as binding agents, fillers, lubricants, disintegrants, wetting agents, suspending agents, emulsifying agents, preservatives, buffer salts, flavoring, coloring and/or sweetening agents. They may be applied nasally with a spray or nebulizer. It will be appreciated that the preferred route will vary with the condition and age of the recipient, the nature of the infection or condition, and the chosen active ingredient.

In another aspect, the mismatched dsRNA can be a rugged dsRNA (see, e.g., U.S. Pat. Nos. 8,722,874 and 9,315,538). In one aspect, a rugged dsRNA can be an isolated double-stranded ribonucleic acid (dsRNA) which is resistant to denaturation under conditions that are able to separate hybridized poly(riboinosinic acid) and poly(ribocytosinic acid) strands, wherein only a single strand of said isolated dsRNA comprises one or more uracil or guanine bases that are not base-paired to an opposite strand and wherein said single strand is comprised of poly (ribocytosinic$_{30-35}$uracilic acid). Further, the single strand may be partially hybridized to an opposite strand comprised of poly(riboinosinic acid). In another aspect, rugged dsRNA may be an isolated double-stranded ribonucleic acid (dsRNA) which is resistant to denaturation under conditions that are able to separate hybridized poly(riboinosinic acid) and poly(ribocytosinic acid) strands, wherein said isolated dsRNA is comprised of ribo$(I_n)$•ribo$(C_{30-35}U)_n$, in which ribo is a ribonucleotide and n is an integer from 40 to 500 or 40 to about 40,000.

In another aspect, the tdsRNA may be an isolated double-stranded ribonucleic acid (dsRNA) enzymatically active under thermal stress comprising: each strand with a molecular weight of about 250 kDa to about 320 kDa, a single strand comprised of poly(ribocytosinic$_{4-29}$uracilic acid) and an opposite strand comprised of poly(riboinosinic acid), wherein the two strands do not base pair the position of the uracil base, wherein the two strands base pair the position of the cytosine base, and wherein said strands are partially hybridized. In another aspect, rugged dsRNA may be an isolated double-stranded ribonucleic acid (dsRNA) enzymatically active under thermal stress comprising: each strand of a length from about 380 bases to about 450 bases, a single strand comprised of poly(ribocytosinic$_{4-29}$uracilic acid) and an opposite strand comprised of poly(riboinosinic acid), wherein the two strands do not base pair the position of the uracil base, wherein the two strands base pair the position of the cytosine base, and wherein said strands are partially hybridized. In another aspect, rugged dsRNA may be an isolated double-stranded ribonucleic acid (dsRNA) enzymatically active under thermal stress comprising: each strand with about 4 to about 5000 helical turns, preferably 30 to 38 helical turns of duplexed RNA strands (dsRNA), a single strand comprised of poly(ribocytosinic$_{4-29}$uracilic acid) and an opposite strand comprised of poly(riboinosinic acid), wherein the two strands do not base pair the position of the uracil base, wherein the two strands base pair the position of the cytosine base, and wherein said strands are partially hybridized.

After synthesis, rugged dsRNA may be isolated by at least subjecting the partially hybridized strands of a population of dsRNA to conditions that denature most dsRNA (more than 10 wt % or mol %, more than 20 wt % or mol %, more than 30 wt % or mol %, more than 40 wt % or mol %, more than 50 wt % or mol %, more than 60 wt % or mol %, more than 70 wt % or mol %, more than 80 wt % or mol %, more than 90 wt % or mol %, more than 95 wt % or mol %, or more than 98 wt % or mol %) in the population, and then selection negatively or positively (or both) for dsRNA that remain partially hybridized. The denaturing conditions to unfold at least partially hybridized strands of dsRNA may comprise an appropriate choice of buffer salts, pH, solvent, temperature, or any combination thereof. Conditions may be empirically determined by observation of the unfolding or melting of the duplex strands of ribonucleic acid. The yield of rugged dsRNA may be improved by partial hydrolysis of longer strands of ribonucleic acid, then selection of (partially) hybridized stands of appropriate size and resistance to denaturation.

The purity of rugged dsRNA, which functions as tdsRNA, may thus be increased from less than about 0.1-10 mol % (e.g., rugged dsRNA is present in at least 0.1 mol % or 0.1 wt percent but less than about 10 mol % or 10 wt percent) relative to all RNA in the population after synthesis to a higher purity. A higher purity may be more than 20 wt % or mol %; more than 30 wt % or mol %; more than 40 wt % or mol %; more than 50 wt % or mol %; more than 60 wt % or mol %; more than 70 wt % or mol %; more than 80 wt % or mol %; more than 90 wt % or mol %; and more than 98 wt % or mol %. All wt % or mol % is relative to all RNA present in the same composition.

The molecular weight of rugged dsRNA may be from about 250 kDa to about 320 kDa, or from about 270 kDa to about 300 kDa. Lengths of a single or both strands of rugged dsRNA may be from about 380 bases to about 450 bases, or from about 400 bases to about 430 bases. The number of helical turns made by duplexed RNA strands of rugged dsRNA may be from about 30 to about 38, or from about 32 to about 36.

In another aspect, at least one or more different rugged dsRNA may be administered to a subject (e.g., human patient or animal) in need of such treatment.

The recommended dosage of tdsRNA will depend on the clinical status of the subject and the physician's or veterinarian's experience treating the disease or other pathological condition. Mismatched dsRNA may be dosed at from about 0.5 mg to about 60 mg per day, from about 5 mg to about 400 mg per day, from 25 mg to about 700 mg per day, or from about 10 mg to about 800 mg per day in a subject (e.g., body mass of about 70-80 Kg for a human patient) on a schedule of either once a day up to 7 days weekly or once-weekly to thrice-weekly (preferably twice weekly), albeit the dose amount and/or frequency may be varied by the physician or veterinarian in response to the subject's symptoms. That is, for example, the administration may be in 50-1400 milligrams every other day leading to an average daily dosage of 25-700 milligrams per day.

The nucleic acid in solid form may be dissolved using known diluents for administration such as, for example, physiological phosphate-buffered saline, and then infused intravenously. It will be appreciated that the preferred dosage may vary with the age, condition, gender, or health status of the subject; the nature of the disease or other pathological condition, including the number and severity of symptoms; and the chosen active ingredient.

Immune Checkpoints and Checkpoint Inhibitors (Also Called Immune Checkpoint Inhibitors)

Immune checkpoints, which act as the off-switch on the T-cells of the immune system, have been investigated to restore the immune response with targeted agents, thus indirectly treating cancer by activating the body's immune system. As used herein, the terms "checkpoint inhibitor" and "immune checkpoint inhibitor" are interchangeable and refer to molecules that totally or partially (1) reduce, (2) inhibit, (3) interfere with (4) modulate or (5) any combination of (1) to (4), one or more checkpoint proteins. Immune checkpoint proteins (checkpoint proteins) are the proteins that regulate T-cell activation or function. These proteins are responsible for co-stimulatory or inhibitory interactions of T-cell responses. These checkpoint proteins include, for example, checkpoint inhibitors such as PD-1 and checkpoint inhibitor receptors such as PD-L1. Other checkpoint proteins are listed in this disclosure.

Immune checkpoint proteins regulate and maintain self-tolerance and the duration and amplitude of physiological immune responses. Immune checkpoint inhibitors include antibodies or are derived from antibodies. In preferred aspects of this and other embodiments, the immune checkpoint inhibitor is selected from a group consisting of an anti-PD-1 antibody, an anti-PD-L1 antibody, an anti-CTLA-4 antibody, anti CD80 antibody; anti CD86 antibody; and combinations thereof. In a more preferred aspect, the immune checkpoint inhibitors is at least one selected from the group consisting of ipilimumab (YERVOY®, (Bristol-Myers Squibb); nivolumab (OPDIVO®, Bristol-Myers Squibb); and pembrolizumab (KEYTRUDA®; Merck).

Preferably, the immune checkpoint inhibitor is selected from a group consisting of alemtuzumab (CAMPATH-1H®); AMP-224 (GlaxoSmithKline/Amplimmune); AMP-514 (Amplimmune/AZ); arelumab (Merck Serono); atezolizumab (TECENTRIQ®; Roche/Genentech) [targets PD-L1]; AUNP 12 (Aurigene and Pierre Fabre); avelumab (BAVENCIO®) [targets PD-L1]; BMS-936559 BMS-986016 (Bristol-Meyers Squibb); BMS-986016 (Bristol-Meyers Squibb); cemiplimab (LIBTAYO®) [targets PD-1]; CP-870,893 (Genentech); CT-011; durvalumab (IMFINIZI®); Durvalumab (IMFINZI®) [targets PD-L1]; Galiximab (Biogen Idec); IMP321 (Immutep S.A.); INCB024360 (Incyte); Indoximod (NewLink Genetics); IPH2101 (Innate Pharma/Bristol-Myers Squibb); ipilimumab (YERVOY®, (Bristol-Myers Squibb); Libtayo (cemiplimab-rwlc); lambrolizumab; lirilumab (Bristol-Myers Squibb); MDX-1105 (Medarex, Inc./Bristol Myer Squibb); MEDI-4736 (Medimmune/AstraZeneca); MEDI-6469 (MedImmune/AZ); MGA271 (Macrogenics); MIHI; Mogamulizumab (Kyowa Hakko Kirin); MPDL3280A (Roche); nivolumab (OPDIVO®, Bristol-Myers Squibb) [targets PD-1]; NLG-919 (NewLink Genetics); ofatumumab (ARZERRA®); pembrolizumab (KEYTRUDA®; Merck) [targets PD-1]; PF-05082566 (Pfizer); pidilizumab (Curetech); rituximab (RITUXAN®); tremelimumab; urelumab (Bristol-Meyers Squibb); Varlilumab (CellDex Therapeutics); and a combination thereof Combinations may be, for example, combinations approved by the FDA such as Opdivo plus Yervoy for certain forms of colorectal cancer; Keytruda with Lenvima for advanced endometrial carcinoma; Tecentriq plus certain chemotherapy drugs for small cell lung cancer.

Aspects of immune checkpoints are known and were published in the following: U.S. Pat. Nos. 8,168,757; 8,735,553; WO2002086083; WO2004004771; WO2004056875; WO2006121168; WO2008156712; WO2010077634; WO2011066389; WO2011161699; WO2012168944; WO2013132317; WO2013144704; WO2014055897; WO2014100079; WO2016044900; WO2016142833; WO2016142835; WO2016142852; WO2016142886; and WO2016142894.

Ipilimumab (YERVOY), a monoclonal antibody that targets cytotoxic T-lymphocyte-associated antigen 4 (CTLA-4) and nivolumab (Opdivo), a monoclonal antibody that targets the programmed cell death protein 1 (PD-1) on the surface of T-cells, have been approved by the U.S. Food and Drug Administration for the treatment of advanced melanoma, advanced renal cell carcinoma, and non-small cell lung cancer.

Examples of immune checkpoint inhibitors include a reagent that inhibits, binds to, or interacts with a ligand of a checkpoint protein. A partial list of checkpoint proteins are listed below: 2B4; A2aR; B-7 family ligand; B7-H3; B7-H4; B and T lymphocyte attenuator (BTLA); BMA; CD112; CD137; CD160; CD2; CD20; CD226; CD27; CD276; CD28; CD30; CD33; CD40; CD47; CD52; CD70; CD80; CD86; CGEN-15049; CHK 1; CHK2; cytotoxic T-lymphocyte antigen-4 (CTLA-4); DR3; galectin 9 (GAL9); GITR; herpesvirus entry mediator (HVEM); HVEM; ICOS; IDO1; IDO2; Killer-Cell Immunoglobulin-Like Receptor (KIR); LAG3; LAIR; LAIR1; LAIR2; LIGHT; lymphocyte activation gene 3 (LAG-3); MARCO; OX-40; PD-1; PD-L1; PD-L2; PS; SIRP alpha; SLAM; T cell immunoreceptor with Ig and ITIM domains (TIGIT); T cell membrane protein 3 (TIM3); V-domain immunoglobulin (Ig)-containing suppressor of T-cell activation (VISTA); VTCN1; and any combination thereof.

PD-L1 and PD-L2

PD-L1 and PD-L2 are receptors and are negative regulator of immune activation through inhibition of effective T cell function. They are key regulators in a wide spectrum of immune responses and play a critical role in autoimmunity and self-tolerance as well as in cancer immunology. Evidence suggests that cancer cells use at least the PD-1/PD-L1 or PD-1/PD-L2 pathway to escape anti-tumor immunity.

PD-L1 and PD-L2 Inhibitor

In a preferred embodiment, the checkpoint inhibitor is a PD-1, PD-L1 or PD-L2 inhibitor. The terms "PD-L1 inhibitor" or "PD-L2 inhibitor" refer to a moiety (e.g., compound, nucleic acid, polypeptide, antibody) that decreases, inhibits, blocks, abrogates or interferes with the activity, binding of PD-L1 or PD-L2 to their receptor, PD-1, or expression of PD-L1 or PD-L2 including variants, isoforms, species homologs of human PD-L1 or human PD-L2 (e.g., mouse) and analogs that have at least one common epitope with PD-L1 or PD-L2. A PD-L1 inhibitor or a PD-L2 inhibitor include molecules and macromolecules such as, for example, compounds (small molecule compounds), nucleic acids, polypeptides, antibodies, peptibodies, diabodies, minibodies, single-chain variable fragments (ScFv), and fragments or variants thereof. Thus, a PD-L1 inhibitor or PD-L2 inhibitor as used herein, refers to any moiety that antagonizes PD-L1 activity or PD-L2 activity, its binding to PD-1, or its expression. PD-L1 or PD-L2 inhibitor efficacy can be measured, for example, by its inhibitor concentration at 50% (half-maximal inhibitor concentration or $IC_{50}$). PD-L1 or PD-L2 inhibitors include exemplary compounds and compositions described herein. A PD-L1 inhibitor antibody refers to a PD-L1 inhibitor which is a monoclonal or polyclonal antibody as described herein. Similarly, a PD-L2 inhibitor antibody refers to a PD-L2 inhibitor which is a monoclonal or polyclonal antibody as described herein.

More Detailed Description of Various Aspects

Pharmaceutical Composition

The pharmaceutical composition comprising one or more active agents listed above may be administered to a subject by any local or systemic route known in the art including enteral (e.g., oral, feeding tube, enema), topical (e.g., device such as a nebulizer for inhalation through the respiratory system, skin patch acting epicutaneously or transdermally, suppository acting in the rectum or vagina), and parenteral (e.g., subcutaneous, intravenous, intramuscular, intradermal, or intraperitoneal injection; buccal, sublingual, or transmucosal; inhalation or instillation intranasally or intratracheally). The pharmaceutical composition and/or the active agents may be micronized by milling or grinding solid material, dissolved in a vehicle (e.g., sterile buffered saline or water) for injection or instillation (e.g., spray), topically applied, or encapsulated in a liposome or other carrier for targeted delivery. It will be appreciated that the preferred route may vary with the age, condition, gender, or health status of the subject; the nature of the disease or other pathological condition, including the number and severity of symptoms; and the chosen active ingredient.

Formulation

Formulations for administration (i.e., pharmaceutical compositions) may include aqueous solutions, syrups, elixirs, powders, granules, tablets, and capsules which typically contain conventional excipients such as binding agents, fillers, lubricants, disintegrants, wetting agents, suspending agents, emulsifying agents, preservatives, buffer salts, flavoring, coloring, and/or sweetening agents. It will be appreciated that the preferred formulation may vary with the age, condition, gender, or health status of the subject; the nature of the disease or other pathological condition, including the number and severity of symptoms; and the chosen active ingredient.

Medicament

In another aspect, a medicament (e.g., a pharmaceutical composition) containing the immune activator(s) (i.e., checkpoint inhibitor and tdsRNA) is provided. Optional other components of the medicament include excipients and a vehicle (e.g., aqueous buffer or water for injection) packaged aseptically in one or more separate containers (e.g., nasal applicator or injection vial). Processes for using and making the medicament are also provided. Further aspects will be apparent from the following description and claims, and any generalizations thereto.

Effective Amount

The compositions are delivered in effective amounts. The term "effective amount" refers to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. Also, based on testing, the toxicity of the inhibitor is expected to be low. The effective amount for any particular application can vary depending on such factors as the disease or condition being treated, the particular inhibitor being administered, the size of the subject, or the severity of the disease or condition. One of ordinary skill in the art can empirically determine the effective amount of a particular active ingredient without necessitating undue experimentation. It is preferred generally that a maximum dose be used, that is, the highest safe dose according to medical judgment.

For any compound described herein, the therapeutically effective amount can be initially determined from preliminary in vitro studies and/or animal models. A therapeutically effective dose can also be determined from human data for inhibitors that have been tested in humans and for compounds that are known to exhibit similar pharmacological activities, such as other related active agents. The applied dose can be adjusted based on the relative bioavailability and potency of the administered compound. Adjusting the dose to achieve maximal efficacy based on the methods described above and other methods are well known in the art, is well within the capabilities of the ordinarily skilled artisan.

Administration

Suitable administration/treatment protocols for treating cancer or tumor in a subject include, for example, administering to the patient (subject) an effective amount of tdsRNA and an immune checkpoint inhibitor.

In some embodiments, the combination therapy of the invention comprises administration of tdsRNA and an immune checkpoint inhibitor. Any compound or chemical or formulation in this disclosure may be administered by any of the administration methods disclosed. The tdsRNA and the immune checkpoint inhibitor may be administered in any suitable manner known in the art. For example, the tdsRNA and the immune checkpoint inhibitor may be administered sequentially (at different times) or concurrently (at the same time).

In some embodiments, the immune checkpoint inhibitor is administered before the administration of the tdsRNA. In some embodiments, the immune checkpoint inhibitor is administered simultaneously with the administration of the tdsRNA. In some embodiments, the immune checkpoint inhibitor is administered after the administration of the tdsRNA.

In some embodiments, the tdsRNA or an immune checkpoint inhibitor is administered continuously. In some embodiments, the tdsRNA or immune checkpoint inhibitor is administered intermittently.

In some embodiments, the immune checkpoint inhibitor and the tdsRNA are co-administered, for example, the administration of said immune checkpoint inhibitor and the tdsRNA as two separate formulations. The co-administration can be simultaneous or sequential in either order. In one further embodiment, there is a time period while both (or all) antibodies simultaneously exert their biological activities. Said immune checkpoint inhibitor and tdsRNA are co-administered either simultaneously or sequentially, for example, intravenous (i.v.) through a continuous infusion. When both therapeutic agents are co-administered sequentially the therapeutic agents are administered in two separate administrations that are separated by a "specific period of time". The term specific period of time is meant anywhere from 1 hour to 30 days. For example, one of the agents can be administered within the following time periods. About 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 day. About 24, 23,22, 21, 20, 19, 18, 17, 16, 15, 14, 13, 12, 11, 10, 9, 8, 7, 6, 5, 4, 3, 2 or 1 hour. These are times from the administration of the other therapeutic agent. In some embodiments, the specific period time is 10, 9, 8, 7, 6, 5, 4, 3, 2, or 1 day. In other embodiment the time period is 24, 23, 22, 21, 20, 19, 18, 17, 16, 15, 14, 13, 12, 11, 10, 9, 8, 7, 6, 5, 4, 3, 2 or 1 hour. In some embodiments, simultaneous administration means at the same time or within a short period of time, usually less than 1 hour.

A dosing period as used herein is meant for a period of time, during which each member of the composition has been administered at least once. A dosing period is usually about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, and, in one embodiment, 6, 7, 8, 9, 10, 11, 12, 13, or 14 days, for example, 7 or 14 days.

In certain embodiments, multiple (for example, 2, 3, 4, 5, 6, 7, 8, 9, 10 or more) doses of an tdsRNA and multiple (for example, 2, 3, 4, 5, 6, 7, 8, 9, 10 or more) doses of an immune checkpoint inhibitor are administered to a subject in need of treatment.

In certain embodiments, the immune checkpoint inhibitor is administered in a dose of 0.01 mg/kg, 0.05 mg/kg, 0.1 mg/kg, 0.2 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg or 30 mg/kg. The dose of the immune checkpoint inhibitor may vary from about 0.01 mg/kg to 30 mg/kg, preferably 0.1 mg/kg to 20 mg/kg, more preferably 1 mg/kg to 10 mg/kg. In certain embodiments, the immune checkpoint inhibitor is administered by injection (e.g., subcutaneously or intravenously) at a dose of about 0.01 mg/kg to 30 mg/kg, e.g., about 0.1 mg/kg to 20 mg/kg, about 1 mg/kg to 10 mg/kg, about 1 mg/kg to 5 mg/kg, or about 1 to 3 mg/kg.

In certain embodiments, the checkpoint inhibitor is administered one dose per day, one dose every 2 days, one dose every 3 days, one dose every 4 days, one dose every 5 days, once a week, once every two weeks, once every three weeks or once every four weeks, preferably one dose every 3 days. In certain embodiments, the checkpoint inhibitor is administered as a single dose, in two doses, in three doses, in four doses, in five doses, or in 6 or more doses. The dosing schedule can vary from, e.g., once a week to once every 2, 3, or 4 weeks. In one embodiment, the immune checkpoint inhibitor is administered at a dose from about 1 mg/kg to 10 mg/kg every other week.

In certain embodiments, the tdsRNA is administered in a dose of 0.1 mg/kg, 0.2 mg/kg, 0.3 mg/kg, 0.5 mg/kg, 0.7 mg/kg, 0.8 mg/kg, 1 mg/kg, 2 mg/kg, 2.1 mg/kg, 3 mg/kg, 4 mg/kg, 5 mg/kg, 6 mg/kg, 7 mg/kg, 8 mg/kg, 9 mg/kg, 10 mg/kg, 15 mg/kg or 20 mg/kg. In another embodiment, the dosage of an tdsRNA of the invention administered to prevent and/or treat a cancer associated with increased levels of tdsRNA in a patient is a unit dose of about 0.1 mg/kg to about 20 mg/kg, about 0.1 mg/kg to about 10 mg/kg, about 0.1 mg/kg to about 8 mg/kg, about 0.1 mg/kg to about 7 mg/kg, about 0.1 mg/kg to about 6 mg/kg, about 0.1 mg/kg to about 5 mg/kg, about 0.1 mg/kg to about 4 mg/kg, preferably, about 0.1 mg/kg to about 3 mg/kg, about 0.2 mg/kg to 3 mg/kg, about 0.3 mg/kg to about 3 mg/kg, about 0.4 mg/kg to about 3 mg/kg, about 0.6 mg/kg to about 3 mg/kg, about 0.8 mg/kg to about 3 mg/kg, about 0.1 mg/kg to 2 mg/kg, about 0.1 mg/kg to 1 mg/kg. Total daily dose may vary from 20 mg to 200 mg, preferably 50 mg to 150 mg, most preferably 80 mg to 140 mg. In a preferred embodiment, an tdsRNA of the present invention is administered at a unit dose of about 0.1 mg/kg, about 0.2 mg/kg, about 0.4 mg/kg, about 0.6 mg/kg, about 0.8 mg/kg, about 1 mg/kg, about 2 mg/kg, about 3 mg/kg, about 4 mg/kg or 5 mg/kg. In one embodiment, the tdsRNA is administered at a dose from about 1 mg/kg to 10 mg/kg biweekly.

In certain embodiments, the tdsRNA is administered one dose per day, one dose every 2 days, one dose every 3 days, one dose every 4 days, one dose every 5 days, once a week, once every two weeks, or once every four weeks, preferably one dose every 3 days. In certain embodiments, the tdsRNA is administered as a single dose, in two doses, in three doses, in four doses, in five doses, or in 6 or more doses. The dosing schedule can vary from, e.g., once a week to once every 2, 3, or 4 weeks. In one embodiment, the tdsRNA is administered at a dose from about 0.50 mg/kg to 10 mg/kg every other week. In certain embodiments, the dose frequency may vary from once a day to once a month.

An effective amount of the tdsRNA and the immune checkpoint inhibitor may be administered for prevention or treatment of cancer. The appropriate dosage of the tdsRNA and/or the immune checkpoint inhibitor may be determined based on the type of disease to be treated, the type of the tdsRNA and the immune checkpoint inhibitor, the severity and course of the disease, the clinical condition of the subject, the subject's clinical history and response to the treatment, the symptoms involved, the subject's body mass, gender, immune status and the discretion of the attending physician.

Preferably, the dosages of therapeutic agents used in combination therapies of the invention are lower than those which have been or are currently being used to prevent and/or treat a tumor-associated with increased levels of tdsRNA and/or immune checkpoint molecule.

In some embodiments, a method of treating cancer will be performed even with a low likelihood of success, but which, given the medical history and estimated survival expectancy of a patient, is nevertheless deemed to induce an overall beneficial course of action.

Accordingly, in one embodiment, the dose of the tdsRNA and immune checkpoint inhibitor is calculated as mg/kg body weight. However, in another embodiment, the dose of the tdsRNA and/or immune checkpoint inhibitor is a flat fixed dose that is fixed irrespective of the weight of the patient.

The tdsRNA and the immune checkpoint inhibitor may be administered by the same route of administration or by different routes of administration. In some embodiments, the tdsRNA is administered intravenously, intramuscularly, subcutaneously, topically, orally, transdermally, intraperitoneally, intraorbitally, by implantation, by inhalation, intrathecally, intraventricularly, or intranasally. In some embodiments, the immune checkpoint inhibitor is administered intravenously, intramuscularly, subcutaneously, topically, orally, transdermally, intraperitoneally, intraorbitally, by implantation, by inhalation, intrathecally, intraventricularly, or intranasally.

In some embodiments, the immune checkpoint inhibitor is a PD-L1 or PD-L2 antagonist (for example, anti-PD-L1 antibody). In some embodiments, the anti-PD-L1 antibody or the anti-PD-L2 antibody is administered to the subject intravenously at a dose of 120 mg once every three weeks. In some embodiments, the anti-PD-L1 antibody is administered with an tdsRNA (for example, AMPLIGEN®).

Antibody

An “antibody” may be a natural or conventional antibody in which two heavy chains are linked to each other by disulfide bonds and each heavy chain is linked to a light chain by a disulfide bond. There are two types of light chain, lambda (I) and kappa (k). There are five main heavy chain classes (or isotopes) which determine the functional activity of an antibody molecule: IgM, IgD, IgG, IgA, and IgE, having heavy chains designated alpha, delta, epsilon, gamma and mu, respectively.

The light chain includes two domains or regions, a variable domain (VL) and a constant domain (CL). The heavy chain includes four domains, a variable domain (VH) and three constant domains (CH1, CH2, and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site.

The light and heavy chains of an immunoglobulin each have three CDRs, designated CDR1-L, CDR2-L, CDR3-L for the light chain and CDR1-H, CDR2-H, CDR3-H for the heavy chain. A conventional antibody-antigen-binding site, therefore, includes six CDRs, comprising the CDR set from each of a heavy and a light chain V region.

“Framework Regions” (FRs) refer to amino acid sequences interposed between CDRs, i.e., to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively.

As used herein, a “human framework region” is a framework region that is substantially identical (about 85%, or more, in particular, 90%, 95%, 97%, 99% or 100%) to the framework region of a naturally occurring human antibody.

As used herein, the term “antibody” denotes conventional antibodies and fragments thereof, as well as single-domain antibodies and fragments thereof, in particular, variable heavy chain of single-domain antibodies, and chimeric, humanized, bispecific or multispecific antibodies.

As used herein, antibody or immunoglobulin also includes “single domain antibodies” which have been more recently described and which are antibodies whose complementary determining regions are part of a single domain polypeptide. Examples of single-domain antibodies include heavy chain antibodies, antibodies naturally devoid of light chains, single domain antibodies derived from conventional four-chain antibodies, engineered single domain antibodies. Single domain antibodies may be derived from any species including, but not limited to mouse, human, camel, llama, goat, rabbit and bovine. Single domain antibodies may be naturally occurring single domain antibodies known as heavy chain antibody devoid of light chains. In particular, Camelidae species, for example, camel, dromedary, llama, alpaca, and guanaco, produce heavy chain antibodies naturally devoid of a light chain. Camelid heavy-chain antibodies also lack the CH1 domain.

The variable heavy chain of these single-domain antibodies devoid of light chains are known in the art as “VHH” or “nanobody.” Similar to conventional VH domains, VHHs contain four FRs and three CDRs. Nanobodies have advantages over conventional antibodies: they are about ten times smaller than IgG molecules, and as a consequence properly folded functional nanobodies can be produced by in vitro expression while achieving high yield. Furthermore, nanobodies are very stable and resistant to the action of proteases. The properties and production of nanobodies have been reviewed by Harmsen and De Haard H J (Appl. Microbiol. Biotechnol. 2007 November; 77(1): 13-22).

The antibody of the invention may be a polyclonal antibody or a monoclonal antibody. Said monoclonal antibody may be humanized. In another example, the antibody may be a fragment selected from the group consisting of Fv, Fab, $F(ab')_2$, Fab', dsFv, $(dsFv)_2$, scFv, $sc(Fv)_2$, diabodies and VHH.

The term “monoclonal antibody” or “mAb” as used herein refers to an antibody molecule of a single amino acid composition that is directed against a specific antigen and is not to be construed as requiring the production of the antibody by any particular method. A monoclonal antibody may be produced by a single clone of B cells or hybridoma, but may also be recombinant, i.e., produced by protein engineering.

The term “chimeric antibody” refers to an engineered antibody which in its broadest sense contains one or more regions from one antibody and one or more regions from one or more other antibody or antibodies. In particular, a chimeric antibody comprises a VH domain and a VL domain of an antibody derived from a non-human animal, in association with a CH domain and a CL domain of another antibody, in particular, a human antibody. As the non-human animal, any animal such as mouse, rat, hamster, rabbit or the like can be used. A chimeric antibody may also denote a multispecific antibody having specificity for at least two different antigens. In an embodiment, a chimeric antibody has variable domains of mouse origin and constant domains of human origin.

The term “humanized antibody” refers to an antibody that is initially wholly or partially of nonhuman origin and which has been modified to replace certain amino acids, in particular in the framework regions of the heavy and light chains, in order to avoid or minimize an immune response in humans. The constant domains of a humanized antibody are most of the time human CH and CL domains. In an embodiment, a humanized antibody has constant domains of human origin.

“Fragments” of antibodies comprise a portion of an intact antibody, in particular, the antigen-binding region or variable region of the intact antibody. Examples of antibody fragments include Fv, Fab, F(ab')2, Fab', dsFv, (dsFv)2, scFv, sc(Fv)2, diabodies, bispecific and multispecific antibodies formed from antibody fragments. A fragment of an antibody may also be a single domain antibody, such as a heavy chain antibody or VHH.

The term "Fab" denotes an antibody fragment having a molecular weight of about 50,000 Da and antigen-binding activity, in which about a half of the N-terminal side of H chain and the entire L chain, among fragments obtained by treating IgG with a protease, papain, are bound together through a disulfide bond.

The term "F(ab')2" refers to an antibody fragment having a molecular weight of about 100,000 Da and antigen-binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 Da and antigen-binding activity, which is obtained by cutting a disulfide bond of the hinge region of the F(ab')2.

A single-chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, in particular by using gene recombination techniques. Divalent and multivalent antibody fragments can form either spontaneously by the association of monovalent scFvs, or can be generated by coupling monovalent scFvs by a peptide linker, such as divalent $sc(Fv)_2$. "dsFv" is a VH::VL heterodimer stabilized by a disulphide bond. "(dsFv)2" denotes two dsFv coupled by a peptide linker.

The term "bispecific antibody" or "BsAb" denotes an antibody that combines the antigen-binding sites of two antibodies within a single molecule. Thus, BsAbs are able to bind two different antigens simultaneously. Genetic engineering has been used with increasing frequency to design, modify, and produce antibodies or antibody derivatives with the desired set of binding properties and effector functions as described for instance in EP 2 050 764 A1.

The term "multispecific antibody" denotes an antibody that combines the antigen-binding sites of two or more antibodies within a single molecule.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Typically, antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with the relevant antigenic forms. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

This invention provides in certain embodiments compositions and methods that include humanized forms of antibodies. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may be used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgGI, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., I. Mol. Biol. 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germline immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore, will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

In one embodiment, the antibody of the invention is modified to reduce or inhibit the ability of the antibody to mediate antibody-dependent cellular cytotoxicity (ADCC) and/or complement-dependent cytotoxicity (CDC) functionality (i.e. an antibody with reduced Fc-effector function"). In particular, the antibodies of the present invention have no Fc portion or have an Fc portion that does not bind FcγRI and C1q. In one embodiment, the Fc portion of the antibody does not bind FcγRI, C1q, or FcγRIII. Antibodies with such functionality, in general, are known. There are native such antibodies, such as antibodies with an IgG4 Fc region. There also are antibodies with Fc portions genetically or chemically altered to eliminate the Antibody dependent cell cytotoxicity (ADCC) and/or complement dependent cytotoxicity (CDC) functionality.

In preferred embodiments, the antibodies are inhibitory antibodies. In some embodiments, said antibodies inhibit ligand-receptor binding.

Definitions

Treat

The terms "treat", "treating", "treated" or "treatment", as used herein, refer to therapeutic treatment wherein the object is to eliminate or lessen symptoms. Beneficial or desired clinical results include, but are not limited to, elimination of symptoms, alleviation of symptoms, diminishment of extent of condition, stabilized (i.e., not worsening) state of condition, delay or slowing of progression of the condition.

Cancer

As used herein, "tumors" and "cancers" are used interchangeably and, unless otherwise defined, "cancer" refers to the growth, division or proliferation of abnormal cells in the body in the form of a solid or liquid tumor. Tumors may be benign or malignant. As used herein, the "stromal microenvironment" includes those stromal cells that are in a tumor cell's microenvironment and support the growth of tumor cells. Cancers that can be treated with the combinations, pharmaceutical compositions, products and methods described herein include, but are not limited to all of the cancers described in this disclosure.

The present invention may be used to treat a neoplastic disease, such as solid or non-solid cancers. As used herein, "treatment" encompasses the prevention, reduction, control and/or inhibition of a neoplastic disease. Such diseases include a sarcoma, carcinoma, adenocarcinoma, melanoma, myeloma, blastoma, glioma, lymphoma or leukemia. Exemplary cancers include, for example, carcinoma, sarcoma, adenocarcinoma, melanoma, neural (blastoma, glioma), mesothelioma and reticuloendothelial, lymphatic or hematopoietic neoplastic disorders (e.g., myeloma, lymphoma or leukemia). In particular aspects, a neoplasm, tumor or cancer includes pancreatic cancer; skin cancer; colorectal cancer; ovarian cancer; melanoma; breast cancer; triple negative breast cancer; head and neck tumor; bladder cancer; renal cell carcinoma; and lung cancer.

Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission.

Cancers that may be treated according to the invention include but are not limited to cells or neoplasms of the bladder, blood, bone, bone marrow, brain, breast, colon, esophagus, gastrointestinal track, gum, head, kidney, liver, lung, nasopharynx, neck, ovary, prostate, skin, stomach, testis, tongue, or uterus. In addition, the cancer may specifically be of the following histological type, though it is not limited to the following: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma, gastrinoma, malignant; cholangiocarcinoma, hepatocellular carcinoma; combined hepatocellular carcinoma and cholangiocarcinoma, trabecular adenocarcinoma, adenoid cystic carcinoma; adenocarcinoma in adenomatous polyp; adenocarcinoma, familial polyposis coli, solid carcinoma; carcinoid tumor, malignant; bronchiolo-alveolar adenocarcinoma, papillary adenocarcinoma, chromophobe carcinoma; acidophil carcinoma; oxyphilic adenocarcinoma, basophil carcinoma; clear cell adenocarcinoma, granular cell carcinoma; follicular adenocarcinoma, papillary and follicular adenocarcinoma, nonencapsulating sclerosing carcinoma; adrenal cortical carcinoma; endometroid carcinoma; skin appendage carcinoma; apocrine adenocarcinoma, sebaceous adenocarcinoma, ceruminous adenocarcinoma, mucoepidermoid carcinoma; cystadenocarcinoma, papillary cystadenocarcinoma, papillary serous cystadenocarcinoma, mucinous cystadenocarcinoma, mucinous adenocarcinoma, signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma with squamous metaplasia, thymoma, malignant; ovarian stromal tumor, malignant; thecoma, malignant; granulosa cell tumor, malignant; androblastoma, malignant; Sertoli cell carcinoma; Leydig cell tumor, malignant; lipid cell tumor, malignant; paraganglioma, malignant; extra-mammary paraganglioma, malignant; pheochromocytoma, glomangiosarcoma, malignant melanoma; amelanotic melanoma; superficial spreading melanoma; malignant melanoma in giant pigmented nevus; epithelioid cell melanoma; blue nevus, malignant; sarcoma; fibrosarcoma, fibrous histiocytoma, malignant; myxosarcoma, liposarcoma, leiomyosarcoma, rhabdomyosarcoma, embryonal rhabdomyosarcoma, alveolar rhabdomyosarcoma, stromal sarcoma; mixed tumor; Mullerian mixed tumor; nephroblastoma, hepatoblastoma, carcinosarcoma, mesenchymoma, malignant; Brenner tumor, malignant; phyllodes tumor, malignant; synovial sarcoma; mesothelioma, malignant; dysgerminoma, embryonal carcinoma; teratoma, malignant; struma ovarii, malignant; choriocarcinoma, mesonephroma, malignant; hemangiosarcoma, hemangioendothelioma, malignant; Kaposi's sarcoma; hemangiopericytoma, malignant; lymphangiosarcoma, osteosarcoma, juxtacortical osteosarcoma, chondrosarcoma, chondroblastoma, malignant; mesenchymal chondrosarcoma, giant cell tumour of bone; Ewing's sarcoma; odontogenic tumour, malignant; ameloblastic odontosarcoma, ameloblastoma, malignant; ameloblastic fibrosarcoma, pinealoma, malignant; chordoma, glioma, malignant; ependymoma, astrocytoma, protoplasmic astrocytoma, fibrillary astrocytoma, astroblastoma, glioblastoma, oligodendroglioma, oligodendroblastoma, primitive neuroectodermal, cerebellar sarcoma; ganglioneuroblastoma, neuroblastoma, retinoblastoma, olfactory neurogenic tumor; meningioma, malignant; neurofibrosarcoma, neurilemmoma, malignant; granular cell tumor, malignant; malignant lymphoma; Hodgkin's disease; Hodgkin's; paragranuloma, malignant lymphoma, small lymphocytic, malignant lymphoma, large cell, diffuse; malignant lymphoma, follicular; mycosis fungoides, other specified non-Hodgkin's lymphomas; malignant histiocytosis, multiple myeloma, mast cell sarcoma; immunoproliferative small intestinal disease; leukemia; lymphoid leukemia; plasma cell leukemia; erythroleukemia, lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Preferably, the neoplastic disease may be tumors associated with a cancer selected from prostate cancer, liver cancer, renal cancer, lung cancer, breast cancer, colorectal cancer, pancreatic cancer, brain cancer, hepatocellular cancer, lymphoma, leukaemia, gastric cancer, cervical cancer, ovarian cancer, thyroid cancer, melanoma, head and neck cancer, skin cancer and soft tissue sarcoma and/or other forms of carcinoma. The tumor may be metastatic or a malignant tumor.

More preferably, the neoplastic disease to be treated is pancreatic cancer; skin cancer; colorectal cancer; ovarian cancer; melanoma; breast cancer; triple negative breast cancer; head and neck tumor; bladder cancer; renal cell carcinoma; and lung cancer.

Synergy

As used herein, the term "synergy" or "synergistic effect" when used in connection with a description of the efficacy of a combination of agents, means any measured effect of the combination which is greater than the effect predicted from a sum of the effects of the individual agents.

Additive Effect

As used herein, the term "additive" or "additive effect" when used in connection with a description of the efficacy of a combination of agents, means any measured effect of the combination which is similar to the effect predicted from a sum of the effects of the individual agents.

Subject

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc. In some aspects of this and other embodiments, the subject is a mammal. Preferably, the mammal is selected from the group consisting of humans, primates, farm animals, and domestic animals. More preferably, the mammal is a human. As used herein, the terms "patient" or "subject" are used interchangeably and mean a mammal, including, but not limited to, a human or non-human mammal, such as a bovine, equine, canine, ovine, or feline. Preferably, the patient is a human.

Survival

As used herein, "survival" refers to the patient remaining alive, and includes overall survival as well as progression free survival. 1-year survival rate and 2-year survival rate refers to the K-M estimate of the proportion of subjects alive at 12 month or 24 months.

Extending Survival

By "extending survival" is meant increasing overall survival and/or progression free survival in a treated patient relative to a control treatment protocol, such as treatment with only ipilimumab. Survival is monitored for at least about one month, two months, four months, six months, nine months, or at least about 1 year, or at least about 2 years, or at least about 3 years, or at least about 4 years, or at least about 5 years, or at least about 10 years, etc., following the initiation of treatment or following the initial diagnosis.

Reduce or Inhibit

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated, the presence or size of metastases, or the size of the primary tumor.

Ameliorate

As used herein, the terms "ameliorate", "ameliorating" and grammatical variations thereof mean to decrease the severity of the symptoms of a disease in a subject.

Effective Amount or Therapeutically Effective Amount

In the present invention, an "effective amount" or a "therapeutically effective amount" of an agent, monoclonal antibody, or fragment thereof or a compound or composition disclosed herein is an amount of such material that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of any active agent disclosed herein or a composition containing the same will be that amount of the active agent or composition, which is the lowest dose effective to produce the desired effect.

In some embodiments, a therapeutically effective amount is an amount sufficient to prevent or delay recurrence of cancer. A therapeutically effective amount can be administered in one or more administrations. The therapeutically effective amount of the drug or combination may result in one or more of the following: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

For example, for the treatment of tumors, a "therapeutically effective dosage" may induce tumor shrinkage by at least about 5% relative to baseline measurement, such as at least about 10%, at least about 20%, at least about 30%, at least about 40%, at least about 50%, at least about 60%, at least about 70%, at least about 80%, at least about 90% or more. The baseline measurement may be derived from untreated subjects.

A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

Contacting

In this embodiment, "contacting" means bringing, e.g., an immune checkpoint inhibitor, and/or one or more additional therapeutic agents into close proximity to the tumor microenvironment. This may be accomplished using conventional techniques of drug delivery to mammals or in the in vitro situation by one or more additional therapeutic agents to a culture media in which the cancer cells are located.

Chemotherapeutic Drugs

For any of the claims, a chemotherapeutic drug may be any one or more drugs used for chemotherapy. The drugs may be in any form such as, for example, in a liposomal form enclosed inside a liposome, slow-release form or in depot forms. Nonlimiting examples of such drugs include at least ABVD; AC; ACE; Abiraterone (Zytiga); Abraxane; Abstral; Actinomycin D; Actiq; Adriamycin; Afatinib (Giotrif); Afinitor; Aflibercept (Zaltrap); Aldara; Aldesleukin (IL-2, Proleukin or interleukin 2); Alemtuzumab (MabCampath); Alkeran; Amsacrine (Amsidine, m-AMSA); Amsidine; Anastrozole (Arimidex); Ara C; Aredia; Arimidex; Aromasin; Arsenic trioxide (Trisenox, ATO); Asparaginase (Crisantaspase, Erwinase); Axitinib (Inlyta); Azacitidine (Vidaza); BEACOPP; BEAM; Bendamustine (Levact); Bevacizumab (Avastin); Bexarotene (Targretin); Bicalutamide (Casodex); Bleomycin; Bleomycin, etoposide and platinum (BEP); Bortezomib (Velcade); Bosulif; Bosutinib (Bosulif); Brentuximab (Adcetris); Brufen; Buserelin (Suprefact); Busilvex; Busulfan (Myleran, Busilvex); CAPE-OX; CAPOX; CAV; CAVE; CCNU; CHOP; CMF; CMV; CVP; Cabazitaxel (Jevtana); Cabozantinib (Cometriq); Caelyx; Calpol; Campto; Capecitabine (Xeloda); Caprelsa; Carbo MV; CarboTaxol; Carboplatin; Carboplatin and etoposide; Carboplatin and paclitaxel; Carmustine (BCNU, Gliadel); Casodex; Ceritinib (Zykadia); Cerubidin; Cetuximab (Erbitux); ChIVPP; Chlorambucil (Leukeran); Cisplatin; Cisplatin and Teysuno; Cisplatin and capecitabine (CX); Cisplatin, etoposide and ifosfamide (PEI); Cisplatin, fluorouracil (5-FU) and trastuzumab; Cladribine (Leustat, LITAK); Clasteon; Clofarabine (Evoltra); Co-codamol (Kapake, Solpadol, Tylex); Cometriq; Cosmegen; Crisantaspase; Crizotinib (Xalkori); Cyclophosphamide; Cyclophosphamide, thalidomide and dexamethasone (CTD); Cyprostat; Cyproterone acetate (Cyprostat); Cytarabine (Ara C, cytosine arabinoside); Cytarabine into spinal fluid; Cytosine arabinoside; DHAP; DTIC; Dabrafenib (Tafinlar); Dacarbazine (DTIC); Dacogen; Dactinomycin (actinomycin D, Cosmegen); Dasatinib (Sprycel); Daunorubicin; De Gramont; Decapeptyl SR; Decitabine (Dacogen); Degarelix (Firmagon); Denosumab (Prolia, Xgeva); Depocyte; Dexamethasone; Diamorphine; Disodium pamidronate; Disprol; Docetaxel (Taxotere); Docetaxel, cisplatin and fluorouracil (TPF); Doxifos; Doxil; Doxorubicin (Adriamycin); Doxorubicin and ifosfamide (Doxifos); Drogenil; Durogesic; EC; ECF; EOF; EOX; EP (Etoposide and cisplatin); ESHAP; Effentora; Efudix; Eldisine; Eloxatin; Enzalutamide; Epirubicin (Pharmorubicin); Epirubicin cisplatin and capecitabine (ECX); Epirubicin, carboplatin and capecitabine (ECarboX); Eposin; Erbitux; Eribulin (Halaven); Erlotinib (Tarceva); Erwinase; Estracyt; Etopophos; Etoposide (Eposin, Etopophos, Vepesid); Everolimus (Afinitor); Evoltra; Exemestane (Aromasin); FAD; FEC; FEC-T chemotherapy; FMD; FOLFIRINOX; FOLFOX; Faslodex; Femara; Fentanyl; Firmagon; Fludara; Fludarabine (Fludara); Fludarabine, cyclophosphamide and rituximab (FCR); Fluorouracil (5FU); Flutamide; Folinic acid, fluorouracil and irinotecan (FOLFIRI); Fulvestrant (faslodex); G-CSF; Gefitinib (Iressa); GemCarbo (gemcitabine and carboplatin); GemTaxol; Gemcitabine (Gemzar); Gemcitabine and capecitabine (GemCap); Gemcitabine and cisplatin (GC); Gemcitabine and paclitaxel (GemTaxol); Gemzar; Giotrif; Gliadel; Glivec; Gonapeptyl Depot; Goserelin (Zoladex); Goserelin (Zoladex, Novgos); Granulocyte colony stimulating factor (G-CSF); Halaven; Herceptin; Hycamtin; Hydrea; Hydroxycarbamide (Hydrea); Hydroxyurea; I-DEX; ICE; IL-2; IPE; Ibandronic acid; Ibritumomab (Zevalin); Ibrutinib (Imbruvica); Ibuprofen (Brufen, Nurofen); Iclusig; Idarubicin (Zavedos); Idarubicin and dexamethasone; Idelalisib (Zydelig); Ifosfamide (Mitoxana); Imatinib (Glivec); Imiquimod cream (Aldara); Imnovid; Instanyl; Interferon (Intron A); Interleukin; Intron A; Ipilimumab (Yervoy); Iressa; Irinotecan (Campto); Irinotecan and capecitabine (Xeliri); Irinotecan de Gramont; Irinotecan modified de Gramont; Javlor; Jevtana; Kadcyla; Kapake; Keytruda; Lanreotide (Somatuline); Lanvis; Lapatinib (Tyverb); Lenalidomide (Revlimid); Letrozole (Femara); Leukeran; Leuprorelin (Prostap, Lutrate); Leustat; Levact; Liposomal doxorubicin; Litak; Lomustine (CCNU); Lynparza; Lysodren; MIC; MMM; MPT; MST Continus; MVAC; MVP; MabCampath; Mabthera; Maxtrex; Medroxyprogesterone acetate (Provera); Megace; Megestrol acetate (Megace); Melphalan (Alkeran); Mepact; Mercaptopurine (Xaluprine); Methotrexate; Methyl prednisolone; Mifamurtide (Mepact); Mitomycin C; Mitotane; Mitoxana; Mitoxantrone (Mitozantrone); Morphgesic SR; Morphine; Myleran; Myocet; Nab-paclitaxel; Nab-paclitaxel (Abraxane); Navelbine; Nelarabine (Atriance); Nexavar; Nilotinib (Tasigna); Nintedanib (Vargatef); Nipent; Nivolumab (Opdivo); Novgos; Nurofen; Obinutuzumab (Gazyvaro); Octreotide; Ofatumumab (Arzerra); Olaparib (Lynparza); Oncovin; Onkotrone; Opdivo; Oramorph; Oxaliplatin (Eloxatin); Oxaliplatin and capecitabine (Xelox); PAD; PC (paclitaxel and carboplatin, CarboTaxol); PE; PMitCEBO; POMB/ACE; Paclitaxel (Taxol); Paclitaxel and carboplatin; Pamidronate; Panadol; Panitumumab (Vectibix); Paracetamol; Pazopanib (Votrient); Pembrolizumab (Keytruda); Pemetrexed (Alimta); Pemetrexed and carboplatin; Pemetrexed and cisplatin; Pentostatin (Nipent); Perjeta; Pertuzumab (Perjeta); Pixantrone (Pixuvri); Pixuvri; Pomalidomide (Imnovid); Ponatinib; Potactasol; Prednisolone; Procarbazine; Procarbazine, lomustine and vincristine (PCV); Proleukin; Prolia; Prostap; Provera; Purinethol; R-CHOP; R-CVP; R-DHAP; R-ESHAP; R-GCVP; RICE; Raloxifene; Raltitrexed (Tomudex); Regorafenib (Stivarga); Revlimid; Rituximab (Mabthera); Sevredol; Sodium clodronate (Bonefos, Clasteon, Loron); Solpadol; Sorafenib (Nexavar); Steroids (dexamethasone, prednisolone, methylprednisolone); Streptozocin (Zanosar); Sunitinib (Sutent); Sutent; TAC; TIP; Tafinlar; Tamoxifen; Tarceva; Targretin; Tasigna; Taxol; Taxotere; Taxotere and cyclophosphamide (TC); Temodal; Temozolomide (Temodal); Temsirolimus; Tepadina; Teysuno; Thalidomide; Thiotepa (Tepadina); Tioguanine (thioguanine, 6-TG, 6-tioguanine); Tomudex; Topotecan (Hycamtin, Potactasol); Torisel; Trabectedin (Yondelis); Trastuzumab (Herceptin); Trastuzumab emtansine (Kadcyla); Treosulfan; Tretinoin (Vesanoid, ATRA); Triptorelin; Trisenox; Tylex; Tyverb; VIDE; Vandetanib (Caprelsa); Vargatef; VeIP; Vectibix; Velbe; Velcade; Vemurafenib (Zelboraf); Vepesid; Vesanoid; Vidaza; Vinblastine (Velbe); Vincristine; Vincristine, actinomycin D (dactinomycin) and cyclophosphamide (VAC); Vincristine, actinomycin and ifosfamide (VAI); Vincristine, doxorubicin and dexamethasone (VAD); Vindesine (Eldisine); Vinflunine (Javlor); Vinorelbine (Navelbine); Vismodegib (Erivedge); Votrient; XELOX; Xalkori; Xeloda; Xgeva; Xtandi; Yervoy; Yondelis; Z-DEX; Zaltrap; Zanosar; Zavedos; Zelboraf;

Zevalin; Zoladex (e.g. breast cancer); Zoladex (e.g. prostate cancer); Zoledronic acid (Zometa); Zometa; Zomorph; Zydelig; and Zytiga.

In this specification, stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity that a person skilled in the art would understand does not affect the operation of the invention or its patentability.

All modifications and substitutions that come within the meaning of the claims and the range of their legal equivalents are to be embraced within their scope. A claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

INCORPORATION BY REFERENCE

All publications, patent applications, and patents mentioned herein are hereby incorporated by reference in their entirety as if each individual publication or patent was specifically and individually indicated to be incorporated by reference. In case of conflict, the present application, including any definitions herein, will control.

EXAMPLES

Example 1: Experimental Results

Currently, surgery is the only potentially curative option for pancreatic cancer, but only around 15% of patients are eligible at initial diagnosis since most pancreatic cancers are detected in an advanced stage of the disease. Around 20% of patients are diagnosed with locally advanced pancreatic cancer and the remaining 65% present with metastatic disease.

The current standard of care (SOC) for locally advanced and metastatic pancreatic carcinoma is FOLFIRINOX, a four-drug cocktail with significant toxicity. Approval of FOLFIRJNOX was based on the Phase 2/3 ACCORD study published in 2011 (Von Hoff et al., 2011). In this study, FOLFIRINOX was compared to Gemcitabine, which was the SOC at that time.

The result of the ACCORD study is that overall survival (OS) increased from 6.8 months with Gemcitabine to 11.1 months with FOLFIRINOX ($p<0.001$). However, the Complete Response Rate (CR) was only 0.6%. Moreover, overall mean survival with second-line therapy following progression on the FOLFIRINOX was only 4.05 months. The data clearly shows that the new treatment options are desperately needed for this devastating malignancy.

One of these novel therapeutic options is immunotherapy, which has shown to be a promising treatment strategy. Essential in this therapeutic strategy is to boost the patient's immune system, by reversing the tumor-antigen-specific T-cell tolerance induced by their tumor.

One goal in immunotherapy is the reprogramming of the tumor microenvironment (TME) to convert "cold" tumors into "hot" tumors that will be responsive to checkpoint blockade. The goal is to unleash the cellular immune response to attack and destroy cancer cells and increase survival by increasing intratumoral $T_{eff}$ (T effector) cells while decreasing intratumoral $T_{reg}$ cells.

Surprisingly, AMPLIGEN® is capable of promoting the selective attraction of CTLs ($T_{eff}$) with a concomitant increase in the Teff/Treg ratio in the TME.

An ability to increase $T_{eff}$ (CD8+ T cells) and improve the Teff/Treg ratio in the TME has significant advantages. In Pancreatic Cancer, tumor-infiltrating CD4+ T cells (high), CD8+ T cells (high), and $T_{reg}$ cells (low) in the TME are independent prognosticators of increased overall survival.

In pancreatic cancer, $T_{reg}$ infiltration into the TME is a bad prognostic indicator for survival. Hiraoka et al. divided pancreatic cancer patients into two cohorts based on values of the $T_{reg}$ cells being higher or lower than the median value in the TME, the low $T_{reg}$ group showed significantly better survival than the high $T_{reg}$ group (Hiraoka, et al., 2006).

Our observation that AMPLIGEN® can increase the $T_{eff}$ (T effector) cell to $T_{reg}$ (T regulator) cell ratio thereby converting a "cold" pancreatic TME into a "hot" pancreatic TME is highly relevant for improving the likelihood of an antitumor response to checkpoint blockade.

In a preclinical model of pancreatic cancer, the combination of AMPLIGEN® and checkpoint blockade (anti-PD-L1) is found to be synergistic for increasing both overall survival and time-to-tumor progression.

We propose the use of AMPLIGEN® in combination with checkpoint blockade to improve the ability to treat cancer. Or more specifically, so that AMPLIGEN® and the checkpoint blockade can perform synergistically. That is, we expect that the (effect of AMPLIGEN®+checkpoint blockade) is greater than that of the (effect of AMPLIGEN®)+(effect of checkpoint blockade).

We have also found that an animal model in melanoma combining AMPLIGEN® with an anti-PD-L1 showed a threefold increase in overall tumor response rate (RECIST (Response Evaluation Criteria In Solid Tumors) Criteria). In addition, in a transgenic mouse model, combining AMPLIGEN® with an anti-PD-L1 drug in pancreatic cancer, shows a synergistic increase in median survival. Moreover, we found in a mouse model of colorectal carcinoma that the AMPLIGEN®+anti-PD-L1 combination showed a median survival increase of greater than 2.5 fold, compared to anti-PD-L1 alone.

The Basis for Barriers to Immunotherapy in Pancreatic Carcinoma

The TME in pancreatic cancer is dominated by immunosuppressive cells including $T_{reg}$ (T regulator) cells and lacks $T_{eff}$ (T effector) cells needed to drive an anti-tumor response. In a minority of patients with a lower prevalence of $T_{reg}$ cells in the TME, a better prognosis was seen.

Importantly, the lack of T effector cells in the TME of patients with pancreatic carcinoma appears to be related to the failure of these T effector cells to migrate from the bone marrow and blood of pancreatic cancer patients to the TME, since high levels of tumor-reactive T cells were easily found in bone marrow samples of patients with pancreatic carcinoma. Thus, these findings suggest that the failure of immunotherapy in pancreatic carcinoma is not because of a lack of antigenicity of the tumor itself or a lack of T effector cells directed against tumor antigens, but a failure to recruit T effector cells into the TME while at the same time reducing the level of $T_{reg}$ cells in the TME.

Increasing the Ratio of $T_{eff}/T_{reg}$ Cells in the TME Using Rintatolimod (Sold Under the Tradename AMPLIGEN®)

Colorectal carcinoma was used as a GI model for pancreatic carcinoma in order to obtain biopsy specimens of the TME. We used AMPLIGEN® to determine if there is improvement in the $T_{eff}/T_{reg}$ ratio in the TME secondary to the AMPLIGEN® induction of desirable chemokines, such as CXCL 10 (Teff-attractant), in the TME, while decreasing the unfavorable chemokines, such as CCL22 (C-C Motif Chemokine Ligand 22; Treg-attractant), thereby increasing the $T_{eff}/T_{reg}$ ratio in the TME.

AMPLIGEN® improves the TME in gastrointestinal cancers including colorectal carcinomas. A colorectal carcinoma trial of AMPLIGEN® plus rIFNa-2b and celecoxib produced an increased ratio of CXCL 10 to CCL22 in the TME along with an increase in the ratio of $T_{eff}/T_{reg}$ markers in nine patients with metastatic colorectal carcinoma compared to controls. See, Example Section below.

Based on these experiments, AMPLIGEN® (rintatolimod) shows an ability to convert "cold" tumors into "hot" tumors which are much more likely to respond to the presence of a checkpoint inhibitor (also called by its function as a checkpoint blockade or an immune checkpoint inhibitor).

We propose that in Pancreatic Cancer tumor-infiltrating CD4+ T (high)/CD8+ T (high)/% $T_{reg}$ (low) in the TME are independent prognosticators of increased overall survival. In Pancreatic Cancer, $T_{reg}$ infiltration into the TME is a bad prognostic indicator for survival. Pancreatic cancer patients were divided into two cohorts based on values of the $T_{reg}$ cells being higher or lower than the median value in the TME, the low $T_{reg}$ group showed significantly better survival than the high $T_{reg}$ group.

The potential of AMPLIGEN® to increase the $T_{eff}$ cell to $T_{reg}$ cell ratio thereby converting a "cold" pancreatic TME into a "hot" pancreatic TME is highly relevant for improving the likelihood of an antitumor response to checkpoint blockade. A combination of AMPLIGEN® and checkpoint blockade (anti-PD-LI) was synergistic in increasing both overall survival and time-to-tumor progression.

Summary of data showing AMPLIGEN® Plus Checkpoint Blockage (Checkpoint Inhibitor) Synergistically Increased Survival In a pancreatic cancer transgenic mouse model, combining AMPLIGEN® with an anti-PD-LI drug shows a synergistic increase in median survival.

In a mouse model of colorectal carcinoma, the combination of AMPLIGEN® plus anti-PD-I showed a median survival increase of greater than 250% compared to anti-PD-I alone.

Pre-clinical cancer studies using mouse models of three different solid tumors show synergistic antitumor activity and/or increased median survival when AMPLIGEN® was combined with checkpoint blockade, compared to checkpoint blockade alone.

Animal model in melanoma combining AMPLIGEN® with an anti-PD-L1 showed a threefold increase in overall response rate (RECIST (Response Evaluation Criteria In Solid Tumors) Criteria). In addition, a study using a transgenic mouse model combining AMPLIGEN® with an anti-PD-LI drug in pancreatic cancer shows a synergistic increase in median survival. Moreover, in a mouse model of colorectal carcinoma, the AMPLIGEN® combination showed a median survival increase of greater than 2.5 fold, compared to anti-PD I alone.

AMPLIGEN® Induced Anti-Tumor Synergy in a Melanoma Model with Checkpoint Immune Suppression Blockade.

AMPLIGEN® was synergistic with anti-PD-LI, yielding an increased anti-tumor response in a B 16 mouse melanoma model. The decrease in tumor size was significant for the AMPLIGEN® 250 μg+anti-PD-LI cohort compared to anti-PD-LI cohort alone ($p=0.023$)

The addition of AMPLIGEN® to anti-PD-LI increased the objective response rate 300%, from 10% with anti-PD-LI alone to 30% with the combination.

Example 2: Pancreatic Cancer

According to the Pancreatic Cancer Action Network, Pancreatic cancer is the fourth leading cause of cancer death in the U.S. It is the only cancer of the most commonly diagnosed with a five-year survival rate at just six percent. Pancreatic cancer is anticipated to move from the fourth to the second leading cause of cancer death in the U.S. by 2020, based on current projections. Accordingly, both the projected number of new pancreatic cancer cases and pancreatic cancer deaths will more than double by 2030 (Matrisian et al., 2012).

In the European Union, the incidence of pancreatic cancer is continuing to increase, and the death rate is projected to increase by about 30% to about 112,000 new cases per year by 2025. More specifically, while breast cancer deaths are 92,000 and 91,000 in 2010 and 2017 respectively, it is expected to be at 90,000 in 2025. On the other hand, pancreatic cancer deaths are 76,000 and 91,000 in 2010, and 2017 respectively, and it is expected increase 30% to 112,000 in 2025.

Pancreatic cancer is associated with overall five-year survival of 5% and thus contributes significantly to cancer-related mortality. A recent paper predicted that pancreatic cancer will be the second leading cause of cancer-related deaths before 2030. Currently, surgery is the only potentially curative option, but only around 15% of patients are eligible at initial diagnosis since most pancreatic cancers are detected in an advanced stage of the disease. Around 20% of patients are diagnosed with locally advanced pancreatic cancer, and the remaining 30-50% present with metastatic disease. It is clear that new treatment options are desperately needed for this devastating malignancy.

The pancreas gland itself is located in the abdomen between the stomach and the spine. It is approximately 6 inches long and shaped like a pear lying on its side. It is categorized into three sections; the head, or the wider part of the pancreas; the body, or the middle section; and the tail, the narrow end of the pancreas. https://world wide web.cancer-.gov/types/pancreatic/patient/pancreatic-treatment-pdq.

Pancreatic cancer, or carcinoma of the pancreas, is a disease in which malignant (cancer) cells form in the tissue of the pancreas. The pancreas is a gland that aids in digestion. It makes juices that break down food with exocrine pancreas cells. It also produces hormones, such as insulin and glucagon to help control blood sugar with endocrine pancreas cells. Most pancreatic cancers start in the exocrine cells. Due to the absence of symptoms in the early stages of pancreatic cancer, the majority of patients are diagnosed when the cancer has spread locally or to other parts of the body.

Pancreatic cancer is a very severe and life-threatening disease that is associated with shortened life expectancy.

Etiologic factors that are linked to the development of adenocarcinoma of the pancreas in adulthood include both tobacco smoking and environmental exposure to tobacco smoking, especially during childhood or in utero from maternal smoking. Smoke from tobacco is estimated to contribute to the development of 20-30% of pancreatic cancer.

Several infectious diseases including *Helicobacter pylori* and hepatitis B also have a positive association with pancreatic adenocarcinoma. Occupational factors have also been linked to 12-29% of cases and include exposure to a wide range of chemicals/solvents such as chlorinated hydrocarbons, polycyclic aromatic hydrocarbons, insecticides, and aliphatic solvents.

Demographic risk factors for pancreatic adenocarcinoma include age between 60-80, African American race, low socioeconomic status, and Ashkenazic Jewish heritage. Several medical conditions with increased risk of pancreatic cancer include diabetes mellitus, chronic cirrhosis, pancreatitis, and a prior cholecystectomy.

Finally, genetic predisposition also plays a minor role in pancreatic cancer risk with 10-20% of pancreatic cancer having a familial link. The etiological risk factors for the development of pancreatic cancer are many and include the following (where the percent shown is listed if available): tobacco smoke (20%-30% contribution); infectious diseases; occupation (12%-29% contribution); demographics; medical conditions; genetics (20%-20% contribution).

Specific Characteristics; Pathophysiological, Histopathological, Clinical Characteristics In recent years evidence has accumulated that tumor-infiltrating lymphocytes (TILs) have a major effect on several important clinical attributes of cancer. It has been shown that type, density and location of T cells in tumors provide a better prognostic value that was superior to, and independent of those of the TNM classification criteria. In pancreatic cancer, the CD8+ T lymphocytes present the predominant T lymphocyte subset and are associated with favorable clinical outcomes. However, it is generally accepted that aside from CD8 T cell number in the tumor environment, more specific analysis of the T cells ($T_{eff}$ vs $T_{reg}$) result in better prognostic or predictive markers in pancreatic cancer (treatment). Thus, analyses of the TME, in particular with respect to the characterization of both the $T_{eff}$ and $T_{reg}$ cells reveals important immune signatures in pancreatic tumors.

Aside from these local immune markers, also in peripheral blood (PB) prognostic and predictive markers have been found. The neutrophil to lymphocyte ratio (NLR) in peripheral blood has shown to be a prognostic marker in pancreatic cancer (Kawahara et al., 2016). The use of (bio)markers from PB is advantageous over local tumor tissue since this is less invasive for patients and can be measured longitudinally over the course of treatment. Currently, the enumeration, activation, presence of regulatory T cells, and co-signaling signature of TILs and PB T cells in pancreatic tumor patients is under investigation. At least in some cases, PB T cells may reflect the TIL co-signaling signature and thus could serve as a surrogate marker for local immune status at diagnosis and during therapy. Tumor cell-free DNA (cfDNA) found in peripheral blood is being actively investigated and is believed will become widely used in the future as a surrogate (liquid biopsy) for direct tumor biopsies with the advantage of metastatic disease sampling.

Pancreatic cancer is difficult to detect and diagnose for the following reasons: (1) There are no noticeable signs or symptoms in the early stages of pancreatic cancer. (2) The signs of pancreatic cancer, when present, are like the signs of many other illnesses, such as pancreatitis or an ulcer. (3) The pancreas is obscured by other organs in the abdomen and it is difficult to visualize clearly on imaging tests.

To appropriately treat pancreatic cancer, it is preferred to evaluate whether the cancer can be resected. Diagnostic tools used include Imaging, Peritoneal Cytology, and Tumor Markers. Imaging can be used to detect tumors, and to determine if the tumor is resectable.

Symptoms of pancreatic cancer include, for example, jaundice; light-colored stools or dark urine; pain in the upper or middle abdomen and back; weight loss for no known reason; loss of appetite; fatigue.

We hypothesize that AMPLIGEN®, being a dsRNA, will mainly activate antigen presenting cells. This, in turn, could lead to increased numbers of monocytes and dendritic cells, which subsequently could lead to increased numbers of CD8 T cells and decreased numbers of regulatory T cells or myeloid-derived suppressor cells.

Conventional treatments of Pancreatic cancers are wanting. The current standard of care (SOC) for locally advanced and metastatic pancreatic carcinoma is FOLFIRINOX, a four-drug cocktail with significant toxicity. Approval of FOLFIRINOX was based on the Phase 2/3 ACCORD study published in 2011 (Von Hoff et al., 2011). In this study, FOLFIRINOX was compared to Gemcitabine, which was the SOC at that time.

TABLE 1

First-Line Therapy: Results of the ACORD Study*

| Parameter | FOLFIRINOX | Gemcitabine | p-value |
|---|---|---|---|
| Overall Survival (OS) months | 11.1 | 6.8 | $p < 0.001$ |
| Progression Free Survival (PFS) months | 6.4 | 3.3 | $p < 0.001$ |

TABLE 1-continued

| First-Line Therapy: Results of the ACORD Study* | | | |
|---|---|---|---|
| Parameter | FOLFIRINOX | Gemcitabine | p-value |
| Complete Response Rates (CR) n(%) | 1(0.6) | 0(0) | — |
| Partial Response Rates (PR) n(%) | 53(31.0) | 16(9.4) | p < 0.001 |

*n = 171 FOLFIRINOX arm
n = 171 Gemcitabine arm
Conroy et al. *NEJM* 2011; 364(19): 1817

TABLE 1 shows the results of the ACCORD study. Overall Survival (OS) increased from 6.8 months with Gemcitabine to 11.1 months with FOLFIRINOX (p<0.001). However, the Complete Response Rate (CR) was only 0.6%. Moreover, as shown in TABLE 2, the overall mean survival with second-line therapy following progression on the FOLFIRINOX was only 4.05 months.

TABLE 2

| Survival with Second-Line Therapy Following Progression on FOLFIRINOX | | | | |
|---|---|---|---|---|
| Parameter | Gemcitabine Viaud, et al. 2017 | Gemcitabine Gilabert, et al. 2017 | Gemcitabine da Rocha, et al. 2015 | Overall (mean) |
| Overall Survival (OS) (months) | 3.7 | n/a | 5.7 | 4.05* |
| Progression Free Survival (PFS) (months) | 2.1 | 2.5 | 2.0 | 2.24* |
| Complete Response Rates (CR) (%) | 0% | 0% | 0% | 0%* |
| Partial Response Rates (PR) (%) | 8.3% | 5.5% | 0% | 6.4% |
| Number of Patients (n) | 96 | 72 | 20 | 188 |

*weighted average based on n in each study

These methods are not satisfactory as evidenced by the high mortality rate.

Unfortunately, the rapidly growing field of immunotherapy using checkpoint blockade has have not encountered success in patients with adenocarcinoma of the pancreas. Patients with pancreatic carcinoma show poor response rates to checkpoint blockage using anti-PD1, anti-PD-L1, and anti-CTLA-4 drugs.

The TME in pancreatic cancer is dominated by immunosuppressive cells including $T_{reg}$ cells and lacks $T_{eff}$ cells needed to drive an anti-tumor response (Liyanage et al., 2002; Hiraoka et al., 2006). In a minority of patients with lower prevalence of $T_{reg}$ cells in the TME, a better prognosis was seen. (Hiraoka et al., 2006).

Importantly, the lack of $T_{effector}$ cells in the TME of patients with pancreatic carcinoma appears to be related to the failure of these $T_{effector}$ cells to migrate from the bone marrow and blood of pancreatic cancer patients to the TME, since high levels of tumor-reactive T cells were easily found in bone marrow samples of patients with pancreatic carcinoma.

Thus, these findings suggest that the failure of immunotherapy in pancreatic carcinoma is not because of a lack of antigenicity of the tumor itself or a lack of $T_{effector}$ cells directed against tumor antigens, but a failure to recruit $T_{effector}$ cells into the TME while at the same time reducing the level of $T_{reg}$ cells in the TME.

We note that in Pancreatic Cancer tumor-infiltrating CD4+ T cells (high), CD8+ T cells (high), and % $T_{reg}$ cells (low) in the TME are all independent prognosticators of increased overall survival (Ino et al., 2013). Further, in Pancreatic Cancer $T_{reg}$ infiltration into the TME is a bad prognostic indicator for survival. Hiraoka et al. divided pancreatic cancer patients into two cohorts based on values of the $T_{reg}$ cells being higher or lower than the median value in the TME, the low $T_{reg}$ group showed significantly better survival than the high $T_{reg}$ group (Hiraoka et al., 2006).

We performed experiments to determine if AMPLIGEN® can increase the $T_{eff}$ cell to $T_{reg}$ cell ratio thereby converting a "cold" pancreatic TME into a "hot" pancreatic TME. This is highly relevant for improving the likelihood of an anti-tumor response to checkpoint blockade. As shown below in a preclinical model of pancreatic cancer, the combination of AMPLIGEN® and checkpoint blockade (anti-PD-L1) was synergistic in increasing both overall survival and time-to-tumor progression (FIG. 1).

FIG. 1 shows AMPLIGEN® was tested in mice against pancreatic tumors in conjunction with an anti-PD-L1, and AMPLIGEN® was shown to synergistically increase survival as well as time to tumor progression (p=0.029 and 0.0418, respectively). Please note that all four cohorts (control, AMPLIGEN®, anti-PD-L1, AMPLIGEN®+anti-PD-L1) were studied in the same parallel experiment. The separate figures (FIGS. 1A, 1B, 1C, 1D, 1E and 1F) were used to increase clarity.

It was found that a combination of AMPLIGEN® and a checkpoint inhibitor can synergistically increase time to progression in a mouse model of pancreatic cancer. See Table 3. In this experiment, sub-therapeutic doses of AMPLIGEN® were administered in mouse models of pancreatic cancer. Since the dose was sub-therapeutic, there was no effect on the time to progression which remained at 33 days and which was the same as the untreated mice. Similarly, the administration of sub-therapeutic doses of checkpoint inhibitor also had no effect on the time to progression which remains the same as the untreated population at 33 days. However, the administration of a combination of the same sub-therapeutic dose of AMPLIGEN® and the same sub-therapeutic dose of checkpoint inhibitor induced a synergistic increase in the time to progression to 73 days.

TABLE 3

| Synergistic Increase in Time to Progression in a Mouse Model of Pancreatic Cancer Using AMPLIGEN ® Plus Checkpoint Blockade | |
|---|---|
| Cohorts (n = 8 each) | Time to Progression Median - Days |
| 1) Control | 33 |
| 2) AMPLIGEN ® | 33 0* |
| 3) Anti-PD-L1 | 33 0* |
| 4) AMPLIGEN ® + Anti-PD-L1 | 73 40* |

*Increased Time to Progression

A Low Systemic Immune-Inflammation Index (SIII) Predicts Greater Survival in Pancreatic Cancer. Using the Systemic-Immune-Inflammation Index (SIII) as a Prognostic Marker in Pancreatic Cancer can predict survival in resectable pancreatic cancer. A low SIII (≤900) predicts a greater survival. SIII=Neutrophils/lymphocytes ratio (NLR)×thrombocytes in the peripheral blood. Patient cohorts with low SIII (N=164) compared to those with high SIII (n=141) had a significantly longer survival rate (p<0.001). See, FIG. 2 where SIII=Neutrophils/lymphocytes ratio (NLR)×thrombocytes in the peripheral blood.

Figure 3:
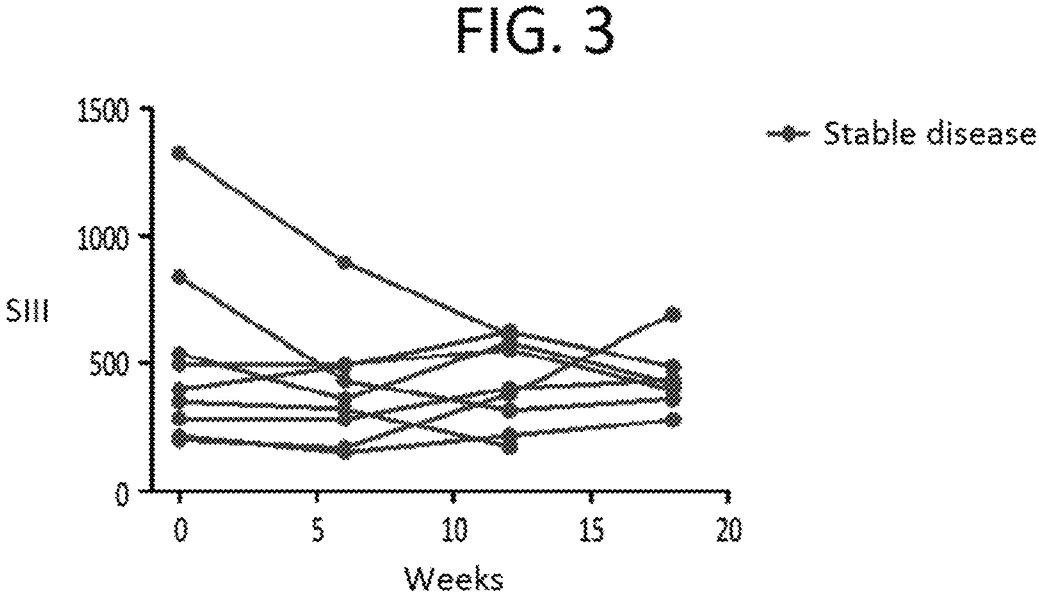
FIG. 3 Depicts declining SIII data over 18 weeks for nine patients with stabilization of metastatic pancreatic carcinoma following AMPLIGEN® treatment.

AMPLIGEN® clinical treatment results: Decreasing SIII levels up to 18 weeks in 9 pancreatic cancer patients receiving AMPLIGEN® (IV) 400 mg twice weekly with stabilized metastatic disease. See FIG. 3.

A decrease in SIII is a favorable prognostic sign for increased survival.

Preclinical Model

AMPLIGEN® was also tested in mice against pancreatic tumors in conjunction with an anti-PD-L1 and was shown to synergistically increase survival. See, FIG. 1, panels labeled "Percent Survival." As well as time to tumor progression. See, FIG. 1, panels labeled "Time-to-tumor progression."

Example 3: Melanoma

Similar to the pancreatic cancer success above showing synergy using AMPLIGEN® plus checkpoint blockage, we also see positive synergistic anti tumor responses in a melanoma animal model.

Rintatolimod together with anti-PD-L1 antibodies were tested for anti-tumor activity against established subcutaneous B16 melanoma tumors in C57BL/6 mice. Mice (10 animals per group) were inoculated with 0.4×10E6 B16-F10 tumor cells in their shaved rear flanks. Seven days later (when tumors reached 0.3 to 0.5 cm in their largest diameter), mice were randomized for tumor sizes, and individually tagged and were allocated to the following six treatment groups:

No treatment (negative controls)
Rintatolimod alone 100 μg/dose 4×
Rintatolimod alone 250 μg/dose 4×
Anti-PD-L1 mAb alone
Rintatolimod 100 μg/dose 4× plus anti-PD-L1 mAb
Rintatolimod 250 μg/dose 4× plus anti-PD-L1 mAb Rintatolimod was injected intravenously at 100 or 250 micrograms/dose and was repeated 4 times, 5 days apart. Anti-PD-L1 mAb (clone 10F.9G2, BioXCell) was administered intraperitoneally on Days 1 and 3 after each rintatolimod injection at a 200 microgram/dose. Tumors were measured 3 times per week using a set of calipers, taking measurement of 2 opposing diameters and were recorded as tumor areas. Mice exhibiting ulcerated tumors or tumors larger than 2 cm diameter (any direction) were euthanized following IACUC (Institutional Animal Care and Use Committee) policies.

Results were presented as tumor sizes for individual mice throughout the time of therapy, average tumor size in each group and survival up to Day 30 (time to euthanasia).

Results:

Tumor Responses at Day 30

One complete tumor regression was seen by Day 30 in each of the three (3) cohorts that received the anti-PD-L1 mAb. The only cohort that had more than one significant tumor regression was the rintatolimod 250 μg+anti-PD-L1 group. As shown in TABLE 4 the rintatolimod 250 μg+anti-PD-L1 group had two mice with major partial responses (PRs) of 70 and 86% reductions in the tumor size (per RECIST v1.1 criteria) in addition to the complete response (CR).

Summary of Tumor Responses:

AMPLIGEN® was synergistic with anti-PD-L1, yielding an increased anti-tumor response in a B16 mouse melanoma model The decrease in tumor size was significant for the AMPLIGEN® 250 μg+anti-PD-L1 cohort compared to anti-PD-L1 cohort alone (p=0.023).

The addition of AMPLIGEN® to anti-PD-L1 increased the objective response rate 3-fold, from 10% with anti-PD-L1 alone to 30% with the combination.

TABLE 4

SYNERGISTIC ANTI-TUMOR RESPONSES* IN MELANOMA MOUSE MODEL

| Group (n = 10) | Number of Complete Responses (CR) | Number of Partial Responses (PR) | % Tumor Reduction in PRs | Total # Tumor Responses CR + PR |
|---|---|---|---|---|
| No Treatment Control | 0 | 0 | — | 0 |
| 100 μg rintatolimod | 0 | 0 | — | 0 |
| 250 μg rintatolimod | 0 | 0 | — | 0 |
| Anti-PD-L1 | 1 | 0 | — | 1 |
| 100 μg rintatolimod + Anti-PD-L1 | 1 | 0 | — | 1 |
| 250 μg rintatolimod + Anti-PD-L1 | 1 | 2 | 70% and 86% | 3 |

*Tumor assessments were performed per RECIST vI.I. criteria.

Figure 4:
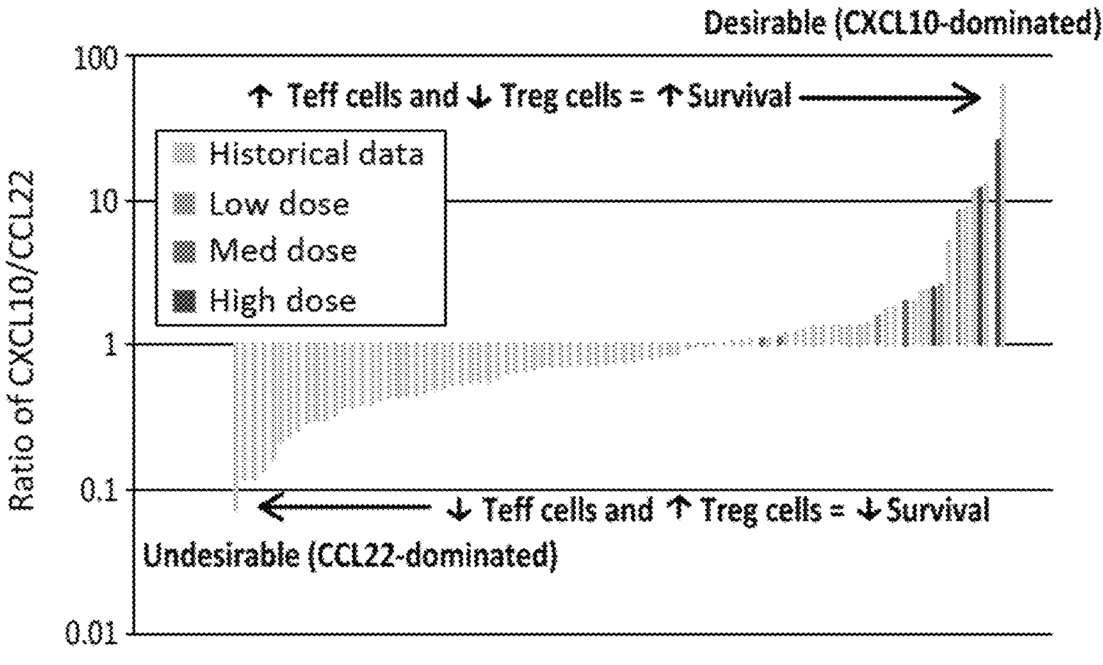
FIG. 4 Depicts significantly improved ratio of CXCL10 ("good" C-X-C Motif Chemokine 10):CCL22 ("bad" C-C Motif Chemokine Ligand 22) chemokines in tumor samples from colorectal cancer patients treated with tdsRNA vs. historical data similarly collected (p=0.0015).
Figure 5:
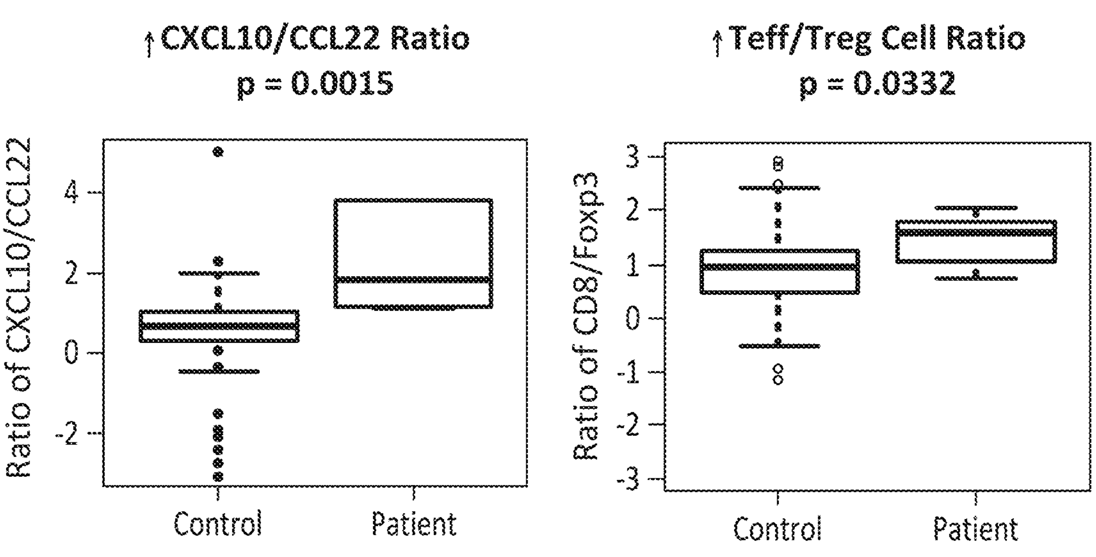
FIG. 5 Depicts the improved ratios of chemokines CXCL10 ("good" C-X-C Motif Chemokine 10)/CCL22 ("bad" C-C Motif Chemokine Ligand 22) and T cell markers ($T_{eff}$ to $T_{reg}$ ratio) in resected tumors following tdsRNA treatment (Patients vs. Historical Controls).

Example 4: Results From a Clinical Trial Examining the Positive Effects of AMPLIGEN® on the TME of Colorectal Cancer Similar to the pancreatic cancer success above, we also see positive results with colorectal cancer. As shown in FIG. 4 and FIG. 5, a colorectal carcinoma trial of AMPLIGEN® plus rIFNa-2b and celecoxib produced an increased ratio of CXCL10 (C-X-C Motif Chemokine 10) to CCL22 (C-C Motif Chemokine Ligand 22) in the TME along with an increase in the ratio of $T_{eff}/T_{reg}$ markers in 9 patients with metastatic colorectal carcinoma compared to historical controls. FIG. 4 depicts a significantly improved ratio of CXCL10 ("good" C-X-C Motif Chemokine 10):CCL22 ("bad" C-C Motif Chemokine Ligand 22) chemokines in tumor samples vs. historical data similarly collected (p=0.0015). See, also, FIG. 5 which depicts the ratios of chemokines and T cell markers in resected tumors following AMPLIGEN® treatment (Patients vs. Historical Controls).

FIG. 5 shows that AMPLIGEN® (rintatolimod) has an ability to convert "cold" tumors into "hot" tumors which are much more likely to respond to checkpoint blockage.

We also found that AMPLIGEN® plus checkpoint blockage increased survival in an animal model of colorectal carcinoma In a mouse model of colorectal carcinoma, the combination of AMPLIGEN® plus an anti-mouse-PD-1 monoclonal antibody showed a median survival increase of greater than 250% compared to anti-PD-1 alone. See, FIG. 6.

Example 5: Bladder Carcinoma

Similar to the pancreatic cancer and melanoma successes above, we also see positive results with bladder carcinoma.

AMPLIGEN® significantly inhibited the growth of human bladder tumor xenografts in nude mice and appeared to work, at least in part, by an immune enhancing mechanism.

Example 6: Renal Carcinoma

Similar to the pancreatic cancer success above, we also see positive results with renal carcinomas (also referred to in this disclosure as renal cell cancer, renal cell carcinoma, kidney cancer).

Renal Cell Carcinoma

Antitumor activity of AMPLIGEN® on human renal cell carcinoma xenografts in nude mice. AMPLIGEN® caused statistically significant tumor growth inhibition ($p<0.001$) and increased survival ($p<0.002$) (Hubbell, 1990).

Figure 7:
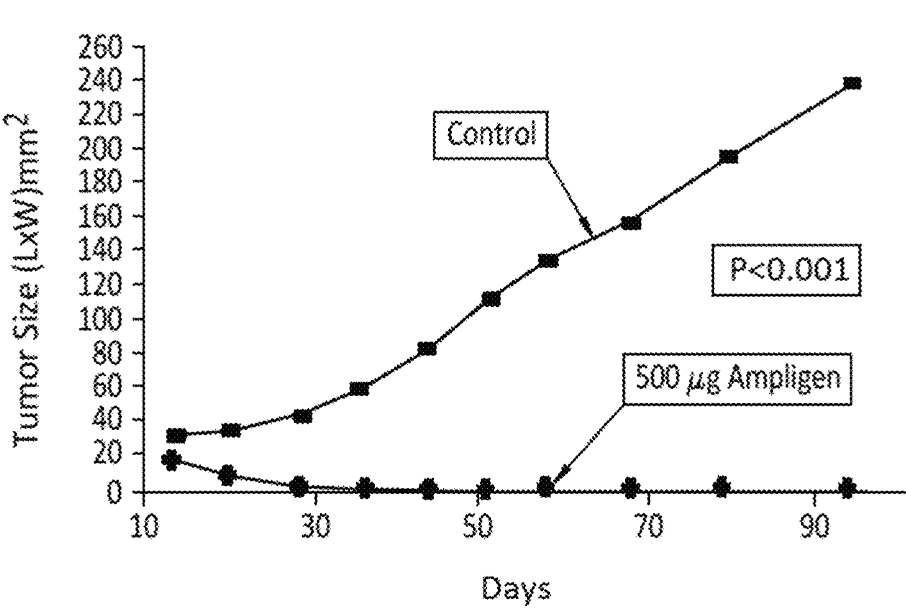
FIG. 7 Growth Inhibition of Renal Cell Carcinoma (786 0) Xenografts Nude Mice Treated with AMPLIGEN. Depicts the growth inhibition of renal cell carcinoma (786-0) xenografts with tdsRNA (bottom curve) compared to untreated controls (upper curve).
Figure 8:
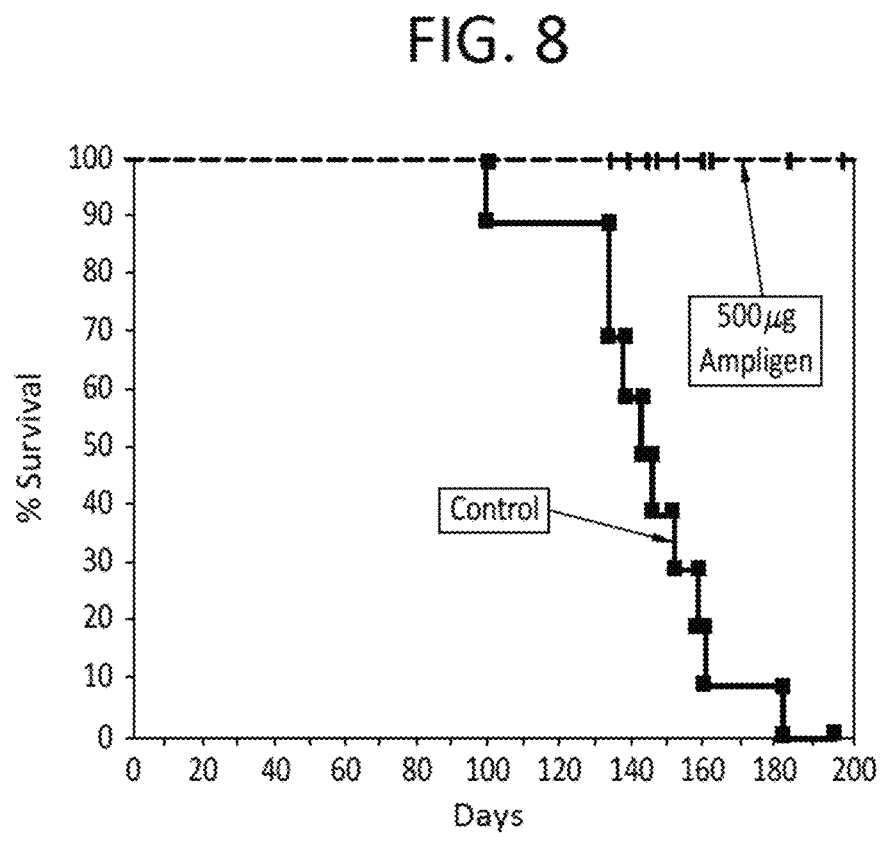

FIG. 7 and FIG. 8 illustrate the results of rintatolimod (AMPLIGEN®) given as a monotherapy, where rintatolimod demonstrated an ability to increase anti-tumor immune mechanisms and survival. Results indicate that rintatolimod has direct anti-tumor effects and its augmentation of innate immune responses (Natural Killer cells, also called NK cells) could have a key role in tumor regression. As shown in FIG. 7 and FIG. 8, rintatolimod was effective at both inhibiting tumor growth (tumor regression was observed in each mouse) and increasing survival, where 90% of mice given rintatolimod were free of the residual tumor while 100% of the control group had died secondary to tumor growth.

Example 7: Combinatorial Immunotherapy of AMPLIGEN® (Rintatolimod) Poly I:Poly C12U and Blockade of Programmed Death-Ligand 1 Against Established Melanoma Tumors in a Mouse Model In this experimental sample, we were able to show that AMPLIGEN® induced anti-tumor synergy when it is administered with a checkpoint blockade. Specifically, we found that:

(1) AMPLIGEN® was synergistic with anti-PD-L1, yielding an increased anti-tumor response in a mouse melanoma model.

(2) The anti-tumor effect was significantly greater for the AMPLIGEN® 250 μg+anti-PD-L1 cohort compared to the anti-PD-L1 cohort alone and the AMPLIGEN® 250 ug cohort alone ($p=0.023$).

(3) addition of AMPLIGEN® to anti-PD-L1 synergistically increased the number of responding tumors that were decreasing in size as early as DAY 9.

The studies were conducted as follows:

AMPLIGEN® and anti-PD-L1 antibodies were tested for anti-tumor activity against established subcutaneous B16 melanoma tumors in C57BL/6 mice. Briefly, mice (10 animals per group) were inoculated with 0.4×10E6 (i.e., 400,000) B16-F10 tumor cells in their shaved rear flanks. Seven days later, mice were randomized to six treatment groups as follows: (Group 1) No treatment (negative controls); (Group 2) AMPLIGEN® alone 100 μg/dose 4×; (Group 3) AMPLIGEN® alone 250 μg/dose 4×; (Group 4) Anti-PD-L1 mAb alone; (Group 5) AMPLIGEN® 100 μg/dose 4× plus anti-PD-L1 mAb; (Group 6) AMPLIGEN® 250 μg/dose 4× plus anti-PD-L1 mAb. mAb refers to monoclonal antibody.

AMPLIGEN® was injected IV at 100 or 250 μg/dose 4 times, 5 days apart. Anti-PD-L1 mAb was administered IP on Days 1 and 3 after each AMPLIGEN® dose at 200 μg/dose. Tumors were measured 3 times per week using calipers, measuring 2 opposing diameters. Mice exhibiting ulcerated tumors or tumors greater than 2 cm in diameter were euthanized starting on day 14. This confounded the analysis of tumor sizes after day 12. Results were presented as tumor sizes for individual mice throughout time of therapy up to Day 30.

The data shows that AMPLIGEN® 250 μg+anti-PD-L1 cohort had more tumor regressions by Day 9 (70%) compared to the AMPLIGEN® 250 μg only cohort (0%) and the anti-PD-L1 only cohort with (20%).

TABLE 5

Changes in Tumor Size from Day 0Δ to Day 9; Tumor Size Changes measured in mm2

| Mouse # | AMPLIGEN ® 250 μg only | Anti-PD-L1 Only | AMPLIGEN ® 250 μg + Anti PD-L1 |
|---|---|---|---|
| 1 | 61.42 | 1.10 (CR) | −15.66* |
| 2 | 77.69 | −12.19* | −2.27* (PR) |
| 3 | 19.00 | 61.99 | 22.88 |
| 4 | 4.94 | −3.48* | 25.35 |
| 5 | 60.53 | 78.44 | −11.28* (PR) |
| 6 | 81.19 | 55.94 | −13.51* (CR) |
| 7 | 289.4 | 4.65 | −18.33* |
| 8 | 71.34 | 23.15 | −10.48* |
| 9 | 202.3 | 49.56 | −14.20* |
| 10 | 39.94 | 0.09 | 9.77 |
| Totals | 907.8 | 259.3 | −27.7* |

*= Negative values (i.e., tumors decreased in size)
+ ANOVA
ΔFirst tumor size measurement and first dose of AMPLIGEN ® occurred on Day 0.

Synergism was also seen in a decrease in tumor size. Briefly, a significantly greater number of tumors in the AMPLIGEN® 250 μg+Anti-PD-L1 Cohort Decreased in Size.

TABLE 6 shows a comparison of the Number of Tumors Which Decreased in Size at Day 9 Compared to Day 0Δ

| Mouse Cohort | Number of Tumors Increased in Size | Number of Tumors Decreased in Size | p-value |
|---|---|---|---|
| 250 μg AMPLIGEN ® Only (n = 10) | 10 | 0 | 0.0025* |
| Anti-PD-L1 Only (n = 10) | 8 | 2 | |
| 250 μg AMPLIGEN ® + Anti-PD-L1 (n = 10) | 3 | 7 | |

*Fisher's Exact Test (2-sided)
ΔFirst tumor size measurement and first dose of AMPLIGEN ® occurred on Day 0

In conclusion, AMPLIGEN® was synergistic with anti-PD-L1 yielding an increased anti-tumor response in this melanoma model. At both Days 9 and 12 the anti-tumor effect was significantly greater for the AMPLIGEN® 250 μg+anti-PD-L1 cohort compared to the anti-PD-L1 cohort alone ($p=0.023$). Tumor reductions were seen at Days 9 and 12 in the AMPLIGEN® 250 μg+anti-PD-L1 cohort translated into 1 CR and 2 PRs by Day 30. Thus, compared to the one CR seen in the anti-PD-L1 alone cohort, or a 10% overall response rate, the AMPLIGEN® 250 μg+anti-PD-L1 cohort had a 30% overall response rate at Day 30.

Example 8: Clinical Antitumor Responses in Patients Treated with the Combination of Ampligen (tdsRNA) Plus a Checkpoint Blockade Inhibitor Checkpoint blockade inhibitors or "checkpoint inhibitors" are molecules that can inhibit or block immune checkpoint proteins, such as PD-1 or PD-L1. Currently FDA approved checkpoint inhibitors block CTLA4, PD-1 and PD-L1. The goal of these drugs is to unleash a cellular immune response to attack and destroy cancer cells. However, the currently approved checkpoint inhibitors, such as pembrolizumab and nivolumab, only induce antitumor responses in a minority of patients.

Figure 6:
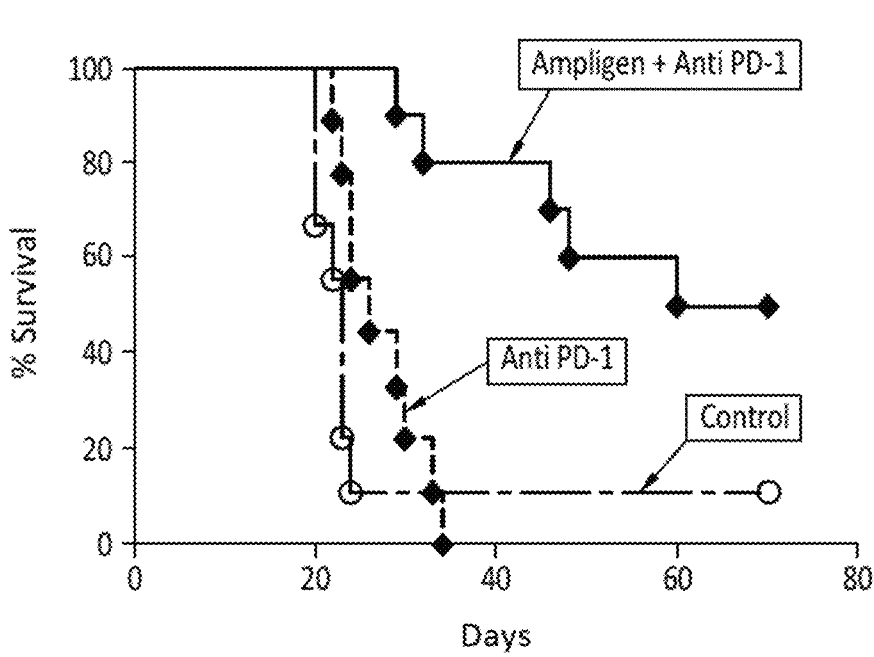
FIG. 6 Depicts increased survival of greater than 250% using the combination of tdsRNA plus anti-PD-1 compared to anti-PD-1 alone.

Therefore, one goal of immunotherapy is the reprogramming of the tumor microenvironment (TME) to convert "cold" tumors (unresponsive) to "hot" tumors that will be responsive to checkpoint blockade. FIGS. 4 and 5 show examples of Ampligen's ability to convert "cold" tumors into "hot" tumors by increasing the ratios of Teff cells:Treg cells in the TME. FIGS. 1 and 6 and Tables 3, 4, 5, and 6 show examples of Ampligen's ability to synergistically boost the antitumor activity of checkpoint inhibitors in animal models.

FIGS. 9 and 10 show the ability of Ampligen plus checkpoint inhibitor treatment to induce clinical responses in patients with two different cancer types, Triple Negative Breast Cancer (TNBC) and Metastatic Recurrent Ovarian Cancer (MROC) that do not respond to checkpoint inhibitors as single agents.

Figures 9A, 9B:
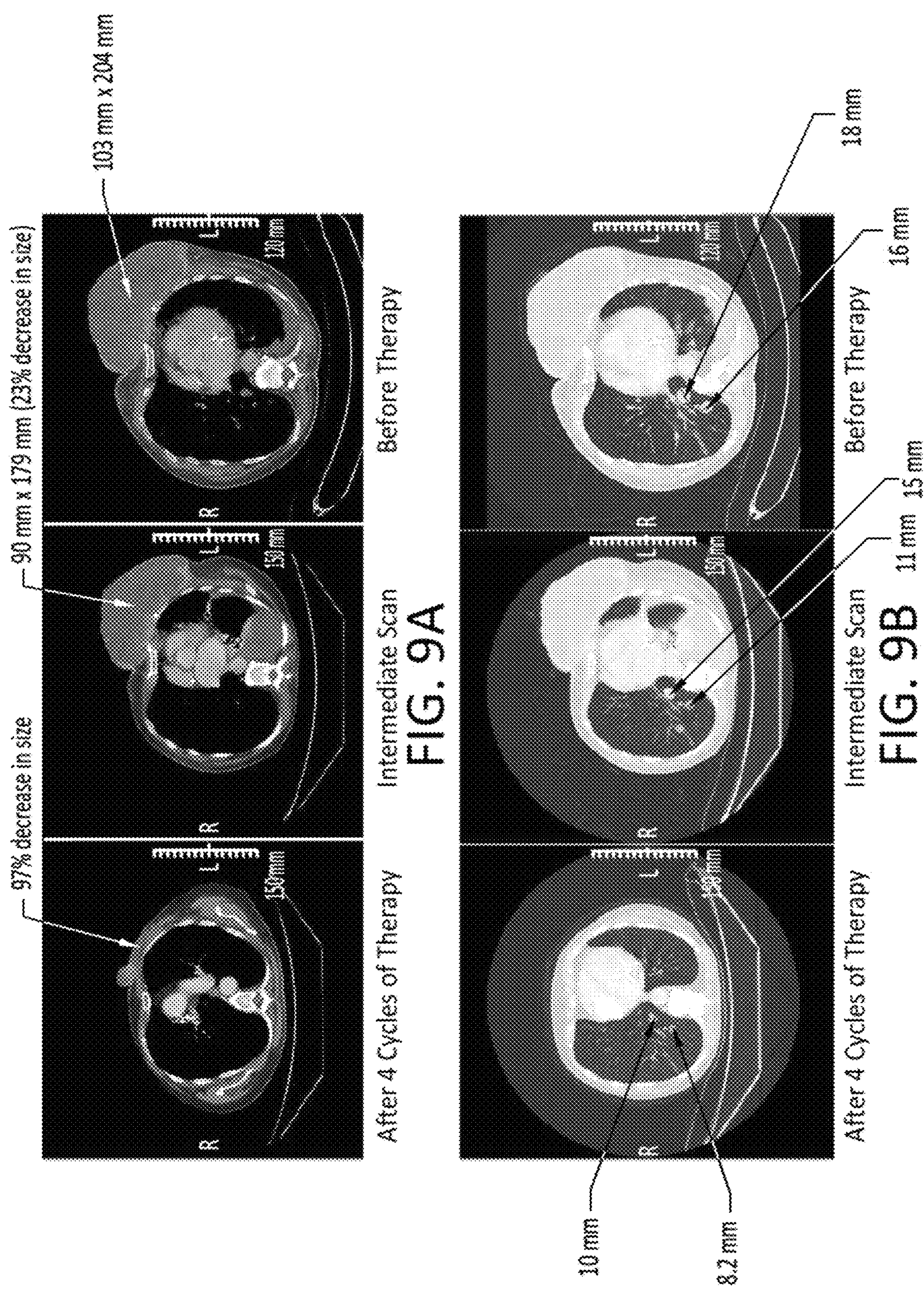
FIG. 9 Depicts CT scan of the thorax showing a dramatic clinical response of triple negative breast cancer.

FIGS. 9A and 9B show the CT scan images over time of a woman with a massive left breast cancer tumor mass (far right image) prior to treatment with 4 cycles of chemokine modulating therapy using Ampligen plus pembrolizumab. The center CT scan taken during treatment shows that the large tumor mass had decreased in size by 23%. Moreover, after completion of the 4 cycles of immunotherapy with Ampligen plus pembrolizumab the entire tumor became necrotic and the dead tumor tissue began to fall off the chest wall in a dramatic fashion. The CT image on the far left shows that the tumor mass decreased in size by greater than 97%. In addition, metastatic breast cancer nodules in the lung also decreased in size (FIG. 9B) and the plural effusions cleared up.

Pembrolizumab is not FDA approved for breast cancer because of its very low response rate. The probability of obtaining this magnitude of a clinical response in TNBC is less than 1% using only pembrolizumab. Also, Ampligen as a single agent has not shown antitumor activity against breast cancer. Therefore, this is an example of clinical antitumor synergy using Ampligen plus checkpoint inhibitor therapy. Moreover, this was the first patient treated with the combination of Ampligen plus a checkpoint inhibitor.

Figures 10A, 10B, 10C, 10D:
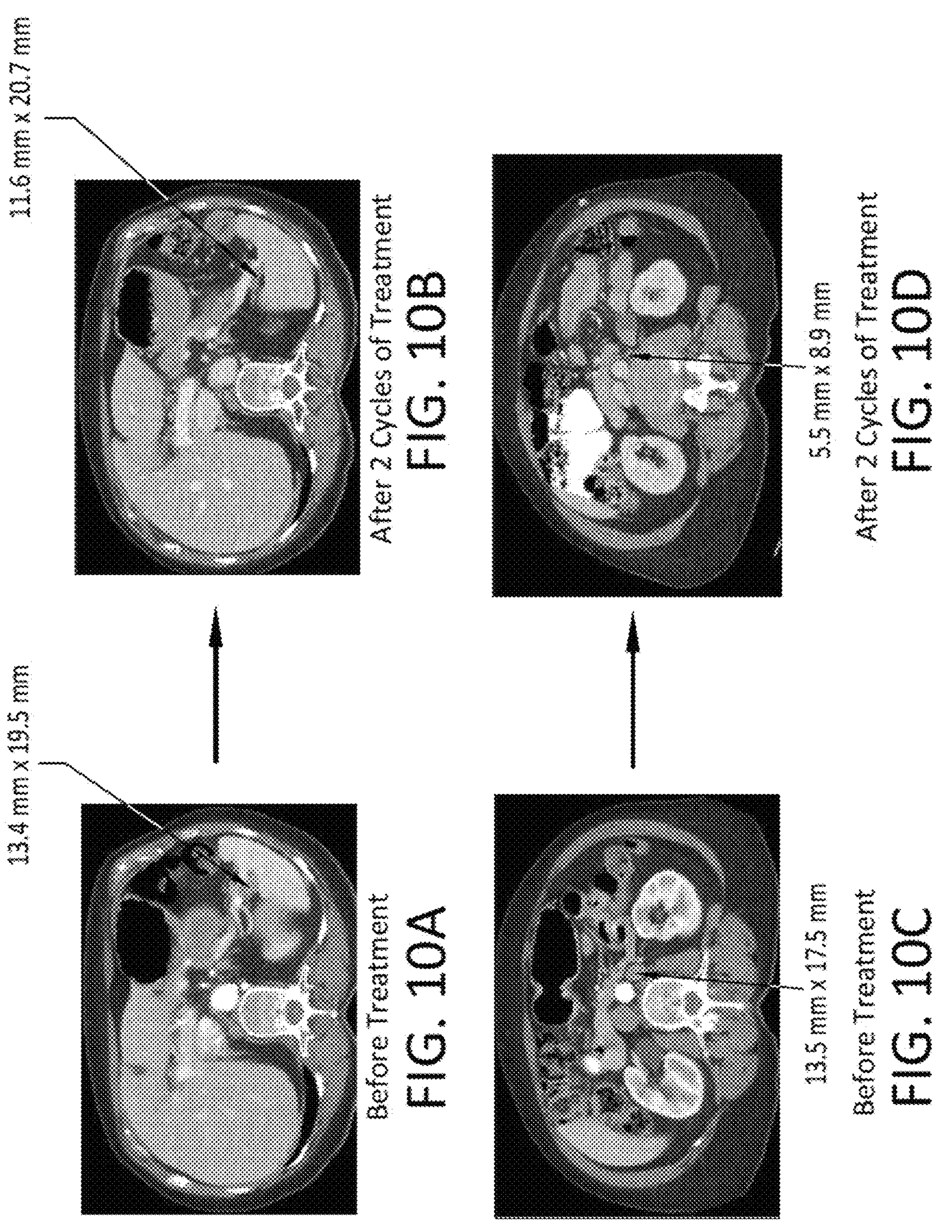
FIG. 10 Depicts CT scan of the peritoneal cavity showing a partial clinical response of ovarian cancer which became a complete response (CR).

FIGS. 10A and 10B show a partial antitumor response (42% decrease in size) in a woman with metastatic recurrent ovarian cancer (MROC) after only 2 cycles of Ampligen/pembrolizumab/cisplatin. Again, this is the first patient with MROC treated with Ampligen plus a checkpoint inhibitor. After 4 cycles of immunotherapy this patient was in complete remission.

Pembrolizumab has low antitumor activity in ovarian cancer and is not approved for the ovarian cancer indication. The probability that cisplatin alone would have any significant activity in this patient who relapsed after initial cisplatin chemotherapy is low. Ampligen was included in this combination to attempt to induce a synergistic antitumor response and the fact that a complete response (CR) was induced is evidence that a synergistic anti-cancer effect occurred.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

We claim:

1. A method for treating a cancer in a subject in need thereof, the method consisting of administering to the subject a first compound and a second compound, together or separately in either order;

wherein the first compound is an effective amount of Pembrolizumab, optionally with at least one pharmaceutically-acceptable carrier; and wherein the second compound is an effective amount of Rintatolimod, optionally with at least one pharmaceutically-acceptable carrier;

wherein the Rintatolimod and the Pembrolizumab together provide a synergistic effect in the treatment of the cancer over Rintatolimod alone, Pembrolizumab alone, or a sum of Rintatolimod alone and Pembrolizumab alone.

2. The method of claim 1, wherein treating a cancer comprises at least one selected from the group consisting of:

inhibiting proliferation of tumor cells of the cancer in a subject;

initiating an effect of Pembrolizumab in the subject;

enhancing effects of Pembrolizumab in the subject;

prolonging effects of Pembrolizumab in the subject; and activating a response to Pembrolizumab in the subject.

3. The method of claim 1, wherein the cancer is at least one selected from the group consisting of:

pancreatic cancer;

skin cancer;

colorectal cancer;

ovarian cancer;

melanoma;

breast cancer;

triple negative breast cancer;

head and neck tumor;

bladder cancer;

renal cell carcinoma; and lung cancer.

4. The method of claim 1, wherein the Rintatolimod is complexed with a stabilizing polymer.

5. The method of claim 4, wherein the stabilizing polymer is selected from the group consisting of polylysine; polylysine plus carboxymethylcellulose; polyarginine; polyarginine plus carboxymethylcellulose; and a combination thereof.

6. The method of claim 1, wherein the effective amount of Rintatolimod is a synergistic, therapeutically effective amount.

7. The method of claim 2, wherein a combination of the Rintatolimod and the Pembrolizumab administered provides a synergistic effect in inhibiting proliferation of tumor cells of the cancer.

8. The method of claim 7, wherein the synergistic effect is selected from the group consisting of:

increasing survival of the subject;

increasing time of progression of the subject;

inhibiting tumor growth;

inducing tumor cell death;

increasing tumor regression;
preventing tumor recurrence;
preventing tumor growth;
preventing tumor spread;
delaying tumor recurrence;
delaying tumor growth;
delaying tumor spread; and
promoting tumor elimination.

9. The method of claim 1, wherein the effective amount of Pembrolizumab is a synergistic, therapeutically effective amount.

10. The method of claim 9, wherein the Pembrolizumab administered provides an additive or synergistic effect in treatment of the cancer or an additive or synergistic effect in inhibition of proliferation of a tumor.

11. The method of claim 1, wherein administering is administering intravenously; administering intradermally; administering subcutaneously; administering intramuscularly; administering intranasally; administering intraperitoneally; administering intracranially; administering intravesically; administering orally; or administering topically.

12. The method of claim 1, wherein the Rintatolimod and the Pembrolizumab are administered at the same time.

13. The method of claim 1, wherein the Rintatolimod and the Pembrolizumab are administered separately at different time intervals; and wherein the Rintatolimod is administered at a frequency selected from the group consisting of once a month; once every 3 weeks; once every two weeks; once weekly; twice weekly; 3 times weekly; 4 times weekly; 5 times weekly; 6 times weekly; and daily.

14. The method of claim 1, wherein the Rintatolimod and the Pembrolizumab are administered separately but within a time period selected from the group consisting of 2 months; 1 month; 3 weeks; 2 weeks; 1 week; 3 days; 1 day; 12 hours; 6 hours; 3 hours; 2 hours; 1 hour; and 30 minutes.

15. The method of claim 1, wherein the second compound comprising Rintatolimod is administered to the subject intravenously one to five times a week at a dosage which will provide on average of about 25-700 milligram per day of Rintatolimod for up to one month or longer than one month.

16. The method of claim 1, wherein the second compound comprising Rintatolimod is administered to the subject one to five times a week at a dosage which will provide on average of about 25-700 milligram per day of Rintatolimod continuously for at least one month.

17. The method of claim 1, wherein the subject is a mammal.

18. The method of claim 17, wherein the mammal is a human.

19. The method of claim 18 wherein the human has a cancer that is nonresponsive to treatment by Pembrolizumab alone and/or that is nonresponsive to a chemotherapeutic drug alone.

20. A method for treating a cancer in a human subject in need thereof, the method consisting of exposing or contacting the cancer to a first compound and a second compound together or separately in either order;

wherein the first compound is an effective amount of a Pembrolizumab, optionally with at least one pharmaceutically-acceptable carrier; and wherein the second compound is an effective amount of a Rintatolimod, optionally with at least one pharmaceutically-acceptable carrier;

wherein the Rintatolimod and the Pembrolizumab together provide a synergistic effect in the treatment of the cancer over Rintatolimod alone, Pembrolizumab alone, or a sum of Rintatolimod alone and Pembrolizumab alone.

21. The method of claim 20, wherein the cancer is exposed to or contacted with a pharmaceutical composition comprising the first compound and the second compound.

* * * * *